(12) United States Patent
Rodriguez et al.

(10) Patent No.: US 7,662,795 B2
(45) Date of Patent: Feb. 16, 2010

(54) ENHANCEMENT OF ADENOVIRAL ONCOLYTIC ACTIVITY BY MODIFICATION OF THE E1A GENE PRODUCT

(75) Inventors: Ronald Rodriguez, Glenwood, MD (US); Ying Li, Gibson Island, MD (US)

(73) Assignee: The Johns Hopkins University, Baltimore, MD (US)

( * ) Notice: Subject to any disclaimer, the term of this patent is extended or adjusted under 35 U.S.C. 154(b) by 247 days.

(21) Appl. No.: 10/523,899

(22) PCT Filed: Aug. 8, 2003

(86) PCT No.: PCT/US03/25171
§ 371 (c)(1),
(2), (4) Date: Nov. 14, 2005

(87) PCT Pub. No.: WO2004/015086
PCT Pub. Date: Feb. 19, 2004

(65) Prior Publication Data
US 2006/0148073 A1 Jul. 6, 2006

Related U.S. Application Data

(60) Provisional application No. 60/401,919, filed on Aug. 8, 2002.

(51) Int. Cl.
*A61K 31/70* (2006.01)
*C12N 15/74* (2006.01)

(52) U.S. Cl. ............... 514/44; 435/320.1; 435/91.4
(58) Field of Classification Search .............. None
See application file for complete search history.

(56) References Cited

U.S. PATENT DOCUMENTS

| 5,457,049 | A | 10/1995 | Giordano |
| 6,495,130 | B1 | 12/2002 | Henderson et al. |
| 2002/0076401 | A1 | 6/2002 | Volloch et al. |

OTHER PUBLICATIONS

Deonarain, Expert Opin. Ther. Pat., 1998, vol. 8, pp. 53-69.*
Vile et al, Gene Ther 2000;7:2-8.*
Green et al, Cancer Gene Ther 2002;9:1036-42.*
Rodriguez et al, Cancer Res 1987;57:2559-63.*
Suzuki et al, Cancer Res 2001;61:1276-9.*
Becker et al, Mole Cell Biol 1989;9:3878-87.*

* cited by examiner

*Primary Examiner*—Q. Janice Li
(74) *Attorney, Agent, or Firm*—Edwards Angell Palmer & Dodge LLP; Peter F. Corless; Jonathan M. Sparks

(57) ABSTRACT

The present invention relates to compositions and methods for enhancing the oncolytic activity of replication-competent, target cell-specific adenovirus vectors by modification of the E1A gene product. The target cell-specific replication-competent adenovirus vectors comprise a chimera of an adenovirus gene essential for replication, preferably an early gene, and the Androgen receptor (or a portion thereof) under the transcriptional control of a cell type-specific transcriptional regulatory element (TRE). By providing for cell type-specific transcription through the use of one or more cell type-specific TREs, the adenovirus vectors effect prostate-specific cytotoxicity due to selective replication.

17 Claims, 26 Drawing Sheets

SEQ ID NO: 1

LOCUS Ad5E1A-AR\full-length\fusion 3768 bp DNA
SOURCE
 ORGANISM
COMMENT This file is created by Vector NTI
 http://www.informaxinc.com/
COMMENT VNTDATE|266338450|
COMMENT VNTAUTHORNAME|Ron Rodriguez|
BASE COUNT    832 a    1062 c    1083 g    791 t
ORIGIN

```
   1 accgggactg aaaatgagac atattatctg ccacggaggt gttattaccg aagaaatggc
  61 cgccagtctt ttggaccagc tgatcgaaga ggtactggct gataatcttc cacctcctag
 121 ccattttgaa ccacctaccc ttcacgaact gtatgattta gacgtgacgg cccccgaaga
 181 tcccaacgag gaggcggttt cgcagatttt tcccgactct gtaatgttgg cggtgcagga
 241 agggattgac ttactcactt ttccgccggc gcccggttct ccggagccgc ctcacctttc
 301 ccggcagccc gagcagccgg agcagagagc cttgggtccg gtttctatgc aaaccttgt
 361 accggaggtg atcgatctta cctgccacga ggctggcttt ccaccagtg acgacgagga
 421 tgaagagggt gaggagtttg tgttagatta tgtggagcac cccgggcacg gttgcaggtc
 481 ttgtcattat caccggagga atacggggga cccagatatt atgtgttcgc tttgxtatat
 541 gaggacctgt ggcatgtttg tctacagtaa gtgaaaatta tgggcagtgg gtgatagagt
 601 ggtgggtttg tgtgtggtaat ttttttttta atttttacag ttttgtggtt taaagaattt
 661 tgtattgtga ttttttttaaa aggtcctgtg tctgaacctg agcctgagcc cgagccagaa
 721 ccggagcctg caagacctac ccgccgtcct aaaatggcgc ctgctatcct gagacgcccg
 781 acatcacctg tgtctagaga atgcaatagt agtacggata gctgtgactc cggtccttct
 841 aacacacctc ctgagataca cccggtggtc ccgctgtgcc ccattaaacc agttgccgtg
 901 agagttggtg ggcgtcgcca ggctgtggaa tgtatcgagg acttgcttaa cgagcctggg
 961 caacctttgg acttgagctg taaacgcccc aggccagcgg ccgcagaagt gcagttaggg
1021 ctgggaaggg tctaccctcg gccgccgtcc aagacctacc gaggagcttt ccagaatctg
1081 ttccagagcg tgcgcgaagt gatccagaac ccgggcccca ggcacccaga ggccgcgagc
1141 gcagcacctc ccggcgccag tttgctgctg ctgcagcagc agcagcagca gcagcagcag
1201 cagcagcagc agcagcagca gcagcagcag cagcaagaga ctagccccag gcagcagcag
1261 cagcagcagg gtgaggatgg ttctccccaa gcccatcgta gaggccccac aggctacctg
1321 gtcctggatg aggaacagca accttcacag ccgcagtcgg ccctggagtg ccacccggag
1381 agaggttgcg tcccagagcc tggagccgcc gtggccgcca caaggggct gccgcagcag
1441 ctgccagcac ctccggacga ggctgactca gctgcccat ccacgttgtc cctgctgggc
1501 cccactttcc ccggcttaag cagctgctcc gctgaccta aagacatcct gagcgaggcc
1561 agcaccatgc aactccttca gcaacagcag caggaagcag tatccgaagg cagcagcagc
1621 gggagagcga gggaggcctc gggggctccc acttcctcca ggacaatta cttagggggc
1681 acttcgacca tttctgacaa cgccaaggag ttgtgtaagg cagtgtcggt gtccatgggc
1741 ctgggtgtgg aggcgttgga gcatctgagt ccaggggaac agcttcgggg ggattgcatg
1801 tacgccccac ttttgggagt tccaccgct gtgcgtccca ctccttgtgc cccattggcc
1861 gaatgcaaag ttctctgct agacgacagc gcaggcaaga gcactgaaga tactgctgag
1921 tattccccctt tcaagggagg ttacaccaaa gggctagaag gcgagagcct aggctgctct
1981 ggcagcgctg cagcagggag ctccgggaca cttgaactgc cgtctaccct gtctctctac
2041 aagtccggag cactggacga ggcagctgcg taccagagtc gcgactacta caactttcca
2101 ctggctctgg ccggaccgcc gccccctccg ccgcctcccc atcccacgc tcgcatcaag
2161 ctggagaacc cgctggacta cggcagcgcc tgggcggctg cggcggcgca gtgccgctat
```

Fig. 6-1

```
2221 ggggacctgg cgagcctgca tggcgcgggt gcagcgggac ccggttctgg gtcaccctca
2281 gccgccgctt cctcatcctg gcacactctc ttcacagccg aagaaggcca gttgtatgga
2341 ccgtgtggtg gtggtggggg tggtggcggc ggcggcggcg gcggcggcgg cggcggcggc
2401 ggcggcggcg gcggcggcga ggcgggagct gtagccccct acggctacac tcggccccct
2461 caggggctgg cgggccagga aagcgacttc accgcacctg atgtgtggta ccctggcggc
2521 atggtgagca gagtgcccta tcccagtccc acttgtgtca aaagcgaaat gggcccctgg
2581 atggatagct actccggacc ttacggggac atgcgtttgg agactgccag ggaccatgtt
2641 ttgcccattg actattactt tccaccccag aagacctgcc tgatctgtgg agatgaagct
2701 tctgggtgtc actatggagc tctcacatgt ggaagctgca aggtcttctt caaaagagcc
2761 gctgaaggga aacagaagta cctgtgcgcc agcagaaatg attgcactat tgataaattc
2821 cgaaggaaaa attgtccatc ttgtcgtctt cggaaatgtt atgaagcagg gatgactctg
2881 ggagcccgga agctgaagaa acttggtaat ctgaaactac aggaggaagg agaggcttcc
2941 agcaccacca gccccactga ggagacaacc cagaagctga cagtgtcaca cattgaaggc
3001 tatgaatgtc agcccatctt tctgaatgtc ctggaagcca ttgagccagg tgtagtgtgt
3061 gctggacacg acaacaacca gcccgactcc tttgcagcct tgctctctag cctcaatgaa
3121 ctgggagaga gacagcttgt acacgtggtc aagtgggcca aggccttgcc tggcttccgc
3181 aacttacacg tggacgacca gatggctgtc attcagtact cctggatggg gctcatggtg
3241 tttgccatgg gctggcgatc cttcaccaat gtcaactcca ggatgctcta cttcgcccct
3301 gatctggttt tcaatgagta ccgcatgcac aagtcccgga tgtacagcca gtgtgtccga
3361 atgaggcacc tctctcaaga gtttggatgg ctccaaatca ccccccagga attcctgtgc
3421 atgaaagcac tgctactctt cagcattatt ccagtggatg ggctgaaaaa tcaaaaattc
3481 tttgatgaac ttcgaatgaa ctacatcaag gaactcgatc gtatcattgc atgcaaaaga
3541 aaaaatccca catcctgctc aagacgcttc taccagctca ccaagctcct ggactcgtg
3601 cagcctattg cgagagagct gcatcagttc actttttgacc tgctaatcaa gtcacacatg
3661 gtgagcgtgg actttccgga aatgatggca gagatcatct ctgtgcaagt gcccaagatc
3721 ctttctggga aagtcaagcc catctatttc cacacccagt gactcgag
```

Fig. 6-2

SEQ ID NO: 2
LOCUS Ad5E1A-AR\TAD\fusion 2970 bp DNA
SOURCE
ORGANISM

BASE COUNT 628 a 845 c 899 g 598 t
ORIGIN

```
   1 accgggactg aaaatgagac atattatctg ccacggaggt gttattaccg aagaaatggc
  61 cgccagtctt ttggaccagc tgatcgaaga ggtactggct gataatcttc cacctcctag
 121 ccattttgaa ccacctaccc ttcacgaact gtatgattta gacgtgacgg cccccgaaga
 181 tcccaacgag gaggcggttt cgcagatttt tcccgactct gtaatgttgg cggtgcagga
 241 agggattgac ttactcactt ttccgccggc gcccggttct ccggagccgc ctcacctttc
 301 ccggcagccc gagcagccgg agcagagagc cttgggtccg gtttctatgc caaaccttgt
 361 accggaggtg atcgatctta cctgccacga ggctggcttt ccacccagtg acgacgagga
 421 tgaagagggt gaggagtttg tgttagatta tgtggagcac cccgggcacg gttgcaggtc
 481 ttgtcattat caccggagga atacggggga cccagatatt atgtgttcgc tttgctatat
 541 gaggacctgt ggcatgtttg tctacagtaa gtgaaaatta tgggcagtgg gtgatagagt
 601 ggtgggtttg gtgtggtaat tttttttta atttttacag ttttgtggtt taaagaatt
 661 tgtattgtga ttttttttaaa aggtcctgtg tctgaacctg agcctgagcc cgagccagaa
 721 ccggagcctg caagacctac ccgccgtcct aaaatggcgc ctgctatcct gagacgcccg
 781 acatcacctg tgtctagaga atgcaatagt agtacggata gctgtgactc cggtccttct
 841 aacacacctc atgagataca cccggtggtc ccgctgtgcc ccattaaacc agttgccgtg
 901 agagttggtg ggcgtcgcca ggctgtggaa tgtatcgagg acttgcttaa cgagcctggg
 961 caacctttgg acttgagctg taaacgcccc aggccagcgg ccgcagaagt gcagttaggg
1021 ctgggaaggg tctaccctcg gccgccgtcc aagacctacc gaggagcttt ccagaatctg
1081 ttccagagcg tgcgcgaagt gatccagaac ccgggcccca ggcacccaga ggccgcgagc
1141 gcagcacctc ccggcgccag tttgctgctg ctgcagcagc agcagcagca gcagcagcag
1201 cagcagcagc agcagcagca gcagcagcag cagcaagaga ctagccccag gcagcagcag
1261 cagcagcagg gtgaggatgg ttctccccaa gcccatcgta gaggccccac aggctacctg
1321 gtcctggatg aggaacagca accttcacag ccgcagtcgg ccctggagtg ccacccggag
1381 agaggttgcg tcccagagcc tggagccgcc gtggccgcca caaggggct gccgcagcag
1441 ctgccagcac ctccggacga ggatgactca gctgccccat ccacgttgtc cctgctgggc
1501 cccactttcc ccggcttaag cagctgctcc gctgaccta aagacatcct gagcgaggcc
1561 agcaccatgc aactccttca gcaacagcag caggaagcag tatccaagg cagcagcagc
1621 gggagagcga gggaggcctc ggggctccc acttcctcca aggacaatta cttaggggc
1681 acttcgacca tttctgacaa cgccaaggag ttgtgtaagg cagtgtcggt gccatgggc
1741 ctgggtgtgg aggcgttgga gcatctgagt ccaggggaac agcttcgggg ggattgcatg
1801 tacgccccac ttttgggagt tccaccgct gtgcgtccca ctcttgtgc cccattggcc
1861 gaatgcaaag gttctctgct agacgacagc gcaggcaaga gcactgaaga tactgctgag
1921 tattcccctt tcaagggagg ttacaccaaa gggctagaag gcgagagcct aggctgctct
1981 ggcagcgctg cagcagggag ctccgggaca cttgaactgc cgtctaccct gtctctctac
2041 aagtccggag cactggacga ggcagctgcg taccagagtc gcgactacta caactttcca
2101 ctggctctgg ccggaccgcc gccccctccg ccgcctcccc atcccacgc tcgcatcaag
```

Fig. 7-1

```
2161 ctggagaacc cgctggacta cggcagcgcc tgggcggctg cggcggcgca gtgccgctat
2221 ggggacctgg cgagcctgca tggcgcgggt gcagcgggac ccggttctgg gtcaccctca
2281 gccgccgctt cctcatcctg gcacactctc ttcacagccg aagaaggcca gttgtatgga
2341 ccgtgtggtg gtggtggggg tggtggcggc ggcggcggcg gcggcggcgg cggcggcggc
2401 ggcggcggcg gcggcggcga ggcgggagct gtagccccct acggctacac tcggccccct
2461 caggggctgg cgggccagga aagcgacttc accgcacctg atgtgtggta ccctggcggc
2521 atggtgagca gagtgcccta tcccagtccc acttgtgtca aaagcgaaat gggcccctgg
2581 atggatagct actccggacc ttacggggac atgcgtttgg agactgccag ggaccatgtt
2641 ttgcccattg actattactt tccaccccag aagacctgcc tgatctgtgg agatgaagct
2701 tctgggtgtc actatggagc tctcacatgt ggaagctgca aggtcttctt caaaagagcc
2761 gctgaaggga aacagaagta cctgtgcgcc agcagaaatg attgcactat tgataaattc
2821 cgaaggaaaa attgtccatc ttgtcgtctt cggaaatgtt atgaagcagg gatgactctg
2881 ggagcccgga agctgaagaa acttggtaat ctgaaactac aggaggaagg agaggcttcc
2941 agcaccacca gccccactga gtgactcgag
```

Fig. 7-2

SEQ ID NO: 3

LOCUS  Ad5E1A-AR\DBD\fusion 1305 bp  DNA
SOURCE
 ORGANISM
COMMENT  This file is created by Vector NTI
        http://www.informaxinc.com/
COMMENT   VNTDATE|266340593|
COMMENT   VNTAUTHORNAME|Ron Rodriguez|
BASE COUNT    307 a   311 c   362 g   325 t
ORIGIN

```
   1 accgggactg aaaatgagac atattatctg ccacggaggt gttattaccg aagaaatggc
  61 cgccagtctt ttggaccagc tgatcgaaga ggtactggct gataatcttc cacctcctag
 121 ccattttgaa ccacctaccc ttcacgaact gtatgattta gacgtgacgg cccccgaaga
 181 tcccaacgag gaggcggttt cgcagatttt tcccgactct gtaatgttgg cggtgcagga
 241 agggattgac ttactcactt ttcgccggc gccggttct ccggagccgc ctcaccttc
 301 ccggcagccc gagcagccgg agcagagagc cttgggtccg gtttctatgc caaaccttgt
 361 accggaggtg atcgatctta cctgccacga ggctggcttt ccacccagtg acgacgagga
 421 tgaagagggt gaggagtttg tgttagatta tgtggagcac cccgggcacg gttgcaggtc
 481 ttgtcattat caccggagga atacggggga cccagatatt atgtgttcgc tttgctatat
 541 gaggacctgt ggcatgtttg tctacagtaa gtgaaaatta tgggcagtgg gtgatagagt
 601 ggtgggtttg gtgtggtaat tttttttta atttttacag ttttgtggtt taaagaattt
 661 tgtattgtga tttttttaaa aggtcctgtg tctgaacctg agcctgagcc cgagccagaa
 721 ccggagcctg caagacctac ccgccgtcct aaaatgcgc ctgctatcct gagacgcccg
 781 acatcacctg tgtctagaga atgcaatagt agtacggata gctgtgactc cggtccttct
 841 aacacacctc ctgagataca cccggtggtc ccgctgtgcc ccattaaacc agttgccgtg
 901 agagttggtg ggcgtcgcca ggctgtggaa tgtatcgagg acttgcttaa cgagcctggg
 961 caacctttgg acttgagctg taaacgcccc aggccagcgg ccgcaaagac ctgcctgatc
1021 tgtggagatg aagcttctgg gtgtcactat ggagctctca catgtggaag ctgcaaggtc
1081 ttcttcaaaa gagccgctga agggaaacag aagtacctgt gcgccagcag aaatgattgc
1141 actattgata aattccgaag gaaaaattgt ccatcttgtc gtcttcggaa atgttatgaa
1201 gcagggatga ctctgggagc ccggaagctg aagaaacttg gtaatctgaa actacaggag
1261 gaaggagagg cttccagcac caccagcccc actgagtgac tcgag
```

Fig. 8

SEQ ID NO: 4

LOCUS    12S-AR\full\ORF 3514 bp DNA
SOURCE
ORGANISM
COMMENT   This file is created by Vector NTI
          http://www.informaxinc.com/
COMMENT   VNTDATE|268167626|
COMMENT   VNTAUTHORNAME|Ron Rodriguez|
BASE COUNT    776 a   1035 c   1008 g   695 t
ORIGIN

```
   1 accgggactg aaaatgagac atattatctg ccacggaggt gttattaccg aagaaatggc
  61 cgccagtctt ttggaccagc tgatcgaaga ggtactggct gataatcttc cacctcctag
 121 ccattttgaa ccacctaccc ttcacgaact gtatgattta gacgtgacgg cccccgaaga
 181 tcccaacgag gaggcggttt cgcagatttt tcccgactct gtaatgttgg cggtgcagga
 241 agggattgac ttactcactt ttccgccggc gcccggttct ccggagccgc ctcacctttc
 301 ccggcagccc gagcagccgg agcagagagc cttgggtccg gtttctatgc caaaccttgt
 361 accggaggtg atcgatctta cctgccacga ggctggcttt ccacccagtg acgacgagga
 421 tgaagagggt cctgtgtctg aacctgagcc tgagcccgag ccagaaccgg agcctgcaag
 481 acctacccgc cgtcctaaaa tggcgcctgc tatcctgaga cgcccgacat cacctgtgtc
 541 tagagaatgc aatagtagta cggatagctg tgactccggt ccttctaaca cacctcctga
 601 gatacacccg gtggtcccgc tgtgccccat taaaccagtt gccgtgagag ttggtgggcg
 661 tcgccagget gtggaatgta tcgaggactt gcttaacgag cctgggcaac ctttggactt
 721 gagctgtaaa cgccccaggc cagcggccgc agaagtgcag ttagggctgg aagggtcta
 781 ccctcggccg ccgtccaaga cctaccgagg agctttccag aatctgttcc agagcgtgcg
 841 cgaagtgatc cagaaccggg gccccaggca cccagaggcc gcgagcgcag cacctcccgg
 901 cgccagtttg ctgctgctgc agcagcagca gcagcagcag cagcagcagc agcagcagca
 961 gcagcagcag cagcagcagc aagagactag ccccaggcag cagcagcagc agcagggtga
1021 ggatggttct ccccaagccc atcgtagagg ccccacaggc tacctggtcc tggatgagga
1081 acagcaacct tcacagccgc agtcggccct ggagtgccac cccgagagag gttgcgtccc
1141 agagcctgga gccgcgtgg ccgccagcaa ggggctgccg cagcagctgc cagcacctcc
1201 ggacgaggat gactcagctg ccccatccac gttgtccctg ctgggcccca ctttcccegg
1261 cttaagcagc tgctccgctg accttaaaga catcctgagc gaggccagca ccatgcaact
1321 ccttcagcaa cagcagcagg aagcagtatc cgaaggcagc agcagcggga gagcgaggga
1381 ggcctcgggg gctcccactt cctccaagga caattactta gggggcactt cgaccatttc
1441 tgacaacgcc aaggagttgt gtaaggcagt gtcggtgtcc atgggcctgg gtgtggaggc
1501 gttggagcat ctgagtccag ggaacagct tcgggggggat tgcatgtacg ccccactttt
1561 gggagttcca cccgctgtgc gtcccactcc ttgtgcccca ttggccgaat gcaaaggttc
1621 tctgctagac gacagcgcag gcaagagcac tgaagatact gctgagtatt ccccttttcaa
1681 gggaggttac accaaagggc tagaaggcga gagcctaggc tgctctggca gcgctgcagc
1741 agggagctcc gggacacttg aactgccgtc taccctgtct ctctacaagt ccggagcact
1801 ggacgaggca gctgcgtacc agagtcgcga ctactacaac tttccactgg ctctggccgg
1861 accgcgccc cctccgccgc ctccccatcc ccacgctcgc atcaagctgg agaaccgct
1921 ggactacggc agcgcctggg cggctgcggc ggcgcagtgc cgctatgggg acctggcgag
1981 cctgcatggc gcgggtgcag cgggacccgg ttctgggtca ccctcagccg ccgcttcctc
2041 atcctggcac actctcttca cagccgaaga aggccagttg tatggaccgt gtggtggtgg
2101 tggggggtggt ggcggcggcg gcggcggcgg cggcggcggc ggcggcggcg gcggcggcgg
```

Fig. 9-1

```
2161 cggcgaggcg ggagctgtag cccectacgg ctacactcgg ccccctcagg ggctggcggg
2221 ccaggaaagc gacttcaccg cacctgatgt gtggtaccct ggcggcatgg tgagcagagt
2281 gccctatccc agtcccactt gtgtcaaaag cgaaatgggc ccctggatgg atagctactc
2341 cggaccttac ggggacatgc gtttggagac tgccagggac catgttttgc ccattgacta
2401 ttactttcca ccccagaaga cctgcctgat ctgtggagat gaagcttctg ggtgtcacta
2461 tggagctctc acatgtggaa gctgcaaggt cttcttcaaa agagccgctg aagggaaaca
2521 gaagtacctg tgcgccagca gaaatgattg cactattgat aaattccgaa ggaaaaattg
2581 tccatcttgt cgtcttcgga aatgttatga agcagggatg actctgggag cccggaagct
2641 gaagaaactt ggtaatctga aactacagga ggaaggagag gcttccagca ccaccagccc
2701 cactgaggag acaacccaga agctgacagt gtcacacatt gaaggctatg aatgtcagcc
2761 catctttctg aatgtcctgg aagccattga gccaggtgta gtgtgtgctg gacacgacaa
2821 caaccagccc gactcctttg cagccttgct ctctagcctc aatgaactgg gagagagaca
2881 gcttgtacac gtggtcaagt gggccaaggc cttgcctggc ttccgcaact tacacgtgga
2941 cgaccagatg gctgtcattc agtactcctg gatggggctc atggtgtttg ccatgggctg
3001 gcgatccttc accaatgtca actccaggat gctctacttc gccctgatc tggttttcaa
3061 tgagtaccgc atgcacaagt cccggatgta cagccagtgt gtccgaatga ggcacctctc
3121 tcaagagttt ggatggctcc aaatcacccc ccaggaattc ctgtgcatga aagcactgct
3181 actcttcagc attattccag tggatgggct gaaaaatcaa aaattctttg atgaacttcg
3241 aatgaactac atcaaggaac tcgatcgtat cattgcatgc aaaagaaaaa atcccacatc
3301 ctgctcaaga cgcttctacc agctcaccaa gctcctggac tccgtgcagc ctattgcgag
3361 agagctgcat cagttcactt ttgacctgct aatcaagtca cacatggtga gcgtggactt
3421 tccggaaatg atggcagaga tcatctctgt gcaagtgccc aagatccttt ctgggaaagt
2481 caagcccatc tatttccaca cccagtgact cgag
```

Fig. 9-2

SEQ ID NO: 5

LOCUS 12S-AR\TAD\ORF 2716 bp DNA
SOURCE
 ORGANISM

BASE COUNT    572 a   818 c   824 g   502 t
ORIGIN
```
   1 accgggactg aaaatgagac atattatctg ccacggaggt gttattaccg aagaaatggc
  61 cgccagtctt ttggaccagc tgatcgaaga ggtactggct gataatcttc cacctcctag
 121 ccattttgaa ccacctaccc ttcacgaact gtatgattta gacgtgacgg cccccgaaga
 181 tcccaacgag gaggcggttt cgcagatttt tcccgactct gtaatgttgg cggtgcagga
 241 agggattgac ttactcactt ttccgccggc gcccggttct ccggagccgc ctcacctttc
 301 ccggcagccc gagcagccgg agcagagagc cttgggtccg gtttctatgc caaaccttgt
 361 accggaggtg atcgatctta cctgccacga ggctggcttt ccacccagtg acgacgagga
 421 tgaagagggt cctgtgtctg aacctgagcc tgagcccgag ccagaaccgg agcctgcaag
 481 acctaccogc cgtcctaaaa tggcgcctgc tatcctgaga cgcccgacat cacctgtgtc
 541 tagagaatgc aatagtagta cggatagctg tgactccggt ccttctaaca cacctcctga
 601 gatacacccg gtggtcccgc tgtgccccat taaaccagtt gccgtgagag ttggtgggcg
 661 tcgccaggct gtggaatgta tcgaggactt gcttaacgag cctgggcaac ctttggactt
 721 gagctgtaaa cgcccaggc cagcggccgc agaagtgcag ttagggctgg aagggtcta
 781 ccctcggccg ccgtccaaga cctaccgagg agctttccag aatctgttcc agagcgtgcg
 841 cgaagtgatc cagaacccgg gccccaggca cccagaggcc gcgagcgcag cacctcccgg
 901 cgccagtttg ctgctgctgc agcagcagca gcagcagcag cagcagcagc agcagcagca
 961 gcagcagcag cagcagcagc aagagactag cccaggcag cagcagcagc agcagggtga
1021 ggatggttct ccccaagccc atcgtagagg cccacaggc tacctggtcc tggatgagga
1081 acagcaacct tcacagccgc agtcggccct ggagtgccac cccgagagag gttgcgtccc
1141 agagcctgga gccgccgtgg ccgccagcaa ggggctgccg cagcagctgc cagcacctcc
1201 ggacgaggat gactcagctg ccccatccac gttgtccctg ctgggcccca ctttccccgg
1261 cttaagcagc tgctccgctg accttaaaga catcctgagc gaggccagca ccatgcaact
1321 ccttcagcaa cagcagcagg aagcagtatc cgaaggcagc agcagcggga gagcgaggga
1381 ggcctcgggg gctcccactt cctccaagga caattactta ggggcactt cgaccatttc
1441 tgacaacgcc aaggagttgt gtaaggcagt gtcggtgtcc atgggcctgg gtgtggaggc
1501 gttggagcat ctgagtccag gggaacagct tcgggggat tgcatgtacg ccccactttt
1561 gggagttcca cccgctgtgc gtcccactcc ttgtgcccca ttggccgaat gcaaaggttc
1621 tctgctagac gacagcgcag gcaagagcac tgaagatact gctgagtatt ccccttcaa
1681 gggaggttac accaaagggc tagaaggcga gagcctaggc tgctctggca gcgctgcagc
1741 agggagctcc gggacacttg aactgccgtc taccctgtct ctctacaagt ccggagcact
1801 ggacgaggca gctgcgtacc agagtcgcga ctactacaac tttccactgg ctctggccgg
1861 accgccgccc cctccgccgc ctccccatcc ccacgctcgc atcaagctgg agaaccgct
1921 ggactacggc agcgcctggg cggctgcggc ggcgcagtgc cgctatgggg acctggcgag
1981 cctgcatggc gcgggtgcag cgggacccgg ttctgggtca ccctcagccg ccgcttcctc
2041 atcctggcac actctcttca cagccgaaga aggccagttg tatggaccgt gtggtggtgg
2101 tgggggtggt ggcggcggcg gcggcggcgg cggcggcggc ggcggcggcg gcggcggcgg
```

Fig. 10-1

```
2161 cggcgaggcg ggagctgtag cccccctacgg ctacactcgg ccccctcagg ggctggcggg
2221 ccaggaaagc gacttcaccg cacctgatgt gtggtaccct ggcggcatgg tgagcagagt
2281 gccctatccc agtcccactt gtgtcaaaag cgaaatgggc ccctggatgg atagctactc
2341 cggaccttac ggggacatgc gtttggagac tgccagggac catgtttttgc ccattgacta
2401 ttactttcca ccccagaaga cctgcctgat ctgtggagat gaagcttctg ggtgtcacta
2461 tggagctctc acatgtggaa gctgcaaggt cttcttcaaa agagccgctg aagggaaaca
2521 gaagtacctg tgcgccagca gaaatgattg cactattgat aaattccgaa ggaaaaattg
2581 tccatcttgt cgtcttcgga aatgttatga agcagggatg actctgggag cccggaagct
2641 gaagaaactt ggtaatctga aactacagga ggaaggagag gcttccagca ccaccagccc
2701 cactgagtga ctcgag
```

Fig. 10-2

SEQ ID NO: 6

LOCUS   12S-DBD\ORF 1051 bp  DNA
SOURCE
 ORGANISM
COMMENT   This file is created by Vector NTI
       http://www.informaxinc.com/
COMMENT   VNTDATE|268064542|
COMMENT   VNTAUTHORNAME|Ron Rodriguez|
BASE COUNT     251 a    284 c    287 g    229 t
ORIGIN

```
   1 accgggactg aaaatgagac atattatctg ccacggaggt gttattaccg aagaaatggc
  61 cgccagtctt ttggaccagc tgatcgaaga ggtactggct gataatcttc cacctcctag
 121 ccattttgaa ccacctaccc ttcacgaact gtatgattta gacgtgacgg ccccgaaga
 181 tcccaacgag gaggcggttt cgcagatttt tcccgactct gtaatgttgg cggtgcagga
 241 agggattgac ttactcactt ttccgccggc gcccggttct ccggagccgc ctcacctttc
 301 ccggcagccc gagcagccgg agcagagagc cttgggtccg gtttctatgc caaaccttgt
 361 accggaggtg atcgatctta cctgccacga ggctggcttt ccacccagtg acgacgagga
 421 tgaagagggt cctgtgtctg aacctgagcc tgagcccgag ccagaaccgg agcctgcaag
 481 acctacccgc cgtcctaaaa tggcgcctgc tatcctgaga cgcccgacat cacctgtgtc
 541 tagagaatgc aatagtagta cggatagctg tgactccggt ccttctaaca cacctcctga
 601 gatacacccg gtggtcccgc tgtgccccat taaaccagtt gccgtgagag ttggtgggcg
 661 tcgccaggct gtggaatgta tcgaggactt gcttaacgag cctgggcaac ctttggactt
 721 gagctgtaaa cgccccaggc cagcggccgc aaagacctgc ctgatctgtg gagatgaagc
 781 ttctgggtgt cactatggag ctctcacatg tggaagctgc aaggtcttct tcaaaagagc
 841 cgctgaaggg aaacagaagt acctgtgcgc cagcagaaat gattgcacta ttgataaatt
 901 ccgaaggaaa aattgtccat cttgtcgtct tcggaaatgt tatgaagcag ggatgactct
 961 gggagcccgg aagctgaaga aacttggtaa tctgaaacta caggaggaag gagaggcttc
1021 cagcaccacc agccccactg agtgactcga g
```

Fig. 11

12S-AR FULL-LENGTH mrhiichggviteemaaslldqlieevladnlpppshfepptlhelydldvtapedpneeav
sqifpdsvmlavqegidlltfppapgspepphlsrqpeqpeqralgpvsmpnlvpevidlt
cheagfppsddedeegpvsepepepepepeparptrrpkmapailrrptspvsrecnsstd
scdsgpsntppeihpvvplcpikpvavrvggrrqaveciedllnepgqpldlsckrprpaaa
evqlglgrvyprppsktyrgafqnlfqsvreviqnpgprhpeaasaappgaslllllqqqqqq
qqqqqqqqqqqqqqetsprqqqqqqgedgspqahrrgptgylvldeeqqpsqpqsal
echpergcvpepgaavaaskglpqqlpappdeddsaapstlsllgptfpglsscsadlkdils
eastmqllqqqqqeavsegsssgrareasgaptsskdnylggtstisdnakelckavsvsm
glgvealehlspgeqlrgdcmyapllgvppavrptpcaplaeckgsllddsagkstedtaey
spfkggytkglegeslgcsgsaaagaagtlelpstlslyksgaldeaaayqsrdyynfplala
gppppppphphariklenpldygsawaaaaaqcrygdlaslhgagaagpgsgspsaaas
sswhtlftaeegqlygpcgggggggggggggggggggggggggeagavapygytrppq
glagqesdftapdvwypggmvsrvpypsptcvksemgpwmdsysgpygdmrletar
dhvlpidyyfppqktclicgdeasgchygaltcgsckvffkraaegkqkylcasrndctidk
frrkncpscrlrkcyeagmtlgarklkklgnlklqeegeassttspteettqkltvshiegye
cqpiflnvleaiepgvvcaghdnnqpdsfaallsslnelgerqlvhvvkwakalpgfrnlhvd
dqmaviqyswmglmvfamgwrsftnvnsrmlyfapdlvfneyrmhksrmysqcvr
mrhlsqefgwlqitpqeflcmkalllfsiipvdglknqkffdelrmnyikeldriiackrknp
tscsrrfyqltklldsvqpiarelhqftfdllikshmvsvdfpemmaeiisvqvpkilsgkvk
piyfhtq

Fig. 12

SEQ ID NO: 8

12S-AR TAD mrhiichggviteemaaslldqlieevladnlpppshfepptlhelydldvtapedpneeav
sqifpdsvmlavqegidlltfppapgspepphlsrqpeqpeqralgpvsmpnlvpevidlt
cheagfppsddedeegpvsepepepepepepeparptrrpkmapailrrptspvsrecnsstd
scdsgpsntppeihpvvplcpikpvavrvggrrqaveciedllnepgqpldlsckrprpaaa
evqlglgrvyprppsktyrgafqnlfqsvreviqnpgprhpeaasaappgaslllqqqqqq
qqqqqqqqqqqqqqetsprqqqqqqgedgspqahrrgptgylvldeeqqpsqpqsal
echpergcvpepgaavaaskglpqqlpappdeddsaapstlsllgptfpglsscsadlkdils
eastmqllqqqqqeavsegsssgrareasgaptsskdnylggtstisdnakelckavsvsm
glgvealehlspgeqlrgdcmyapllgvppavrptpcaplaeckgsllddsagkstedtaey
spfkggytkglegeslgcsgsaaagssgtlelpstlslyksgaldeaaayqsrdyynfplala
gpppppppphphariklenpldygsawaaaaaqcrygdlaslhgagaagpgsgspsaaas
sswhtlftaeegqlygpcggggggggggggggggggggggeagavapygytrppq
glagqesdftapdvwypggmvsrvpypsptcvksemgpwmdsysgpygdmrletar
dhvlpidyyfppqktclicgdeasgchygaltcgsckvffkraaegkqkylcasrndctidk
frrkncpscrlrkcyeagmtlgarklkklgnlklqeegeassttspte

Fig. 13

SEQ ID NO: 9

12S-AR-DBD mrhiichggviteemaaslldqlieevladnlpppshfepptlhelydldvtapedpneeav
sqifpdsvmlavqegidlltfppapgspepphlsrqpeqpeqralgpvsmpnlvpevidlt
cheagfppsddedeegpvsepepepepepeparptrrpkmapailrrptspvsrecnsstd
scdsgpsntppeihpvvplcpikpvavrvggrrqaveciedllnepgqpldlsckrprpaaa
ktclicgdeasgchygaltcgsckvffkraaegkqkylcasrndctidkfrrkncpscrlrkc
yeagmtlgarklkklgnlklqeegeassttspte

Fig. 14

SEQ ID NO: 10

E1A atgagacatattatctgccacggaggtgttattaccgaagaaatggccgccagtct
tttggaccagctgatcgaagaggtactggctgataatcttccacctcctagccatt
ttgaaccacctacccttcacgaactgtatgatttagacgtgacggcccccgaagat
cccaacgaggaggcggtttcgcagattttccccgactctgtaatgttggcggtgca
ggaagggattgacttactcacttttccgccggcgcccggttctccggagccgcctc
acctttcccggcagcccgagcagccggagcagagagccttgggtccggtttctatg
ccaaaccttgtaccggaggtgatcgatcttacctgccacgaggctggctttccacc
cagtgacgacgaggatgaagagggtgaggagtttgtgttagattatgtggagcacc
ccgggcacggttgcaggtcttgtcattatcaccggaggaatacgggggacccagat
attatgtgttcgctttgctatatgaggacctgtggcatgtttgtctacagtaagtg
aaaattatgggcagtgggtgatagagtggtgggtttggtgtggtaattttttttt
aattttacagttttgtggtttaaagaatttgtattgtgatttttttaaaaggtc
ctgtgtctgaacctgagcctgagcccgagccagaaccggagcctgcaagacctacc
cgccgtcctaaaatggcgcctgctatcctgagacgcccgacatcacctgtgtctag
agaatgcaatagtagtacggatagctgtgactccggtccttctaacacacctcctg
agatacaccggtggtcccgctgtgccccattaaaccagttgccgtgagagttggt
gggcgtcgccaggctgtggaatgtatcgaggacttgcttaacgagcctgggcaacc
tttggacttgagctgtaaacgcccaggccataa

Fig. 16

SEQ ID NO. 11

E1A_TAD atgagacatattatctgccacggaggtgttattaccgaagaaatggccgccagtct
tttggaccagctgatcgaagaggtactggctgataatcttccacctcctagccatt
ttgaaccacctacccttcacgaactgtatgatttagacgtgacggcccccgaagat
cccaacgaggaggcggtttcgcagattttccccgactctgtaatgttggcggtgca
ggaagggattgacttactcacttttccgccggcgcccggttctccggagccgcctc
acctttcccggcagcccgagcagccggagcagagagccttgggtccggtttctatg
ccaaaccttgtaccggaggtgatcgatcttacctgccacgaggctggctttccacc
cagtgacgacgaggatgaagagggtgaggagtttgtgttagattatgtggagcacc
ccgggcacggttgcaggtcttgtcattatcaccggaggaatacgggggacccagat
attatgtgttcgctttgctatatgaggacctgtggcatgtttgtctacagtaagtg
aaaattatgggcagtgggtgatagagtggtgggtttggtgtggtaatttttttttt
aattttacagttttgtggtttaaagaatttgtattgtgatttttttaaaaggtc
ctgtgtctgaacctgagcctgagcccgagccagaaccggagcctgcaagacctacc
cgccgtcctaaaatggcgcctgctatcctgagacgcccgacatcacctgtgtctag
agaatgcaatagtagtacggatagctgtgactccggtccttctaacacacctcctg
agatacacccggtggtcccgctgtgcccattaaaccagttgccgtgagagttggt
gggcgtcgccaggctgtggaatgtatcgaggacttgcttaacgagcctgggcaacc
tttggacttgagctgtaaacgccccaggccataa

Fig. 17

SEQ ID NO. 12

E1A_AR atgagacatattatctgccacggaggtgttattaccgaagaaatggccgccagtct
tttggaccagctgatcgaagaggtactggctgataatcttccacctcctagccatt
ttgaaccacctacccttcacgaactgtatgatttagacgtgacggcccccgaagat
cccaacgaggaggcggtttcgcagattttcccgactctgtaatgttggcggtgca
ggaagggattgacttactcacttttccgccggcgcccggttctccggagccgctc
acctttcccggcagcccgagcagccggagcagagagccttgggtccggtttctatg
ccaaaccttgtaccggaggtgatcgatcttacctgccacgaggctggctttccacc
cagtgacgacgaggatgaagagggtgaggagtttgtgttagattatgtggagcacc
ccgggcacggttgcaggtcttgtcattatcaccggaggaatacgggggacccagat
attatgtgttcgctttgctatatgaggacctgtggcatgtttgtctacagtaagtg
aaaattatgggcagtgggtgatagagtggtgggtttggtgtggtaattttttttt
aattttacagttttgtggtttaaagaatttgtattgtgatttttttaaaaggtc
ctgtgtctgaacctgagcctgagcccgagccagaaccggagcctgcaagacctacc
cgccgtcctaaaatggcgcctgctatcctgagacgcccgacatcacctgtgtctag
agaatgcaatagtagtacggatagctgtgactccggtccttctaacacacctcctg
agatacacccggtggtcccgctgtgccccattaaaccagttgccgtgagagttggt
gggcgtcgccaggctgtggaatgtatcgaggacttgcttaacgagcctgggcaacc
tttggacttgagctgtaaacgcccaggccataagcggccgcagaagtgcagttag
ggctgggaagggtc

Fig. 18

SEQ ID NO. 13

E1A_AR_C685Y atgagacatattatctgccacggaggtgttattaccgaagaaatggccgccagtct
tttggaccagctgatcgaagaggtactggctgataatcttccacctcctagccatt
ttgaaccacctaccttcacgaactgtatgatttagacgtgacggcccccgaagat
cccaacgaggaggcggtttcgcagattttcccgactctgtaatgttggcggtgca
ggaagggattgacttactcacttttccgccggcgcccggttctccggagccgcctc
acctttcccggcagcccgagcagccggagcagagagccttgggtccggtttctatg
ccaaaccttgtaccggaggtgatcgatcttacctgccacgaggctggctttccacc
cagtgacgacgaggatgaagagggtgaggagtttgtgttagattatgtggagcacc
ccgggcacggttgcaggtcttgtcattatcaccggaggaatacgggggacccagat
attatgtgttcgctttgctatatgaggacctgtggcatgtttgtctacagtaagtg
aaaattatgggcagtgggtgatagagtggtgggtttggtgtggtaattttttttt
aattttacagttttgtggtttaaagaattttgtattgtgatttttttaaaaggtc
ctgtgtctgaacctgagcctgagcccgagccagaaccggagcctgcaagacctacc
cgccgtcctaaaatggcgcctgctatcctgagacgcccgacatcacctgtgtctag
agaatgcaatagtagtacggatagctgtgactccggtccttctaacacacctcctg
agatacacccggtggtcccgctgtgccccattaaaccagttgccgtgagagttggt
gggcgtcgccaggctgtggaatgtatcgaggacttgcttaacgagcctgggcaacc
tttggacttgagctgtaaacgccccaggccataagcggccgcagaagtgcagttag
ggctgggaagggtc

Fig. 19

SEQUENCE LISTING

<160> NUMBER OF SEQ ID NOS: 22

<210> SEQ ID NO 1
<211> LENGTH: 3768
<212> TYPE: DNA
<213> ORGANISM: Artificial Sequence
<220> FEATURE:
<223> OTHER INFORMATION: Description of Artificial Sequence: Synthetic
      nucleotide sequence construct EA1/AR

<400> SEQUENCE: 1

```
accgggactg aaaatgagac atattatctg ccacggaggt gttattaccg aagaaatggc      60
cgccagtctt ttggaccagc tgatcgaaga ggtactggct gataatcttc cacctcctag     120
ccattttgaa ccacctaccc ttcacgaact gtatgattta gacgtgacgg ccccgaaga     180 tcccaacgag gaggcggttt cgcagatttt tcccgactct gtaatgttgg cggtgcagga    240
agggattgac ttactcactt ttccgccggc gcccggttct ccggagccgc ctcaccttc    300 ccggcagccc gagcagccgg agcagagagc cttgggtccg gtttctatgc caaaccttgt    360
accggaggtg atcgatctta cctgccacga ggctggcttt ccacccagtg acgacgagga    420
tgaagagggt gaggagtttg tgttagatta tgtggagcac cccgggcacg gttgcaggtc    480
ttgtcattat caccggagga atacggggga cccagatatt atgtgttcgc tttgctatat    540
gaggacctgt ggcatgtttg tctacagtaa gtgaaaatta tgggcagtgg gtgatagagt    600
ggtgggtttg tgtgtggtaat ttttttttta atttttacag ttttgtggtt taaagaattt    660
tgtattgtga ttttttttaaa aggtcctgtg tctgaacctg agcctgagcc cgagccagaa    720
ccggagcctg caagacctac ccgccgtcct aaaatggcgc ctgctatcct gagacgcccg    780
acatcacctg tgtctagaga atgcaatagt agtacggata gctgtgactc cggtccttct    840
aacacacctc ctgagataca cccggtggtc ccgctgtgcc ccattaaacc agttgccgtg    900
agagttggtg ggcgtcgcca ggctgtggaa tgtatcgagg acttgcttaa cgagcctggg    960
caacctttgg acttgagctg taaacgcccc aggccagcgg ccgcagaagt gcagttaggg    1020
ctgggaaggg tctaccctcg gccgccgtcc aagacctacc gaggagcttt ccagaatctg    1080
ttccagagcg tgcgcgaagt gatccagaac ccgggcccca ggcacccaga ggccgcgagc    1140
gcagcacctc ccggcgccag tttgctgctg ctgcagcagc agcagcagca gcagcagcag    1200
cagcagcagc agcagcagca gcagcagcag cagcaagaga ctagccccag gcagcagcag    1260
cagcagcagg gtgaggatgg ttctccccaa gcccatcgta gaggccccac aggctacctg    1320
gtcctggatg aggaacagca accttcacag ccgcagtcgg ccctggagtg ccaccccgag    1380
agaggttgcg tcccagagcc tggagccgcc gtggccgcca gcaagggct gccgcagcag    1440 ctgccagcac ctccggacga ggatgactca gctgccccat ccacgttgtc cctgctgggc    1500
cccactttcc ccggcttaag cagctgctcc gctgaccttg aagacatcct gagcgaggcc    1560
agcaccatgc aactccttca gcaacagcag caggaagcag tatccgaagg cagcagcagc    1620
gggagagcga gggaggcctc ggggctcccc acttcctcca aggacaatta cttagggggc    1680
acttcgacca tttctgacaa cgccaaggag ttgtgtaagg cagtgtcggt gtccatgggc    1740
ctgggtgtgg aggcgttgga gcatctgagt ccaggggaac agcttcgggg ggattgcatg    1800
tacgccccac ttttgggagt tccacccgct gtgcgtccca ctccttgtgc cccattggcc    1860
gaatgcaaag gttctctgct agacgacagc gcaggcaaga gcactgaaga tactgctgag    1920
```

-continued

```
tattcccctt tcaagggagg ttacaccaaa gggctagaag gcgagagcct aggctgctct    1980
ggcagcgctg cagcagggag ctccgggaca cttgaactgc cgtctaccct gtctctctac    2040
aagtccggag cactggacga ggcagctgcg taccagagtc gcgactacta caactttcca    2100
ctggctctgg ccggaccgcc gccccctccg ccgcctcccc atcccacgc tcgcatcaag     2160 ctggagaacc cgctggacta cggcagcgcc tgggcggctg cggcggcgca gtgccgctat    2220
ggggacctgg cgagcctgca tggcgcgggt gcagcggacc ccggttctgg gtcaccctca    2280
gccgccgctt cctcatcctg gcacactctc ttcacagccg aagaaggcca gttgtatgga    2340
ccgtgtggtg gtggtgggg tggtggcggc ggcggcggcg gcggcggcgg cggcggcggc     2400
ggcggcggcg gcggcggcga ggcgggagct gtagccccct acggctacac tcggcccct    2460 caggggctgg cgggccagga aagcgacttc accgcacctg atgtgtggta ccctggcggc    2520
atggtgagca gagtgcccta tcccagtccc acttgtgtca aaagcgaaat gggcccctgg    2580
atggatagct actccggacc ttacggggac atgcgtttgg agactgccag ggaccatgtt    2640
ttgcccattg actattactt tccaccccag aagacctgcc tgatctgtgg agatgaagct    2700
tctgggtgtc actatggagc tctcacatgt ggaagctgca aggtcttctt caaaagagcc    2760
gctgaaggga acagaagta cctgtgcgcc agcagaaatg attgcactat tgataaattc    2820
cgaaggaaaa attgtccatc ttgtcgtctt cggaaatgtt atgaagcagg gatgactctg    2880
ggagcccgga agctgaagaa acttggtaat ctgaaactac aggaggaagg agaggcttcc    2940
agcaccacca gccccactga ggagacaacc cagaagctga cagtgtcaca cattgaaggc    3000
tatgaatgtc agcccatctt tctgaatgtc ctggaagcca ttgagccagg tgtagtgtgt    3060
gctggacacg acaacaacca gcccgactcc tttgcagcct tgctctctag cctcaatgaa    3120
ctgggagaga gacagcttgt acacgtggtc aagtgggcca aggccttgcc tggcttccgc    3180
aacttacacg tggacgacca gatggctgtc attcagtact cctggatggg gctcatggtg    3240
tttgccatgg gctggcgatc cttcaccaat gtcaactcca ggatgctcta cttcgcccct    3300
gatctggttt tcaatgagta ccgcatgcac aagtcccgga tgtacagcca gtgtgtccga    3360
atgaggcacc tctctcaaga gtttggatgg ctccaaatca ccccccagga attcctgtgc    3420
atgaaagcac tgctactctt cagcattatt ccagtggatg ggctgaaaaa tcaaaaattc    3480
tttgatgaac ttcgaatgaa ctacatcaag gaactcgatc gtatcattgc atgcaaagaa    3540
aaaaatccca catcctgctc aagacgcttc taccagctca ccaagctcct ggactccgtg    3600
cagcctattg cgagagagct gcatcagttc actttttgacc tgctaatcaa gtcacacatg    3660
gtgagcgtgg actttccgga aatgatggca gagatcatct ctgtgcaagt gcccaagatc    3720
ctttctggga aagtcaagcc catctatttc cacacccagt gactcgag                  3768
```

<210> SEQ ID NO 2
<211> LENGTH: 2970
<212> TYPE: DNA
<213> ORGANISM: Artificial Sequence
<220> FEATURE:
<223> OTHER INFORMATION: Description of Artificial Sequence: Synthetic nucleotide sequence construct EA1/TAD

<400> SEQUENCE: 2

```
accgggactg aaaatgagac atattatctg ccacggaggt gttattaccg aagaaatggc      60
cgccagtctt ttggaccagc tgatcgaaga ggtactggct gataatcttc cacctcctag     120
ccattttgaa ccacctaccc ttcacgaact gtatgattta gacgtgacgg cccccgaaga    180
```

-continued

```
tcccaacgag gaggcggttt cgcagatttt tcccgactct gtaatgttgg cggtgcagga      240
agggattgac ttactcactt ttccgccggc gcccggttct ccggagccgc ctcacctttc      300
ccggcagccc gagcagccgg agcagagagc cttgggtccg gtttctatgc caaaccttgt      360
accggaggtg atcgatctta cctgccacga ggctggcttt ccacccagtg acgacgagga      420
tgaagagggt gaggagtttg tgttagatta tgtggagcac cccgggcacg gttgcaggtc      480
ttgtcattat caccggagga atacgggga cccagatatt atgtgttcgc tttgctatat       540
gaggacctgt ggcatgtttg tctacagtaa gtgaaaatta tgggcagtgg gtgatagagt      600
ggtgggtttg gtgtggtaat tttttttta attttacag ttttgtggtt taaagaattt        660
tgtattgtga ttttttaaa aggtcctgtg tctgaacctg agcctgagcc cgagccagaa       720
ccggagcctg caagacctac ccgccgtcct aaaatggcgc ctgctatcct gagacgcccg      780
acatcacctg tgtctagaga atgcaatagt agtacggata gctgtgactc cggtccttct      840
aacacacctc ctgagataca cccggtggtc ccgctgtgcc ccattaaacc agttgccgtg      900
agagttggtg ggcgtcgcca ggctgtggaa tgtatcgagg acttgcttaa cgagcctggg      960
caacctttgg acttgagctg taaacgcccc aggccagcgg ccgcagaagt gcagttaggg     1020
ctgggaaggg tctaccctcg gccgccgtcc aagacctacc gaggagcttt ccagaatctg     1080
ttccagagcg tgcgcgaagt gatccagaac ccgggcccca ggcacccaga ggccgcgagc     1140
gcagcacctc ccggcgccag tttgctgctg ctgcagcagc agcagcagca gcagcagcag     1200
cagcagcagc agcagcagca gcagcagcag cagcaagaga ctagccccag gcagcagcag     1260
cagcagcagg gtgaggatgg ttctccccaa gcccatcgta gaggccccac aggctacctg     1320
gtcctggatg aggaacagca accttcacag ccgcagtcgg ccctggagtg ccaccccgag     1380
agaggttgcg tcccagagcc tggagccgcc gtggccgcca gcaaggggct gccgcagcag     1440
ctgccagcac ctccggacga ggatgactca gctgccccat ccacgttgtc cctgctgggc     1500
cccactttcc ccggcttaag cagctgctcc gctgacctta agacatcct gagcgaggcc      1560 agcaccatgc aactccttca gcaacagcag caggaagcag tatccgaagg cagcagcagc     1620
gggagagcga gggaggcctc gggggctccc acttcctcca aggacaatta cttaggggc      1680 acttcgacca tttctgacaa cgccaaggag ttgtgtaagg cagtgtcggt gtccatgggc     1740
ctgggtgtgg aggcgttgga gcatctgagt ccaggggaac agcttcgggg ggattgcatg     1800
tacgccccac ttttgggagt tccacccgct gtgcgtccca ctccttgtgc cccattggcc     1860
gaatgcaaag gttctctgct agacgacagc gcaggcaaga gcactgaaga tactgctgag     1920
tattcccctt tcaagggagg ttacaccaaa gggctagaag gcgagagcct aggctgctct     1980
ggcagcgctg cagcagggag ctccgggaca cttgaactgc cgtctaccct gtctctctac     2040
aagtccggag cactggacga ggcagctgcg taccagagtc gcgactacta caactttcca     2100
ctggctctgg ccgaccgcc gccccctccg ccgcctcccc atcccacgc tcgcatcaag       2160 ctggagaacc cgctggacta cggcagcgcc tgggcggctg cggcggcgca gtgccgctat     2220
ggggacctgc cgagcctgca tgcgcgggt gcagcgggac ccggttctgg gtcaccctca     2280
gccgccgctt cctcatcctg cacactctc ttcacagccg aagaaggcca gttgtatgga     2340
ccgtgtggtg gtgtggggg tggtggcggc ggcggcggcg gcggcggcgg cggcggcggc     2400
ggcgcggccg gcggcggcga ggcgggagct gtagcccct acggctacac tcggccccct     2460 cagggggctgg cgggccagga aagcgacttc accgcacctg atgtgtggta ccctggcggc     2520
atggtgagca gagtgcccta tcccagtccc acttgtgtca aaagcgaaat gggcccctgg     2580
```

-continued

```
atggatagct actccggacc ttacggggac atgcgtttgg agactgccag ggaccatgtt      2640
ttgcccattg actattactt tccaccccag aagacctgcc tgatctgtgg agatgaagct      2700
tctgggtgtc actatggagc tctcacatgt ggaagctgca aggtcttctt caaaagagcc      2760
gctgaaggga aacagaagta cctgtgcgcc agcagaaatg attgcactat tgataaattc      2820
cgaaggaaaa attgtccatc ttgtcgtctt cggaaatgtt atgaagcagg gatgactctg      2880
ggagcccgga agctgaagaa acttggtaat ctgaaactac aggaggaagg agaggcttcc      2940
agcaccacca gccccactga gtgactcgag                                       2970
```

<210> SEQ ID NO 3
<211> LENGTH: 1305
<212> TYPE: DNA
<213> ORGANISM: Artificial Sequence
<220> FEATURE:
<223> OTHER INFORMATION: Description of Artificial Sequence: Synthetic
      nucleotide sequence construct EA1/DBD

<400> SEQUENCE: 3

```
accgggactg aaaatgagac atattatctg ccacggaggt gttattaccg aagaaatggc       60
cgccagtctt ttggaccagc tgatcgaaga ggtactggct gataatcttc cacctcctag      120
ccattttgaa ccacctaccc ttcacgaact gtatgattta gacgtgacgg ccccgaaga       180 tcccaacgag gaggcggttt cgcagatttt tcccgactct gtaatgttgg cggtgcagga      240
agggattgac ttactcactt ttccgccggc gcccggttct ccggagccgc ctcacctttc      300
ccggcagccc gagcagccgg agcagagagc cttgggtccg gtttctatgc caaaccttgt      360
accggaggtg atcgatctta cctgccacga ggctggcttt ccacccagtg acgacgagga      420
tgaagagggt gaggagtttg tgttagatta tgtggagcac cccgggcacg gttgcaggtc      480
ttgtcattat caccggagga atacggggga cccagatatt atgtgttcgc tttgctatat      540
gaggacctgt ggcatgtttg tctacagtaa gtgaaaatta tgggcagtgg gtgatagagt      600
ggtgggtttg gtgtggtaat tttttttta atttttacag ttttgtggtt taaagaattt      660
tgtattgtga ttttttttaaa aggtcctgtg tctgaacctg agcctgagcc cgagccagaa      720
ccggagcctg caagacctac ccgccgtcct aaaatggcgc ctgctatcct gagacgcccg      780
acatcacctg tgtctagaga atgcaatagt agtacggata gctgtgactc cggtccttct      840
aacacacctc ctgagataca cccggtggtc ccgctgtgcc ccattaaacc agttgccgtg      900
agagttggtg ggcgtcgcca ggctgtggaa tgtatcgagg acttgcttaa cgagcctggg      960
caacctttgg acttgagctg taaacgcccc aggccagcgg ccgcaaagac ctgcctgatc     1020
tgtggagatg aagcttctgg gtgtcactat ggagctctca catgtggaag ctgcaaggtc     1080
ttcttcaaaa gagccgctga agggaaacag aagtacctgt gcgccagcag aaatgattgc     1140
actattgata aattccgaag gaaaattgt ccatcttgtc gtcttcggaa atgttatgaa      1200
gcagggatga ctctgggagc ccggaagctg aagaacttg gtaatctgaa actacaggag     1260
gaaggagagg cttccagcac caccagcccc actgagtgac tcgag                      1305
```

<210> SEQ ID NO 4
<211> LENGTH: 3514
<212> TYPE: DNA
<213> ORGANISM: Artificial Sequence
<220> FEATURE:
<223> OTHER INFORMATION: Description of Artificial Sequence: Synthetic
      nucleotide sequence construct 12S/AR -continued

<400> SEQUENCE: 4

```
accgggactg aaaatgagac atattatctg ccacggaggt gttattaccg aagaaatggc    60
cgccagtctt ttggaccagc tgatcgaaga ggtactggct gataatcttc cacctcctag   120
ccattttgaa ccacctaccc ttcacgaact gtatgattta cacgtgacgg cccccgaaga   180
tcccaacgag gaggcggttt cgcagatttt tcccgactct gtaatgttgg cggtgcagga   240
agggattgac ttactcactt ttccgccggc gcccggttct ccggagccgc ctcacctttc   300
ccggcagccc gagcagccgg agcagagagc cttgggtccg gtttctatgc caaaccttgt   360
accggaggtg atcgatctta cctgccacga ggctggcttt ccacccagtg acgacgagga   420
tgaagagggt cctgtgtctg aacctgagcc tgagcccgag ccagaaccgg agcctgcaag   480
acctacccgc cgtcctaaaa tggcgcctgc tatcctgaga cgcccgacat cacctgtgtc   540
tagagaatgc aatagtagta cggatagctg tgactccggt ccttctaaca cacctcctga   600
gatacacccg gtggtcccgc tgtgcccat taaaccagtt gccgtgagag ttggtgggcg    660
tcgccaggct gtggaatgta tcgaggactt gcttaacgag cctgggcaac ctttggactt   720
gagctgtaaa cgccccaggc cagcggccga agaagtgcag ttagggctgg aagggtcta    780
ccctcggccg ccgtccaaga cctaccgagg agctttccag aatctgttcc agagcgtgcg   840
cgaagtgatc cagaacccgg gccccaggca cccagaggcc gcgagcgcag cacctcccgg   900
cgccagtttg ctgctgctgc agcagcagca gcagcagcag cagcagcagc agcagcagca   960
gcagcagcag cagcagcagc aagagactag ccccaggcag cagcagcagc agcagggtga  1020
ggatggttct ccccaagccc atcgtagagg ccccacaggc tacctggtcc tggatgagga  1080
acagcaacct tcacagccgc agtcggccct ggagtgccac cccgagagag ttgcgtccc    1140
agagcctgga gccgccgtgg ccgccagcaa ggggctgccg cagcagctgc cagcacctcc  1200
ggacgaggat gactcagctg ccccatccac gttgtccctg ctgggcccca ctttccccgg  1260
cttaagcagc tgctccgctg accttaaaga catcctgagc gaggccagca ccatgcaact  1320
ccttcagcaa cagcagcagg aagcagtatc cgaaggcagc agcagcggga gagcgaggga  1380
ggcctcgggg gctcccactt cctccaagga caattactta ggggggcactt cgaccatttc  1440
tgacaacgcc aaggagttgt gtaaggcagt gtcggtgtcc atgggcctgg gtgtggaggc  1500
gttggagcat ctgagtccag ggaacagct tcggggggat tgcatgtacg ccccactttt   1560
gggagttcca cccgctgtgc gtcccactcc ttgtgcccca ttggccgaat gcaaaggttc  1620
tctgctagac gacagcgcag gcaagagcac tgaagatact gctgagtatt cccctttcaa  1680
gggaggttac accaaagggc tagaaggcga gagcctaggc tgctctggca gcgctgcagc  1740
agggagctcc gggacacttg aactgccgtc taccctgtct ctctacaagt ccggagcact  1800
ggacgaggca gctgcgtacc agagtcgcga ctactacaac tttccactgg ctctggccgg  1860
accgccgccc cctccgccgc ctccccatcc ccacgctcgc atcaagctgg agaaccgct   1920
ggactacggc agcgcctggg cggctgcggc ggcgcagtgc cgctatgggg acctggcgag  1980
cctgcatggc gcgggtgcag cgggaccgg ttctgggtca ccctcagccg ccgcttcctc   2040
atcctggcac actctcttca cagccgaaga aggccagttg tatggaccgt gtggtggtgg  2100
tgggggtggt ggcggcggcg gcggcggcg cggcggcgg ggcggcggcg gcggcggcg    2160
cggcgaggcg ggagctgtag ccccctacgg ctacactcgg ccccctcagg ggctggcggg  2220
ccaggaaagc gacttcaccg cacctgatgt gtggtaccct ggcggcatgg tgagcagagt  2280
gccctatccc agtcccactt gtgtcaaaag cgaaatgggc ccctggatgg atagctactc  2340
```

| | |
|---|---|
| cggaccttac ggggacatgc gtttggagac tgccagggac catgttttgc ccattgacta | 2400 |
| ttactttcca ccccagaaga cctgcctgat ctgtggagat gaagcttctg ggtgtcacta | 2460 |
| tggagctctc acatgtggaa gctgcaaggt cttcttcaaa agagccgctg aagggaaaca | 2520 |
| gaagtacctg tgcgccagca gaaatgattg cactattgat aaattccgaa ggaaaaattg | 2580 |
| tccatcttgt cgtcttcgga atgttatga agcagggatg actctgggag cccgaaagct | 2640 |
| gaagaaactt ggtaatctga actacagga ggaaggagag cttccagca ccaccagccc | 2700 |
| cactgaggag acaacccaga agctgacagt gtcacacatt gaaggctatg aatgtcagcc | 2760 |
| catctttctg aatgtcctgg aagccattga gccaggtgta gtgtgtgctg acacgacaa | 2820 |
| caaccagccc gactcctttg cagccttgct ctctagcctc aatgaactgg gagagagaca | 2880 |
| gcttgtacac gtggtcaagt gggccaaggc cttgcctggc ttccgcaact acacgtgga | 2940 |
| cgaccagatg gctgtcattc agtactcctg gatgggctc atggtgtttg ccatgggctg | 3000 |
| gcgatccttc accaatgtca actccaggat gctctacttc gcccctgatc tggttttcaa | 3060 |
| tgagtaccgc atgcacaagt cccggatgta cagccagtgt gtccgaatga ggcacctctc | 3120 |
| tcaagagttt ggatggctcc aaatcacccc caggaattc ctgtgcatga agcactgct | 3180 |
| actcttcagc attattccag tggatgggct gaaaaatcaa aaattctttg atgaacttcg | 3240 |
| aatgaactac atcaaggaac tcgatcgtat cattgcatgc aaaagaaaaa atcccacatc | 3300 |
| ctgctcaaga cgcttctacc agctcaccaa gctcctggac tccgtgcagc ctattgcgag | 3360 |
| agagctgcat cagttcactt ttgacctgct aatcaagtca cacatggtga gcgtggactt | 3420 |
| tccggaaatg atggcagaga tcatctctgt gcaagtgccc aagatccttt ctgggaaagt | 3480 |
| caagcccatc tatttccaca cccagtgact cgag | 3514 |

<210> SEQ ID NO 5
<211> LENGTH: 2716
<212> TYPE: DNA
<213> ORGANISM: Artificial Sequence
<220> FEATURE:
<223> OTHER INFORMATION: Description of Artificial Sequence: Synthetic nucleotide sequence construct 12S/TAD

<400> SEQUENCE: 5

| | |
|---|---|
| accgggactg aaaatgagac atattatctg ccacggaggt gttattaccg aagaaatggc | 60 |
| cgccagtctt ttggaccagc tgatcgaaga ggtactggct gataatcttc cacctcctag | 120 |
| ccattttgaa ccacctaccc ttcacgaact gtatgattta dacgtgacgg ccccgaaga | 180 |
| tcccaacgag gaggcggttt cgcagatttt tcccgactct gtaatgttgg cggtgcagga | 240 |
| agggattgac ttactcactt ttccgccggc gcccggttct ccggagccgc ctcacctttc | 300 |
| ccggcagccc gagcagccgg agcagagagc cttgggtccg gtttctatgc caaaccttgt | 360 |
| accggaggtg atcgatctta cctgccacga ggctggcttt ccacccagtg acgacgagga | 420 |
| tgaagagggt cctgtgtctg aacctgagcc tgagcccgag ccagaaccgg agcctgcaag | 480 |
| acctacccgc cgtcctaaaa tggcgcctgc tatcctgaga cgcccgacat cacctgtgtc | 540 |
| tagagaatgc aatagtagta cggatagctg tgactccggt ccttctaaca cacctcctga | 600 |
| gatacacccg gtggtcccgc tgtgccccat taaaccagtt gccgtgagag ttggtgggcg | 660 |
| tcgccaggct gtggaatgta tcgaggactt gcttaacgag cctgggcaac ctttggactt | 720 |
| gagctgtaaa cgccccaggc cagcggccgc agaagtgcag ttagggctgg aagggtcta | 780 |
| ccctcggccg ccgtccaaga cctaccgagg agctttccag aatctgttcc agagcgtgcg | 840 |

```
cgaagtgatc cagaacccgg gccccaggca cccagaggcc gcgagcgcag caccctcccgg    900
cgccagtttg ctgctgctgc agcagcagca gcagcagcag cagcagcagc agcagcagca    960
gcagcagcag cagcagcagc aagagactag ccccaggcag cagcagcagc agcagggtga   1020
ggatggttct ccccaagccc atcgtagagg ccccacaggc tacctggtcc tggatgagga   1080
acagcaacct tcacagccgc agtcggccct ggagtgccac cccgagagag gttgcgtccc   1140
agagcctgga gccgccgtgg ccgccagcaa ggggctgccg cagcagctgc cagcacctcc   1200
ggacgaggat gactcagctg ccccatccac gttgtccctg ctgggcccca ctttccccgg   1260
cttaagcagc tgctccgctg accttaaaga catcctgagc gaggccagca ccatgcaact   1320
ccttcagcaa cagcagcagg aagcagtatc cgaaggcagc agcagcggga gagcgaggga   1380
ggcctcgggg gctcccactt cctccaagga caattactta gggggcactt cgaccatttc   1440
tgacaacgcc aaggagttgt gtaaggcagt gtcggtgtcc atgggcctgg gtgtggaggc   1500
gttggagcat ctgagtccag gggaacagct tcgggggggat tgcatgtacg ccccactttt   1560
gggagttcca cccgctgtgc gtcccactcc ttgtgcccca ttggccgaat gcaaaggttc   1620
tctgctagac gacagcgcag gcaagagcac tgaagatact gctgagtatt ccccttttcaa  1680
gggaggttac accaaagggc tagaaggcga gagcctaggc tgctctggca gcgctgcagc   1740
agggagctcc gggacacttg aactgccgtc taccctgtct ctctacaagt ccggagcact   1800
ggacgaggca gctgcgtacc agagtcgcga ctactacaac tttccactgg ctctggccgg   1860
accgccgccc cctccgccgc ctccccatcc ccacgctcgc atcaagctgg agaacccgct   1920
ggactacggc agcgcctggg cggctgcggc ggcgcagtgc cgctatgggg acctggcgag   1980
cctgcatggc gcgggtgcag cgggacccgg ttctgggtca ccctcagccg ccgcttcctc   2040
atcctggcac actctcttca cagccgaaga aggccagttg tatggaccgt gtggtggtgg   2100
tgggggtggt ggcggcggcg gcggcggcgg cggcggcggc ggcggcggcg gcggcggcgg   2160
cggcgaggcg ggagctgtag cccctacgg ctacactcgg ccccctcagg ggctggcggg   2220
ccaggaaagc gacttcaccg cacctgatgt gtggtaccct ggcggcatgg tgagcagagt   2280
gccctatccc agtcccactt gtgtcaaaag cgaaatgggc ccctggatgg atagctactc   2340
cggaccttac ggggacatgc gtttggagac tgccagggac catgttttgc ccattgacta   2400
ttacttccca ccccagaaga cctgcctgat ctgtggagat gaagcttctg ggtgtcacta   2460
tggagctctc acatgtggaa gctgcaaggt cttcttcaaa agagccgctg aagggaaaca   2520
gaagtacctg tgcgccagca gaaatgattg cactattgat aaattccgaa ggaaaaattg   2580
tccatcttgt cgtcttcgga atgttatga agcagggatg actctgggag cccggaagct   2640
gaagaaactt ggtaatctga aactacagga ggaaggagag gcttccagca ccaccagccc   2700
cactgagtga ctcgag                                                    2716
```

<210> SEQ ID NO 6
<211> LENGTH: 1051
<212> TYPE: DNA
<213> ORGANISM: Artificial Sequence
<220> FEATURE:
<223> OTHER INFORMATION: Description of Artificial Sequence: Synthetic
      nucleotide sequence construct 12S/DBD

<400> SEQUENCE: 6

```
accgggactg aaaatgagac atattatctg ccacggaggt gttattaccg aagaaatggc     60
cgccagtctt ttggaccagc tgatcgaaga ggtactggct gataatcttc cacctcctag    120
```

-continued

```
ccattttgaa ccacctaccc ttcacgaact gtatgattta gacgtgacgg ccccgaaga      180 tcccaacgag gaggcggttt cgcagatttt tcccgactct gtaatgttgg cggtgcagga      240
agggattgac ttactcactt ttccgccggc gcccggttct ccggagccgc ctcacctttc      300
ccggcagccc gagcagccgg agcagagagc cttgggtccg gtttctatgc caaaccttgt      360
accggaggtg atcgatctta cctgccacga ggctggcttt ccacccagtg acgacgagga      420
tgaagagggt cctgtgtctg aacctgagcc tgagcccgag ccagaaccgg agcctgcaag      480
acctacccgc cgtcctaaaa tggcgcctgc tatcctgaga cgcccgacat cacctgtgtc      540
tagagaatgc aatagtagta cggatagctg tgactccggt ccttctaaca cacctcctga      600
gatacacccg gtggtcccgc tgtgccccat taaaccagtt gccgtgagag ttggtgggcg      660
tcgccaggct gtggaatgta tcgaggactt gcttaacgag cctgggcaac ctttggactt      720
gagctgtaaa cgcccccaggc cagcggccga aaagacctgc ctgatctgtg agatgaagc      780 ttctgggtgt cactatggag ctctcacatg tggaagctgc aaggtcttct tcaaaagagc      840
cgctgaaggg aaacagaagt acctgtgcgc cagcagaaat gattgcacta ttgataaatt      900
ccgaaggaaa aattgtccat cttgtcgtct tcggaaatgt tatgaagcag ggatgactct      960
gggagcccgg aagctgaaga aacttggtaa tctgaaacta caggaggaag gagaggcttc     1020
cagcaccacc agccccactg agtgactcga g                                   1051
```

<210> SEQ ID NO 7
<211> LENGTH: 1164
<212> TYPE: PRT
<213> ORGANISM: Artificial Sequence
<220> FEATURE:
<223> OTHER INFORMATION: Description of Artificial Sequence: Synthetic amino acid sequence construct 12S/AR

<400> SEQUENCE: 7

```
Met Arg His Ile Ile Cys His Gly Gly Val Ile Thr Glu Glu Met Ala
  1               5                  10                  15

Ala Ser Leu Leu Asp Gln Leu Ile Glu Glu Val Leu Ala Asp Asn Leu
                 20                  25                  30

Pro Pro Pro Ser His Phe Glu Pro Thr Leu His Glu Leu Tyr Asp
             35                  40                  45

Leu Asp Val Thr Ala Pro Glu Asp Pro Asn Glu Glu Ala Val Ser Gln
         50                  55                  60

Ile Phe Pro Asp Ser Val Met Leu Ala Val Gln Glu Gly Ile Asp Leu
 65                  70                  75                  80

Leu Thr Phe Pro Pro Ala Pro Gly Ser Pro Glu Pro Pro His Leu Ser
                 85                  90                  95

Arg Gln Pro Glu Gln Pro Glu Gln Arg Ala Leu Gly Pro Val Ser Met
                100                 105                 110

Pro Asn Leu Val Pro Glu Val Ile Asp Leu Thr Cys His Glu Ala Gly
             115                 120                 125

Phe Pro Pro Ser Asp Asp Glu Asp Glu Glu Gly Pro Val Ser Glu Pro
         130                 135                 140

Glu Pro Glu Pro Glu Pro Glu Pro Glu Pro Ala Arg Pro Thr Arg Arg
145                 150                 155                 160

Pro Lys Met Ala Pro Ala Ile Leu Arg Arg Pro Thr Ser Pro Val Ser
                165                 170                 175

Arg Glu Cys Asn Ser Ser Thr Asp Ser Cys Asp Ser Gly Pro Ser Asn
             180                 185                 190
```

-continued

```
Thr Pro Pro Glu Ile His Pro Val Pro Leu Cys Pro Ile Lys Pro
        195                 200                 205

Val Ala Val Arg Val Gly Gly Arg Arg Gln Ala Val Glu Cys Ile Glu
210             215                 220

Asp Leu Leu Asn Glu Pro Gly Gln Pro Leu Asp Leu Ser Cys Lys Arg
225                 230                 235                 240

Pro Arg Pro Ala Ala Glu Val Gln Leu Gly Leu Gly Arg Val Tyr
                245                 250                 255

Pro Arg Pro Pro Ser Lys Thr Tyr Arg Gly Ala Phe Gln Asn Leu Phe
            260                 265                 270

Gln Ser Val Arg Glu Val Ile Gln Asn Pro Gly Pro Arg His Pro Glu
        275                 280                 285

Ala Ala Ser Ala Ala Pro Pro Gly Ala Ser Leu Leu Leu Leu Gln Gln
290                 295                 300

Gln Gln Gln Gln Gln Gln Gln Gln Gln Gln Gln Gln Gln Gln Gln
305                 310                 315                 320

Gln Gln Gln Glu Thr Ser Pro Arg Gln Gln Gln Gln Gln Gly Glu
                325                 330                 335

Asp Gly Ser Pro Gln Ala His Arg Arg Gly Pro Thr Gly Tyr Leu Val
            340                 345                 350

Leu Asp Glu Glu Gln Pro Ser Gln Pro Gln Ser Ala Leu Glu Cys
        355                 360                 365

His Pro Glu Arg Gly Cys Val Pro Glu Pro Gly Ala Ala Val Ala Ala
    370                 375                 380

Ser Lys Gly Leu Pro Gln Gln Leu Pro Ala Pro Pro Asp Glu Asp Asp
385                 390                 395                 400

Ser Ala Ala Pro Ser Thr Leu Ser Leu Leu Gly Pro Thr Phe Pro Gly
                405                 410                 415

Leu Ser Ser Cys Ser Ala Asp Leu Lys Asp Ile Leu Ser Glu Ala Ser
            420                 425                 430

Thr Met Gln Leu Leu Gln Gln Gln Gln Glu Ala Val Ser Glu Gly
        435                 440                 445

Ser Ser Ser Gly Arg Ala Arg Glu Ala Ser Gly Ala Pro Thr Ser Ser
450                 455                 460

Lys Asp Asn Tyr Leu Gly Gly Thr Ser Thr Ile Ser Asp Asn Ala Lys
465                 470                 475                 480

Glu Leu Cys Lys Ala Val Ser Val Ser Met Gly Leu Gly Val Glu Ala
                485                 490                 495

Leu Glu His Leu Ser Pro Gly Glu Gln Leu Arg Gly Asp Cys Met Tyr
            500                 505                 510

Ala Pro Leu Leu Gly Val Pro Ala Val Arg Pro Thr Pro Cys Ala
        515                 520                 525

Pro Leu Ala Glu Cys Lys Gly Ser Leu Leu Asp Asp Ser Ala Gly Lys
    530                 535                 540

Ser Thr Glu Asp Thr Ala Glu Tyr Ser Pro Phe Lys Gly Gly Tyr Thr
545                 550                 555                 560

Lys Gly Leu Glu Gly Glu Ser Leu Gly Cys Ser Gly Ser Ala Ala
                565                 570                 575

Gly Ser Ser Gly Thr Leu Glu Leu Pro Ser Thr Leu Ser Leu Tyr Lys
            580                 585                 590

Ser Gly Ala Leu Asp Glu Ala Ala Ala Tyr Gln Ser Arg Asp Tyr Tyr
        595                 600                 605
```

```
Asn Phe Pro Leu Ala Leu Ala Gly Pro Pro Pro Pro Pro Pro
    610                 615                 620

His Pro His Ala Arg Ile Lys Leu Glu Asn Pro Leu Asp Tyr Gly Ser
625                 630                 635                 640

Ala Trp Ala Ala Ala Ala Gln Cys Arg Tyr Gly Asp Leu Ala Ser
                    645                 650                 655

Leu His Gly Ala Gly Ala Ala Gly Pro Gly Ser Gly Ser Pro Ser Ala
                660                 665                 670

Ala Ala Ser Ser Ser Trp His Thr Leu Phe Thr Ala Glu Glu Gly Gln
            675                 680                 685

Leu Tyr Gly Pro Cys Gly Gly Gly Gly Gly Gly Gly Gly Gly
    690                 695                 700

Gly Gly Gly Gly Gly Gly Gly Gly Gly Gly Gly Gly Glu Ala Gly
705                 710                 715                 720

Ala Val Ala Pro Tyr Gly Tyr Thr Arg Pro Pro Gln Gly Leu Ala Gly
                725                 730                 735

Gln Glu Ser Asp Phe Thr Ala Pro Asp Val Trp Tyr Pro Gly Gly Met
                740                 745                 750

Val Ser Arg Val Pro Tyr Pro Ser Pro Thr Cys Val Lys Ser Glu Met
    755                 760                 765

Gly Pro Trp Met Asp Ser Tyr Ser Gly Pro Tyr Gly Asp Met Arg Leu
770                 775                 780

Glu Thr Ala Arg Asp His Val Leu Pro Ile Asp Tyr Tyr Phe Pro Pro
785                 790                 795                 800

Gln Lys Thr Cys Leu Ile Cys Gly Asp Glu Ala Ser Gly Cys His Tyr
                805                 810                 815

Gly Ala Leu Thr Cys Gly Ser Cys Lys Val Phe Phe Lys Arg Ala Ala
                820                 825                 830

Glu Gly Lys Gln Lys Tyr Leu Cys Ala Ser Arg Asn Asp Cys Thr Ile
            835                 840                 845

Asp Lys Phe Arg Arg Lys Asn Cys Pro Ser Cys Arg Leu Arg Lys Cys
    850                 855                 860

Tyr Glu Ala Gly Met Thr Leu Gly Ala Arg Lys Leu Lys Lys Leu Gly
865                 870                 875                 880

Asn Leu Lys Leu Gln Glu Gly Glu Ala Ser Ser Thr Thr Ser Pro
                885                 890                 895

Thr Glu Glu Thr Thr Gln Lys Leu Thr Val Ser His Ile Glu Gly Tyr
            900                 905                 910

Glu Cys Gln Pro Ile Phe Leu Asn Val Leu Glu Ala Ile Glu Pro Gly
            915                 920                 925

Val Val Cys Ala Gly His Asp Asn Asn Gln Pro Asp Ser Phe Ala Ala
    930                 935                 940

Leu Leu Ser Ser Leu Asn Glu Leu Gly Glu Arg Gln Leu Val His Val
945                 950                 955                 960

Val Lys Trp Ala Lys Ala Leu Pro Gly Phe Arg Asn Leu His Val Asp
                965                 970                 975

Asp Gln Met Ala Val Ile Gln Tyr Ser Trp Met Gly Leu Met Val Phe
                980                 985                 990

Ala Met Gly Trp Arg Ser Phe Thr Asn Val Asn Ser Arg Met Leu Tyr
            995                 1000                1005

Phe Ala Pro Asp Leu Val Phe Asn Glu Tyr Arg Met His Lys Ser Arg
    1010                1015                1020
```

-continued

```
Met Tyr Ser Gln Cys Val Arg Met Arg His Leu Ser Gln Glu Phe Gly
1025                1030                1035                1040

Trp Leu Gln Ile Thr Pro Gln Glu Phe Leu Cys Met Lys Ala Leu Leu
            1045                1050                1055

Leu Phe Ser Ile Ile Pro Val Asp Gly Leu Lys Asn Gln Lys Phe Phe
        1060                1065                1070

Asp Glu Leu Arg Met Asn Tyr Ile Lys Glu Leu Asp Arg Ile Ile Ala
    1075                1080                1085

Cys Lys Arg Lys Asn Pro Thr Ser Cys Ser Arg Arg Phe Tyr Gln Leu
   1090                1095                1100

Thr Lys Leu Leu Asp Ser Val Gln Pro Ile Ala Arg Glu Leu His Gln
1105                1110                1115                1120

Phe Thr Phe Asp Leu Leu Ile Lys Ser His Met Val Ser Val Asp Phe
            1125                1130                1135

Pro Glu Met Met Ala Glu Ile Ile Ser Val Gln Val Pro Lys Ile Leu
        1140                1145                1150

Ser Gly Lys Val Lys Pro Ile Tyr Phe His Thr Gln
    1155                1160

<210> SEQ ID NO 8
<211> LENGTH: 898
<212> TYPE: PRT
<213> ORGANISM: Artificial Sequence
<220> FEATURE:
<223> OTHER INFORMATION: Description of Artificial Sequence: Synthetic
      amino acid sequence construct 12S/TAD

<400> SEQUENCE: 8

Met Arg His Ile Ile Cys His Gly Gly Val Ile Thr Glu Glu Met Ala
 1               5                  10                  15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gln Ile Asp Leu
 65                  70                  75                  80

Leu Thr Phe Pro Pro Ala Pro Gly Ser Pro Glu Pro His Leu Ser
                85                  90                  95

Arg Gln Pro Glu Gln Pro Glu Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser Asp Asp Glu Asp Glu Glu Gly Pro Val Ser Glu Pro
    130                 135                 140

Glu Pro Glu Pro Glu Pro Glu Pro Ala Arg Pro Thr Arg Arg
145                 150                 155                 160

Pro Lys Met Ala Pro Ala Ile Leu Arg Arg Pro Thr Ser Pro Val Ser
                165                 170                 175

Arg Glu Cys Asn Ser Ser Thr Asp Ser Cys Asp Ser Gly Pro Ser Asn
            180                 185                 190

Thr Pro Pro Glu Ile His Pro Val Val Pro Leu Cys Pro Ile Lys Pro
        195                 200                 205

Val Ala Val Arg Val Gly Gly Arg Arg Gln Ala Val Glu Cys Ile Glu
    210                 215                 220
```

```
Asp Leu Leu Asn Glu Pro Gly Gln Pro Leu Asp Leu Ser Cys Lys Arg
225                 230                 235                 240

Pro Arg Pro Ala Ala Ala Glu Val Gln Leu Gly Leu Gly Arg Val Tyr
            245                 250                 255

Pro Arg Pro Pro Ser Lys Thr Tyr Arg Gly Ala Phe Gln Asn Leu Phe
        260                 265                 270

Gln Ser Val Arg Glu Val Ile Gln Asn Pro Gly Pro Arg His Pro Glu
    275                 280                 285

Ala Ala Ser Ala Ala Pro Pro Gly Ala Ser Leu Leu Leu Leu Gln Gln
290                 295                 300

Gln Gln Gln Gln Gln Gln Gln Gln Gln Gln Gln Gln Gln Gln Gln Gln
305                 310                 315                 320

Gln Gln Gln Glu Thr Ser Pro Arg Gln Gln Gln Gln Gln Gly Glu
                325                 330                 335

Asp Gly Ser Pro Gln Ala His Arg Arg Gly Pro Thr Gly Tyr Leu Val
                340                 345                 350

Leu Asp Glu Glu Gln Gln Pro Ser Gln Pro Gln Ser Ala Leu Glu Cys
        355                 360                 365

His Pro Glu Arg Gly Cys Val Pro Glu Pro Gly Ala Ala Val Ala Ala
        370                 375                 380

Ser Lys Gly Leu Pro Gln Gln Leu Pro Ala Pro Pro Asp Glu Asp Asp
385                 390                 395                 400

Ser Ala Ala Pro Ser Thr Leu Ser Leu Leu Gly Pro Thr Phe Pro Gly
                405                 410                 415

Leu Ser Ser Cys Ser Ala Asp Leu Lys Asp Ile Leu Ser Glu Ala Ser
                420                 425                 430

Thr Met Gln Leu Leu Gln Gln Gln Gln Glu Ala Val Ser Glu Gly
                435                 440                 445

Ser Ser Ser Gly Arg Ala Arg Glu Ala Ser Gly Ala Pro Thr Ser Ser
    450                 455                 460

Lys Asp Asn Tyr Leu Gly Gly Thr Ser Thr Ile Ser Asp Asn Ala Lys
465                 470                 475                 480

Glu Leu Cys Lys Ala Val Ser Val Ser Met Gly Leu Gly Val Glu Ala
                485                 490                 495

Leu Glu His Leu Ser Pro Gly Glu Gln Leu Arg Gly Asp Cys Met Tyr
            500                 505                 510

Ala Pro Leu Leu Gly Val Pro Ala Val Arg Pro Thr Pro Cys Ala
            515                 520                 525

Pro Leu Ala Glu Cys Lys Gly Ser Leu Leu Asp Asp Ser Ala Gly Lys
    530                 535                 540

Ser Thr Glu Asp Thr Ala Glu Tyr Ser Pro Phe Lys Gly Gly Tyr Thr
545                 550                 555                 560

Lys Gly Leu Glu Gly Glu Ser Leu Gly Cys Ser Gly Ser Ala Ala
                565                 570                 575

Gly Ser Ser Gly Thr Leu Glu Leu Pro Ser Thr Leu Ser Leu Tyr Lys
            580                 585                 590

Ser Gly Ala Leu Asp Glu Ala Ala Ala Tyr Gln Ser Arg Asp Tyr Tyr
            595                 600                 605

Asn Phe Pro Leu Ala Leu Ala Gly Pro Pro Pro Pro Pro Pro Pro
        610                 615                 620

His Pro His Ala Arg Ile Lys Leu Glu Asn Pro Leu Asp Tyr Gly Ser
625                 630                 635                 640
```

```
Ala Trp Ala Ala Ala Ala Gln Cys Arg Tyr Gly Asp Leu Ala Ser
            645                 650                 655

Leu His Gly Ala Gly Ala Ala Gly Pro Gly Ser Gly Ser Pro Ser Ala
            660                 665                 670

Ala Ala Ser Ser Ser Trp His Thr Leu Phe Thr Ala Glu Glu Gly Gln
            675                 680                 685

Leu Tyr Gly Pro Cys Gly Gly Gly Gly Gly Gly Gly Gly Gly
        690                 695                 700

Gly Gly Gly Gly Gly Gly Gly Gly Gly Gly Gly Glu Ala Gly
705                 710                 715                 720

Ala Val Ala Pro Tyr Gly Tyr Thr Arg Pro Pro Gln Gly Leu Ala Gly
            725                 730                 735

Gln Glu Ser Asp Phe Thr Ala Pro Asp Val Trp Tyr Pro Gly Gly Met
            740                 745                 750

Val Ser Arg Val Pro Tyr Pro Ser Pro Thr Cys Val Lys Ser Glu Met
            755                 760                 765

Gly Pro Trp Met Asp Ser Tyr Ser Gly Pro Tyr Gly Asp Met Arg Leu
            770                 775                 780

Glu Thr Ala Arg Asp His Val Leu Pro Ile Asp Tyr Tyr Phe Pro Pro
785                 790                 795                 800

Gln Lys Thr Cys Leu Ile Cys Gly Asp Glu Ala Ser Gly Cys His Tyr
            805                 810                 815

Gly Ala Leu Thr Cys Gly Ser Cys Lys Val Phe Phe Lys Arg Ala Ala
            820                 825                 830

Glu Gly Lys Gln Lys Tyr Leu Cys Ala Ser Arg Asn Asp Cys Thr Ile
            835                 840                 845

Asp Lys Phe Arg Arg Lys Asn Cys Pro Ser Cys Arg Leu Arg Lys Cys
            850                 855                 860

Tyr Glu Ala Gly Met Thr Leu Gly Ala Arg Lys Leu Lys Lys Leu Gly
865                 870                 875                 880

Asn Leu Lys Leu Gln Glu Gly Glu Ala Ser Ser Thr Thr Ser Pro
            885                 890                 895

Thr Glu

<210> SEQ ID NO 9
<211> LENGTH: 343
<212> TYPE: PRT
<213> ORGANISM: Artificial Sequence
<220> FEATURE:
<223> OTHER INFORMATION: Description of Artificial Sequence: Synthetic
      amino acid sequence construct 12S/DBD

<400> SEQUENCE: 9

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
        50                  55                  60

Ile Phe Pro Asp Ser Val Met Leu Ala Val Gln Glu Gly Ile Asp Leu
65              70                  75                  80

Leu Thr Phe Pro Pro Ala Pro Gly Ser Pro Glu Pro Pro His Leu Ser
            85                  90                  95
```

```
Arg Gln Pro Glu Gln Pro Glu Gln Arg Ala Leu Gly Pro Val Ser Met
                100                 105                 110
Pro Asn Leu Val Pro Glu Val Ile Asp Leu Thr Cys His Glu Ala Gly
            115                 120                 125
Phe Pro Pro Ser Asp Asp Glu Asp Glu Glu Gly Pro Val Ser Glu Pro
        130                 135                 140
Glu Pro Glu Pro Glu Pro Glu Pro Ala Arg Pro Thr Arg Arg
145                 150                 155                 160
Pro Lys Met Ala Pro Ala Ile Leu Arg Arg Pro Thr Ser Pro Val Ser
                165                 170                 175
Arg Glu Cys Asn Ser Ser Thr Asp Ser Cys Asp Ser Gly Pro Ser Asn
            180                 185                 190
Thr Pro Pro Glu Ile His Pro Val Val Pro Leu Cys Pro Ile Lys Pro
        195                 200                 205
Val Ala Val Arg Val Gly Gly Arg Arg Gln Ala Val Glu Cys Ile Glu
    210                 215                 220
Asp Leu Leu Asn Glu Pro Gly Gln Pro Leu Asp Leu Ser Cys Lys Arg
225                 230                 235                 240
Pro Arg Pro Ala Ala Ala Lys Thr Cys Leu Ile Cys Gly Asp Glu Ala
                245                 250                 255
Ser Gly Cys His Tyr Gly Ala Leu Thr Cys Gly Ser Cys Lys Val Phe
            260                 265                 270
Phe Lys Arg Ala Ala Glu Gly Lys Gln Lys Tyr Leu Cys Ala Ser Arg
        275                 280                 285
Asn Asp Cys Thr Ile Asp Lys Phe Arg Arg Lys Asn Cys Pro Ser Cys
    290                 295                 300
Arg Leu Arg Lys Cys Tyr Glu Ala Gly Met Thr Leu Gly Ala Arg Lys
305                 310                 315                 320
Leu Lys Lys Leu Gly Asn Leu Lys Leu Gln Glu Glu Gly Glu Ala Ser
                325                 330                 335
Ser Thr Thr Ser Pro Thr Glu
            340

<210> SEQ ID NO 10
<211> LENGTH: 986
<212> TYPE: DNA
<213> ORGANISM: Artificial Sequence
<220> FEATURE:
<223> OTHER INFORMATION: Description of Artificial Sequence: Synthetic
      nucleotide sequence construct EA1

<400> SEQUENCE: 10
atgagacata ttatctgcca cggaggtgtt attaccgaag aaatggccgc cagtcttttg      60
gaccagctga tcgaagaggt actggctgat aatcttccac ctcctagcca ttttgaacca     120
cctacccttc acgaactgta tgatttagac gtgacggccc ccgaagatcc caacgaggag     180
gcggtttcgc agattttcc cgactctgta atgttggcgg tgcaggaagg gattgactta      240
ctcacttttc cgccggcgcc cggttctccg gagccgcctc acctttcccg gcagcccgag     300
cagccggagc agagagcctt gggtccggtt tctatgccaa accttgtacc ggaggtgatc     360
gatcttacct gccacgaggc tggctttcca cccagtgacg acgaggatga gagggtgag      420 gagtttgtgt tagattatgt ggagcacccc gggcacggtt gcaggtcttg tcattatcac     480
cggaggaata cgggggaccc agatattatg tgttcgcttt gctatatgag gacctgtggc     540
atgtttgtct acagtaagtg aaaattatgg gcagtgggtg atagagtggt gggtttggtg     600
```

-continued

```
tggtaatttt tttttaatt tttacagttt tgtggtttaa agaattttgt attgtgattt      660
ttttaaaagg tcctgtgtct gaacctgagc ctgagcccga gccagaaccg gagcctgcaa     720
gacctacccg ccgtcctaaa atggcgcctg ctatcctgag acgcccgaca tcacctgtgt     780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataa                                         986
```

```
<210> SEQ ID NO 11
<211> LENGTH: 986
<212> TYPE: DNA
<213> ORGANISM: Artificial Sequence
<220> FEATURE:
<223> OTHER INFORMATION: Description of Artificial Sequence: Synthetic
      nucleotide sequence construct EA1/TAD

<400> SEQUENCE: 11
atgagacata ttatctgcca cggaggtgtt attaccgaag aaatggccgc cagtctttg      60 gaccagctga tcgaagaggt actggctgat aatcttccac ctcctagcca ttttgaacca    120
cctaccctct cgaactgta tgatttagac gtgacggccc ccgaagatcc caacgaggag     180
gcggtttcgc agatttttcc cgactctgta atgttggcgg tgcaggaagg gattgactta    240 ctcactttc cgccggcgcc cggttctccg gagccgcctc acctttcccg gcagcccgag     300
cagccggagc agagagcctt gggtccggtt tctatgccaa accttgtacc ggaggtgatc    360
gatcttacct gccacgaggc tggctttcca cccagtgacg acgaggatga agagggtgag    420
gagtttgtgt tagattatgt ggagcacccc gggcacggtt gcaggtcttg tcattatcac    480
cggaggaata cggggggaccc agatattatg tgttcgcttt gctatatgag gacctgtggc    540
atgtttgtct acagtaagtg aaaattatgg gcagtgggtg atagagtggt gggtttggtg    600
tggtaatttt tttttaatt tttacagttt tgtggtttaa agaattttgt attgtgattt      660
ttttaaaagg tcctgtgtct gaacctgagc ctgagcccga gccagaaccg gagcctgcaa     720
gacctacccg ccgtcctaaa atggcgcctg ctatcctgag acgcccgaca tcacctgtgt     780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataa                                         986
```

```
<210> SEQ ID NO 12
<211> LENGTH: 1022
<212> TYPE: DNA
<213> ORGANISM: Artificial Sequence
<220> FEATURE:
<223> OTHER INFORMATION: Description of Artificial Sequence: Synthetic
      nucleotide sequence construct EA1/AR

<400> SEQUENCE: 12
atgagacata ttatctgcca cggaggtgtt attaccgaag aaatggccgc cagtctttg      60 gaccagctga tcgaagaggt actggctgat aatcttccac ctcctagcca ttttgaacca    120
cctaccctct cgaactgta tgatttagac gtgacggccc ccgaagatcc caacgaggag     180
gcggtttcgc agatttttcc cgactctgta atgttggcgg tgcaggaagg gattgactta    240 ctcactttc cgccggcgcc cggttctccg gagccgcctc acctttcccg gcagcccgag     300
```

```
cagccggagc agagagcctt gggtccggtt tctatgccaa accttgtacc ggaggtgatc    360
gatcttacct gccacgaggc tggctttcca cccagtgacg acgaggatga agagggtgag    420
gagtttgtgt tagattatgt ggagcacccc gggcacggtt gcaggtcttg tcattatcac    480
cggaggaata cgggggaccc agatattatg tgttcgcttt gctatatgag gacctgtggc    540
atgtttgtct acagtaagtg aaaattatgg gcagtgggtg atagagtggt gggtttggtg    600
tggtaatttt tttttttaatt tttacagttt tgtggtttaa agaattttgt attgtgattt    660
ttttaaaagg tcctgtgtct gaacctgagc ctgagcccga gccagaaccg agcctgcaa    720 gacctacccg ccgtcctaaa atggcgcctg ctatcctgag acgcccgaca tcacctgtgt    780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataagcgg ccgcagaagt gcagttaggg ctgggaaggg    1020
tc                                                                  1022
```

```
<210> SEQ ID NO 13
<211> LENGTH: 1022
<212> TYPE: DNA
<213> ORGANISM: Artificial Sequence
<220> FEATURE:
<223> OTHER INFORMATION: Description of Artificial Sequence: Synthetic
      nucleotide sequence construct EA1/AR(C685Y)

<400> SEQUENCE: 13
```

```
atgagacata ttatctgcca cggaggtgtt attaccgaag aaatggccgc cagtcttttg     60
gaccagctga tcgaagaggt actggctgat aatcttccac ctcctagcca ttttgaacca    120
cctacccttc acgaactgta tgatttagac gtgacggccc ccgaagatcc caacgaggag    180
gcggtttcgc agattttttcc cgactctgta atgttggcgg tgcaggaagg gattgactta    240
ctcacttttc cgccggcgcc cggttctccg gagccgcctc accttttccg gcagcccgag    300
cagccggagc agagagcctt gggtccggtt tctatgccaa accttgtacc ggaggtgatc    360
gatcttacct gccacgaggc tggctttcca cccagtgacg acgaggatga agagggtgag    420
gagtttgtgt tagattatgt ggagcacccc gggcacggtt gcaggtcttg tcattatcac    480
cggaggaata cgggggaccc agatattatg tgttcgcttt gctatatgag gacctgtggc    540
atgtttgtct acagtaagtg aaaattatgg gcagtgggtg atagagtggt gggtttggtg    600
tggtaatttt tttttttaatt tttacagttt tgtggtttaa agaattttgt attgtgattt    660
ttttaaaagg tcctgtgtct gaacctgagc ctgagcccga gccagaaccg agcctgcaa    720 gacctacccg ccgtcctaaa atggcgcctg ctatcctgag acgcccgaca tcacctgtgt    780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataagcgg ccgcagaagt gcagttaggg ctgggaaggg    1020
tc                                                                  1022
```

```
<210> SEQ ID NO 14
<211> LENGTH: 36
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
tcactcggat ccaccgggac tgaaaatgag acatat                               36

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tacatcactc gcggccgctg gcctggggcg tttacagctc a                         41

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tacatcactc gcggccgcag aagtgcagtt agggctggga a                         41

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcactcctcg agtcactggg tgtggaaata gatgggctt                            39

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tacatcactc gcggccgcag aagtgcagtt agggctggga a                         41

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcactcctcg agtcactcag tggggctggt ggtgctgga                            39

<210> SEQ ID NO 20
<211> LENGTH: 43
<212> TYPE: DNA
<213> ORGANISM: Artificial Sequence
```

```
-continued

<220> FEATURE:
<223> OTHER INFORMATION: Description of Artificial Sequence: Synthetic
      primer

<400> SEQUENCE: 20
tacatcactc gcggccgcaa agacctgcct gatctgtgga gat            43

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cccaagcttt ccttctaaca cacctcctg                            29

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgggatccga ggtcagatgt aaccaaga                             28
```

ENHANCEMENT OF ADENOVIRAL ONCOLYTIC ACTIVITY BY MODIFICATION OF THE E1A GENE PRODUCT

RELATED APPLICATIONS

This application claims the benefit of U.S. Provisional Application Ser. No. 60/401,919, filed Aug. 8, 2002. The entire contents of this application is incorporated herein by this reference.

GOVERNMENT SUPPORT

This work described herein was supported by a grant from the National Institutes of Health (Grant No. CA58236). Therefore, the U.S. Government may have certain rights in the invention.

BACKGROUND OF THE INVENTION

Prostate cancer is the most common cancer, excluding non-melanoma skin cancers, in American men. The American Cancer Society estimates that in the year 2000 approximately 180,400 new cases of prostate cancer were diagnosed in the United States. Prostate cancer is the second leading cause of cancer death in men, exceeded only by lung cancer. Prostate cancer causes about 11 percent of all cancer deaths in men. Furthermore, it is estimated that approximately 5 million men have at this very moment a histological cancer of the prostate, which may or may not ever become clinically evident. The prostate gland is about the size of a walnut and is located anterior to the rectum, adjacent to the bladder and surrounds the proximal part of the urethra. It contains glandular epithelium that produces a portion of the seminal fluid which protects and nourishes sperm cells. Although other cells exist in the prostate, over 99% of prostate cancers develop are adenocarcinomas.

Prostate cancer is a multi-focal disease with clones of androgen-sensitive and androgen-refractory cells (N. Kyprianou and J. Isaacs, Biochem. Biophys. Res. Comm., 165, 73-81, 1989; Kyprianou, N., et al., World J. Urol., 12, 299-303, 1994; M. Tenniswood and H. Michna, Ernst Schering Research Foundation Workshop, 14, Springer-Verlag, Berlin Heidelberg, 1995). The role androgen receptors (AR) may play in prostate cancer is not clear. Although androgen depletion therapy results in regression of the tumor, it returns as an androgen-refractory cancer. Some androgen-refractory tumors express increased levels of androgen receptors, suggesting that continued proliferation of androgen-refractory prostate cells may be influenced by androgens (Linja, M. J., et al., Cancer Res., 61, 3350-3555, 2001). Paradoxically, increased expression of AR may also be responsible for inhibition of growth and may induce apoptosis (Joly-Pharaboz, M. O., et al., J. Steroid Biochem. Mol. Biol., 55, 67-76, 1995; Joly-Pharaboz, M. O., et al., J. Steroid Biochem. Mol. Biol., 73, 237-249, 2000; Dai, J. L., et al., Steroids, 61, 531-539, 1996; Umekita, Y., et al., Proc. Natl. Acad. Sci., USA, 93, 11802-11807, 1996; Zhau, H. Y. E., et al., Proc. Natl., Acad. Sci., USA, 93, 15152-15157, 1996; Heisler L. E., et al., Mol. Cell. Endocr., 126, 59-73, 1997; Shen, R., et al., Endocrinology, 141, 1699-1704, 2000).

Patients diagnosed with a clinically localized or "early-stage" prostate cancer may be treated with surgery, radiation, local ablation, or by non-treatment or "watchful waiting." The conventional surgery is a radical prostatectomy, which can be performed through a retropubic approach, a perineal approach, or in the case of laparoscopy through a transperitoneal approach. Surgery is usually reserved for locally confined disease and is usually curative. (Catalona W J et al., "Contemporary results of anatomic radical prostatectomy," CA Cancer J Clin 40: 282, 1999). These procedures are invasive, possess significant side effects (urinary incontinence and impotence), and require hospital stays and time out of work. Definitive surgical treatment to extirpate the early stage cancer often involves some type of radical prostatectomy. Modifications of surgical techniques have been developed to preserve potency in patients undergoing radical prostatectomy. (Walsh, P. C. "Anatomic radical prostatectomy: evolution of the surgical technique". J Urol, 160:2418-2424, 1998.). Meticulous surgical technique is vital, however, to minimize the incidence of positive surgical margins and consequent recurrent disease. (Rosen M A et al., "Frequency and location of extracapsular extension and positive surgical margins in radical prostatectomy specimens," J. Urol. 148:331, 1992).

Considerable interest has evolved in developing gene therapy vectors as therapeutic agents. Many proposed cancer therapeutic vectors are based on adenovirus. U.S. Pat. Nos. 5,631,236 and 6,096,718 (Baylor College of Medicine) cover a method of causing regression in a solid tumor, using a vector containing an HSV thymidine kinase (tk) gene, followed by administration of a prodrug such as ganciclovir. U.S. Pat. No. 6,096,718 (Baylor College of Medicine) relates to the use of a replication incompetent adenoviral vector, comprising an HSV tk gene under control of the alpha-lactalbumin promoter. U.S. Pat. Nos. 5,801,029 and 5,846,945 (Onyx Pharmaceuticals) relate to adenovirus in which the E1b gene has been altered so as not to bind and inactivate tumor suppressor p53 or RB proteins expressed by the host. This prevents the virus from inactivating tumor suppression in normal cells, which means the virus cannot replicate. However, the virus will replicate and lyse cells that have shut off p53 or RB expression through oncogenic transformation.

Adenoviruses are non-enveloped, regular icosohedral, double-stranded DNA viruses. The protein coat (capsid) is composed of 252 capsomeres of which 240 are hexons and 12 are pentons. Most of the detailed structural studies of the adenovirus polypeptides have been done for adenovirus types 2 and 5. The viral DNA is $23.85 \times 10^6$ daltons for adenovirus 2 and varies slightly in size depending on serotype. The DNA has inverted terminal repeats and the length of these varies with the serotype.

The replicative cycle is divided into early (E) and late (L) phases. The late phase defines the onset of viral DNA replication. Adenovirus structural proteins are generally synthesized during the late phase. Following adenovirus infection, host DNA and protein synthesis is inhibited in cells infected with most serotypes. The adenovirus lytic cycle with adenovirus 2 and adenovirus 5 is very efficient and results in approximately 10,000 virions per infected cell along with the synthesis of excess viral protein and DNA that is not incorporated into the virion. Early adenovirus transcription is a complicated sequence of interrelated biochemical events, but it entails essentially the synthesis of viral RNAs prior to the onset of viral DNA replication.

The organization of the adenovirus genome is similar in all of the adenovirus groups and specific functions are generally positioned at identical locations for each serotype studied. Early cytoplasmic messenger RNAs are complementary to four defined, noncontiguous regions on the viral DNA. These regions are designated (E1-E4). The early transcripts have been classified into an array of immediate early (E1a), delayed early (E1b, E2a, E2b, E3 and E4), and intermediate (IVa2.1X) regions.

The E1a region is involved in transcriptional transactivation of viral and cellular genes as well as transcriptional repression of other sequences. The E1a gene exerts an important control function on all of the other early adenovirus messenger RNAs. In normal tissues, in order to transcribe regions E1b, E2a, E2b, E3, or E4 efficiently, active E1a product is required. However, the E1a function may be bypassed. Cells may be manipulated to provide E1a-like functions or may naturally contain such functions. The virus may also be manipulated to bypass the functions.

The E1b region is required for the normal progression of viral events late in infection. The E1b product acts in the host nucleus. Mutants generated within the E1b sequences exhibit diminished late viral mRNA accumulation as well as impairment in the inhibition of host cellular transport normally observed late in adenovirus infection (Berkner, K. L., Biotechniques 6:616-629 (1988)). E1b is required for altering functions of the host cell such that processing and transport are shifted in favor of viral late gene products. These products then result in viral packaging and release of virions. E1b produces a 19 kD protein that prevents apoptosis. E1b also produces a 55 kD protein that binds to p53.

For a complete review on adenoviruses and their replication, see Horwitz, M. S., Virology 2d ed, Fields, B. N., eds., Raven Press Limited, New York (1990), Chapter 60, pp. 1679-1721.

Until relatively recently, the virtually exclusive focus in development of adenoviral vectors for gene therapy has been use of adenovirus merely as a vehicle for introducing the gene of interest, not as an effector in itself. Replication of adenovirus had previously been viewed as an undesirable result, largely due to the host immune response. More recently, however, the use of adenovirus vectors as effectors has been described (see e.g., International Patent Application Nos. PCT/US98/04084, PCT/US98/04080; PCT/US98/04133, PCT/US98/04132, PCT/US98/16312, PCT/US95/00845, PCT/US96/10838, PCT/EP98/07380, U.S. Pat. No. 5,998, 205 and U.S. Pat. No. 5,698,443). The use of IRES in vectors have been described. See, for example, International Patent Application No. PCT/US98/03699 and International Patent Application No. PCT/EP98/07380. Adenovirus E1A and E1B genes are disclosed in Rao et al. (1992, Proc. Natl. Acad. Sci. USA vol. 89:7742-7746).

Publications describing various aspects of adenovirus biology and/or techniques relating to adenovirus include the following: PCT/US95/14461; Graham and Van de Eb (1973) Virology 52:456-467; Takiff et al. (1981) Lancet 2(8251): 832-834; Berkner and Sharp (1983) Nucleic Acid Research 11 (17);6003-6020; Graham (1984) EMBO J 3:2917-2922; Bett et al. (1993) J. Virology 67:5911-5921; and Bett et al. (1994) Proc. Natl. Acad. Sci. USA 91:8802-8806. These references describe adenoviruses that have been genetically modified to produce replication-defective gene transfer vehicles. In such vehicles, the early adenovirus gene products E1A and E1B are deleted and provided in trans by the packaging cell line 293 developed by Frank Graham (Graham et al. (1987) J. Gen. Birol. 36:59-72 and Graham (1977) J. Genetic Virology 68:937-940). The gene to be transduced is commonly inserted into adenovirus in the deleted E1A and E1B region of the virus genome Bett et al. (1994), supra. Adenovirus vectors as vehicles for efficient transduction of genes have been described by Stratford-Perricaudet (1990) Human Gene Therapy 1:2-256; Rosenfeld (1991) Science 252:431-434; Wang et al. (1991) Adv. Exp. Med. Biol. 309: 61-66; Jaffe et al. (1992) Nat Gen. 1:372-378; Quantin et al. (1992) Proc Natl. Acad. Sci. USA 89:2581-2584; Rosenfeld et al. (1992) Cell 68:143-155; Stratford-Perricaudet et al. (1992) J. Clin. Invest. 90:626-630; Le Gal La Salle et al. (1993) Science 259:988-990; Mastrangeli et al. (1993) J. Clin. Invest. 91:225-234; Ragot et al. (1993) Nature 361:647-650; Hayaski et al. (1994) J. Biol. Chem. 269:23872-23875.

There are several other experimental cancer therapies which utilize various aspects of adenovirus or adenovirus vectors. See, U.S. Pat. No. 5,776,743; U.S. Pat. No. 5,846, 945; U.S. Pat. No. 5,801,029; PCT/US99/08592; U.S. Pat. No. 5,747,469; PCT/US98/03514; and PCT/US97/22036.

Of particular interest is the development of more specific, targeted forms of prostate cancer therapy. In contrast to conventional cancer therapies, which result in relatively nonspecific and often serious toxicity, more specific treatment modalities attempt to inhibit or kill malignant cells selectively while leaving healthy cells intact. There is, therefore a serious need for developing specific, less toxic prostate cancer therapies.

Furthermore, an effective treatment for prostate cancer will kill both androgen-responsive and androgen-refractory cancer cells. Whereas commonly used androgen deprivation therapies induce apoptotic cell death in androgen-sensitive cells (Colombel, M. C., et al., Methods Cell. Biol., 46, 27-34, 1995; Buttyan, R., et al., In: Prostate—Basic and Clinical Aspects., pp 201-218, Naz R K (ed), CRC Press, Boca Raton, 1997; Perlman, H., et al., Cell Death Differentiation 6, 48-54, 1999; Bruckleimer, E. M., et al., Sem. Oncol., 26, 382-398, 1999), effective chemotherapy for androgen-refractory cancer is not available (Kozlowski, J., et al., Urol. Clin. N. Am., 18, 15-24, 1991; Santen, R. J., J. Clin. Endocrinol. Metab., 75, 685-689, 1992; Kreis, W., Cancer Invest., 13, 296-312, 1995). It would be advantageous to have means of inducing cell death in all prostate cancer cell types, including both androgen-sensitive and androgen-refractory prostate cancer cells.

All references cited herein are hereby incorporated by reference in their entirety.

SUMMARY OF THE INVENTION

The invention provides compositions and methods for the administration of prostate cell-specific adenoviral vectors to an individual in need thereof, such as, an individual with prostate cancer.

Accordingly, in one aspect, the invention provides compositions and methods of suppressing prostate tumor growth in an individual comprising administering to the individual a composition comprising a replication-competent target cell-specific adenoviral vector wherein said vector comprises a DNA sequence encoding a chimera of an adenovirus gene essential for replication, specifically the E1A gene, and the gene encoding the androgen receptor (or a portion thereof) under transcriptional control of a target cell specific transcriptional regulatory element (TRE), wherein the adenoviral vector is administered in amounts sufficient to suppress prostate tumor growth Any TRE which directs prostate cell-specific expression can be used in the disclosed adenovirus vectors. TREs specific for prostate cancer cells include, the rat probasin (PB) TRE; prostate-specific antigen (PSA) TRE; the hK2 TRE, or any prostate specific promoter which contains an androgen responsive element.

In other embodiments, the chimera is comprised of sequences of the E1A gene and fragments of the androgen receptor gene, such as the transactivation domain and the DNA Binding Domain. In another embodiment, there is a single point mutation the full length amino acid sequence of the Androgen receptor in the E1A/AR chimeric protein. The single point mutation occurs at the codon 685 position, where cysteine is replaced by tyrosine, which results in a chimera activated by both androgens and nonsteroidal anti-androgens.

In still another embodiment, the E1A/Androgen receptor chimera can be inactivated by ansamycins, such as geldanamycin.

Other features and advantages of the invention will be apparent to those skilled in the art from the following detailed description and claims.

BRIEF DESCRIPTION OF THE DRAWINGS

FIG. 6 represents the DNA sequence encoding the EA1/AR (full length) chimeric protein, SEQ ID NO: 1.

FIG. 7 represents the DNA sequence encoding the EA1/Transactivation Domain (TAD) chimera protein, SEQ ID NO: 2.

FIG. 8 represents the DNA sequence encoding the EA1/DNA Binding Domain (DBD) chimera protein, SEQ ID NO: 3.

FIG. 9 represents the DNA sequence encoding the 12S/AR (full length) chimera protein, SEQ ID NO: 4.

FIG. 10 represents the DNA sequence encoding the 12S/TAD chimera protein, SEQ ID NO: 5.

FIG. 11 represents the DNA sequence encoding the 12S/DBD chimera protein, SEQ ID NO: 6.

FIG. 12 represents the amino acid sequence for the 12S/AR (full length) chimera protein, SEQ ID NO: 7.

FIG. 13 represents the amino acid sequence for the 12S/TAD chimera protein, SEQ ID NO: 8.

FIG. 14 represents the amino acid sequence for the 12S/DBD chimera protein, SEQ ID NO: 9.

FIG. 16 represents the cDNA sequence of EA1, SEQ ID NO: 10.

FIG. 17 represents the cDNA sequence of EA1/TAD chimera, SEQ ID NO: 11.

FIG. 18 represents the cDNA sequence of EA1/AR (full length) chimera, SEQ ID NO: 12.

FIG. 19 represents the cDNA sequence of EA1/AR (C685Y) chimera, SEQ ID NO: 13.

DETAILED DESCRIPTION OF THE INVENTION

Figure 1A:
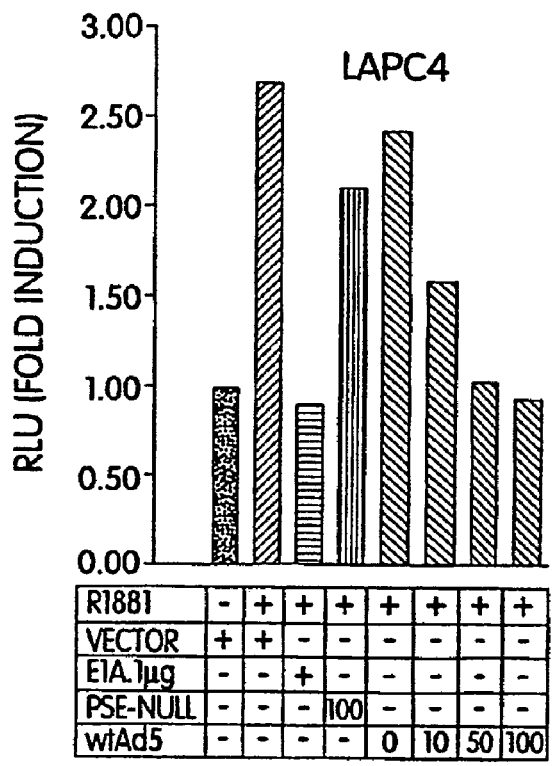
FIG. 1A is bar graph representations illustrating E1A inhibition of AR function in LAPC4; in A, E1A expressed either by plasmid in a cotransfection, or by virus in an early infection response causes a loss of AR inducibility for the target reporter pBK-PSE-PBN-LUC; Viral experiments were performed at varying multiplicities of infection, shown in the grids below the graph; B is bar graph representations illustrating the effect of E1A on expression of an AR dependent promoter construct in an AR negative cell line (PC3); note that the overall activity is diminished compared to LAPC4 and there is no significant effect of E1A expression either by plasmid or by virus on the target reporter pBK-PSE-PBN-LUC at this concentration of E1A plasmid (0.1 µg); because virus enhances plasmid DNA transfer efficiency, data are plotted as fold induction of RLU relative to the negative control.

We have discovered compositions and methods for enhancing the oncolytic activity of replication-competent, prostate cell-specific adenovirus vectors by modification of the E1A gene product. The target cell-specific replication-competent adenovirus vectors comprise a chimera of an adenovirus gene essential for replication, specifically the E1A gene, and the Androgen receptor (or a portion thereof) under the transcriptional control of a prostate cell-specific transcriptional regulatory element (TRE). By providing for cell type-specific transcription through the use of one or more cell type-specific TREs, the adenovirus vectors effect prostate-specific cytotoxicity due to selective replication.

The E1A gene inactivates androgen receptor function in prostatic epithelium. Since the androgen receptor is the major regulator of Prostate Specific Antigen promoter activity, conditional replicating adenoviruses, which contain androgen response elements (AREs), are not inducible by androgen. The present invention relates to the generation of E1A chimeric fusion proteins with fragments of the androgen receptor to yield multiple isoforms which are capable of activation of the AREs. The E1A/AR chimeras have several forms. Each form combines different isoforms of the E1A gene product and different domains of the androgen receptor, resulting in a family of chimeras which can be tailored to provide optimal activity of our prostate specific conditional replicating adenoviruses, including the recalcitrant androgen independent prostate cancers often seen in clinical practice.

Compositions of the present invention include, but are not limited to, the chimeric fusion genes in which E1a and the androgen receptor are combined so that the chimera would be capable of recognizing and activating any ARE containing promoter element. Such promoters include the PSA promoter and enhancer, the probasin promoter and the human glandular kallikrein promoter and enhancer. Depending on the chimeric protein used, these constructs can be made active in either androgen dependent or androgen independent disease.

In some embodiments, the methods provide for suppressing prostate tumor growth. In other embodiments, the methods are for reducing size and/or extent of a tumor. In other embodiments, the methods are for delaying development of a tumor. In other embodiments, the methods are for treating a neoplasia. In still other embodiments, the methods are for killing tumor cells.

With respect to all methods described herein, target prostate cells (i.e., neoplastic, proliferative cells) are contacted with an appropriate adenovirus vector described herein (preferably in the form of an adenovirus particle) such that the vector enters the cell and viral replication initiates.

Individuals suitable for treatment by these methods include individuals who have or are suspected of having prostate cancer, including individuals in the early or late stages of the disease, as well as individuals who have previously been treated or are about to undergo treatment (e.g., are in the adjuvant or neoadjuvant setting). Other individuals suitable for the methods described herein are those who are considered high risk for developing a prostate tumor, such as those who have a genetic predisposition to development of a neoplasia and/or who have been exposed to an agent(s) which is correlated with development of a neoplasia.

The presence of prostate cancer and the suitability of the individual for receiving the methods described herein may be determined by any of the techniques known in the art, including diagnostic methods such as imaging techniques, analysis of serum tumor markers, and biopsy.

The various compositions and methods of the invention will be described below. Certain embodiments of the methods use replication-competent prostate cell-specific adenoviral.

Although methods of tumor suppression are exemplified in the discussion below, it is understood that the alternative methods described above are equally applicable and suitable, and that the endpoints of these methods (e.g., efficacy of treatment) are measured using methods standard in the art, including the diagnostic and assessment methods described above.

General Techniques:

The practice of the present invention will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Felgner and Ringold (1989) Nature 337:387-388; Berkner and Sharp (1983) Nucl. Acids. Res. 11:6003-6020; Graham (1984) EMBO J. 3:2917-2922; Bett et al. (1993) J. Virology 67:5911-5921; Bett et al. (1994) Proc. Natl. Acad. Sci. USA 91:8802-8806.

DEFINITIONS

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

As used herein, "suppressing prostate tumor growth" refers to reducing the rate of growth of a tumor, halting tumor growth completely, causing a regression in the size of an existing tumor, eradicating an existing tumor and/or preventing the occurrence of additional tumors upon treatment with the compositions, kits or methods of the present invention. "Suppressing" tumor growth indicates a growth state that is curtailed when compared to growth without contact with, i.e., transfection by, an adenoviral vector Tumor cell growth can be assessed by any means known in the art, including, but not limited to, directly measuring tumor size, radiographic imaging, utilizing serum biomarkers of disease burden (e.g., serum PSA), determining whether tumor cells are proliferating using a $^3$H-thymidine incorporation assay, or counting tumor cells.

"Suppressing" prostate tumor cell growth means any or all of the following states: slowing, delaying, and stopping tumor growth, as well as tumor shrinkage.

"Delaying development" of a prostate tumor means to defer, hinder, slow, retard, stabilize, and/or postpone development of the disease. This delay can be of varying lengths of time, depending on the history of the disease and/or individual being treated.

As used herein, "synergy" or "synergistic effect" when referring to combination administration of adenovirus vector and antineoplastic agent and/or radiation means that the effect of the combination is more than additive when compared to administration of adenovirus vector, antineoplastic agent or radiation alone.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

As used herein, a "transcription response element" or "transcriptional regulatory element", or "TRE" is a polynucleotide sequence, preferably a DNA sequence, which increases transcription of an operably linked polynucleotide sequence in a host cell that allows that TRE to function. A TRE can comprise an enhancer and/or a promoter. A "transcriptional regulatory sequence" is a TRE. A "target cell-specific transcriptional response element" or "target cell-specific TRE" is a polynucleotide sequence, preferably a DNA sequence, which is preferentially functional in a specific type of cell, that is, a target cell. Accordingly, a target cell-specific TRE transcribes an operably linked polynucleotide sequence in a target cell that allows the target cell-specific TRE to function. The term "target cell-specific", as used herein, is intended to include cell type specificity, tissue specificity, developmental stage specificity, and tumor specificity, as well as specificity for a cancerous state of a given target cell. "Target cell-specific TRE" includes cell type-specific and cell status-specific TRE, as well as "composite" TREs. The term "composite TRE" includes a TRE which comprises both a cell type-specific and a cell status-specific TRE. A target cell-specific TRE can also include a heterologous component, including, for example, an SV40 or a cytomegalovirus (CMV) promoter(s). An example of a target cell specific TRE which is tissue specific is a CMV TRE which contains both promoter(s) and enhancer(s).

As described in more detail herein, a target cell-specific TRE can comprise any number of configurations, including, but not limited to, a target cell-specific promoter; and target cell-specific enhancer; a heterologous promoter and a target cell-specific enhancer; a target cell-specific promoter and a heterologous enhancer; a heterologous promoter and a heterologous enhancer; and multimers of the foregoing. The promoter and enhancer components of a target cell-specific TRE may be in any orientation and/or distance from the coding sequence of interest, as long as the desired target cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to) the target cell-specific TRE. As discussed herein, a target cell-specific TRE can be of varying lengths, and of varying sequence composition. As used herein, the term "cell status-specific TRE" is preferentially functional, i.e., confers transcriptional activation on an operably linked polynucleotide in a cell which allows a cell status-specific TRE to function, i.e., a cell which exhibits a particular physiological condition, including, but not limited to, an aberrant physiological state. "Cell status" thus refers to a given, or particular, physiological state (or condition) of a cell, which is reversible and/or progressive. The physiological state may be generated internally or externally; for example, it may be a metabolic state (such as in response to conditions of low oxygen), or it may be generated due to heat or ionizing radiation. "Cell status" is distinct from a "cell type", which relates to a differentiation state of a cell, which under normal conditions is irreversible. Generally (but not necessarily), as discussed herein, a cell status is embodied in an aberrant physiological state, for example, an oncological state.

Various combinations of transcriptional regulatory elements can be included in a vector. One or more may be heterologous. Further, one or more may have the tissue-specificity. For example, a single transcriptional regulatory element could be used to drive replication by more than one gene essential for replication. This is the case, for example, when the gene product of one of the genes drives transcription of the further gene(s). An example is a heterologous promoter linked to a cassette containing an E1a coding sequence (E1a promoter deleted) and the entire E1b gene. In such a cascade, only one heterologous transcriptional regulatory element may be necessary. When genes are individually (separately) controlled, however, more than one transcriptional regulatory sequence can be used if more than one such gene is desired to control replication.

A "functional portion" of a target cell-specific TRE is one which confers target cell-specific transcription on an operably linked gene or coding region, such that the operably linked gene or coding region is preferentially expressed in the target cells.

By "transcriptional activation" or an "increase in transcription," it is intended that transcription is increased above basal levels in the target cell (i.e., target cell) by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-target cell (i.e., a different cell type), or the level of activity (if any) of a reporter construct lacking a target cell-specific TRE as tested in a target cell line.

A "functionally-preserved variant" of a target cell-specific TRE is a target cell-specific TRE which differs from another target cell-specific TRE, but still retains target cell-specific transcription activity, although the degree of activation may be altered. The difference in a target cell-specific TRE can be due to differences in linear sequence, arising from, for example, single base mutation(s), addition(s), deletion(s), and/or modification(s) of the bases. The difference can also arise from changes in the sugar(s), and/or linkage(s) between the bases of a target cell-specific TRE. For example, certain point mutations within sequences of TREs have been shown to decrease transcription factor binding and stimulation of transcription. See Blackwood, et al. (1998) Science 281:60-63 and Smith et al. (1997) J. Biol. Chem. 272:27493-27496. One of skill in the art would recognize that some alterations of bases in and around transcription factor binding sites are more likely to negatively affect stimulation of transcription and cell-specificity, while alterations in bases which are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

As used herein, a TRE derived from a specific gene is referred to by the gene from which it was derived and is a polynucleotide sequence which regulates transcription of an operably linked polynucleotide sequence in a host cell that expresses said gene. For example, as used herein, a "human glandular kallikrein transcriptional regulatory element", or "hK2-TRE" is a polynucleotide sequence, preferably a DNA sequence, which increases transcription of an operably linked polynucleotide sequence in a host cell that allows an hk2-TRE to function, such as a cell (preferably a mammalian cell, even more preferably a human cell) that expresses androgen receptor, such as a prostate cell. An hk2-TRE is thus responsive to the binding of androgen receptor and comprises at least a portion of an hk2 promoter and/or an hk2 enhancer (i.e., the ARE or androgen receptor binding site).

As used herein, a "probasin (PB) transcriptional regulatory element", or "PB-TRE" is a polynucleotide sequence, preferably a DNA sequence, which selectively increases transcription of an operably-linked polynucleotide sequence in a host cell that allows a PB-TRE to function, such as a cell (preferably a mammalian cell, more preferably a human cell, even more preferably a prostate cell) that expresses androgen receptor. A PB-TRE is thus responsive to the binding of androgen receptor and comprises at least a portion of a PB promoter and/or a PB enhancer (i.e., the ARE or androgen receptor binding site).

As used herein, a "prostate-specific antigen (PSA) transcriptional regulatory element", or "PSA-TRE", or "PSE-TRE" is a polynucleotide sequence, preferably a DNA sequence, which selectively increases transcription of an operably linked polynucleotide sequence in a host cell that allows a PSA-TRE to function, such as a cell (preferably a mammalian cell, more preferably a human cell, even more preferably a prostate cell) that expresses androgen receptor. A PSA-TRE is thus responsive to the binding of androgen receptor and comprises at least a portion of a PSA promoter and/or a PSA enhancer (i.e., the ARE or androgen receptor binding site).

As used herein, a target cell-specific TRE can comprise any number of configurations, including, but not limited to, a target cell-specific promoter; a target cell-specific enhancer; a target cell-specific promoter and a target cell-specific enhancer; a target cell-specific promoter and a heterologous enhancer; a heterologous promoter and a target cell-specific enhancer; and multimers of the foregoing. The promoter and enhancer components of a target cell-specific TRE may be in any orientation and/or distance from the coding sequence of interest, as long as the desired target cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to) the target cell-specific TRE.

A "multicistronic transcript" refers to an mRNA molecule which contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions of polynucleotides are under transcriptional control of single transcriptional control element.

A "gene" refers to a coding region of a polynucleotide. A "gene" may or may not include non-coding sequences and/or regulatory elements.

"Replicating preferentially", as used herein, means that the adenovirus replicates more in a target cell than a non-target cell. Preferably, the adenovirus replicates at a significantly higher rate in target cells than non target cells; preferably, at least about 2-fold higher, preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1 \times 10^6$ higher. Most preferably, the adenovirus replicates solely in the target cells (that is, does not replicate or replicates at a very low levels in non-target cells).

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

The terms "polynucleotide" and "nucleic acid", used interchangeably herein, refer to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) Nucleic Acids Res. 24:1841-8; Chaturvedi et al. (1996) Nucleic Acids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Molec. Immunol. 32:1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in Current Protocols in Molecular Biology (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

The term "enhancer" is used according to its art-recognized meaning. It is intended to mean a sequence found in eukaryotes and certain eukaryotic viruses which can increase transcription from a gene when located (in either orientation) up to several kilobases from the gene being studied. These sequences usually act as enhancers when on the 5' side (upstream) of the gene in question. However, some enhancers are active when placed on the 3' side (downstream) of the gene. In some cases, enhancer elements can activate transcription from a gene with no (known) promoter.

The term "functional inactivation" is intended to mean a genetic lesion that prevents the normal activity of a gene product. Thus, functional inactivation could result from a mutation in the gene encoding the gene product. Such a lesion includes insertions, deletions, and base changes. Alternatively, functional inactivation may occur by the abnormal interaction of the normal gene product with one or more other cellular gene products which bind to or otherwise prevent the functional activity of said gene product. Thus, the gene product may be a protein produced from a normal gene but which cannot perform its ordinary and normal function because of an interaction with a second factor.

The term "gene essential for replication" refers to a genetic sequence whose transcription is required for the vector to replicate in the target cell.

The term "gene product" is intended to mean DNA, RNA, protein, peptides, or viral particles. Thus, the distribution, for the purposes of the invention, is of any of these components.

The term "heterologous" means a DNA sequence not found in the native vector genome. With respect to a "heterologous transcriptional regulatory sequence", "heterologous" indicates that the transcriptional regulatory sequence is not naturally ligated to the DNA sequence for the gene essential for replication of the vector.

The term "promoter" is used according to its art-recognized meaning. It is intended to mean the DNA region, usually upstream to the coding sequence of a gene or operon, which binds RNA polymerase and directs the enzyme to the correct transcriptional start site.

The term "replication" means duplication of a vector. This duplication, in the case of viruses, can occur at the level of nucleic acid, or at the level of infectious viral particle. In the case of DNA viruses, replication at the nucleic acid level comprises DNA replication. In the case of RNA viruses, nucleic acid replication comprises replication into plus or minus strand (or both). In the case if retroviruses, replication at the nucleic acid level includes the production of cDNA as well as the further production of RNA viral genomes. The essential feature is the generation of nucleic acid copies of the original viral vector. However, replication also includes the formation of infectious DNA or RNA viral particles. Such particles may successively infect cells in a given target tissue, thus distributing the vector through all or a significant portion of the target tissue.

The term "replication-conditional vector" refers to a vector which, when introduced into a tissue, will not replicate unless a transcriptional regulatory sequence in that vector is activated or derepressed in that tissue. That is, replication depends upon transcription by means of that transcriptional regulatory sequence. Such a vector is replication-conditional as described because it has been modified in the following manner. A gene that is essential for replication has been modified by replacing the transcriptional regulatory sequence on which transcription of that gene normally depends with a heterologous transcriptional regulatory sequence. This transcriptional regulatory sequence depends upon the presence of transcriptional regulatory factors or the absence of transcriptional regulatory inhibitors. The presence of these factors in a given tissue or the absence of such inhibitors in a given tissue provides the replication-conditionality. Accordingly, the native transcriptional regulatory sequence may be replaced with the heterologous transcriptional regulatory sequence. Alternatively, the native transcriptional regulatory sequence may be disabled or rendered dysfunctional by partial removal (deletion) or other mutation (one or more base changes, insertions, inversions, etc.).

The gene sequence may be a coding sequence. It may contain one or more open reading frames, as well as intron sequences. However, such a sequence is not limited to a coding sequence, but includes sequences that are transcribed into RNA, which RNA is itself essential for vector replication. The essential feature is that the transcription of the gene sequences does not depend on the native transcriptional regulatory sequences.

The term "silencer," used in its art-recognized sense, means a sequence found in eucaryotic viruses and eucaryotes which can decrease or silence transcription of a gene when located within several kilobases of that gene.

The term "tissue-specific" is intended to mean that the transcriptional regulatory sequence to which the gene essential for replication is operably linked functions specifically in that tissue so that replication proceeds in that tissue. This can occur by the presence in that tissue, and not in non-target tissues, of positive transcription factors that activate the transcriptional regulatory sequence. It can also occur by the absence of transcription inhibiting factors that normally occur in non-target tissues and prevent transcription as a result of the transcription regulatory sequence. Thus, when transcription occurs, it proceeds into the gene essential for replication such that in that target tissue, replication of the vector and its attendant functions occur.

As described herein, tissue specificity is particularly relevant in the treatment of the abnormal counterpart of a normal tissue. Such counterparts include, but are not limited to, cancerous prostate tissue and normal prostate tissue. Tissue specificity also includes the presence of an abnormal tissue type interspersed with normal tissue of a different tissue type, as for example in the case of metastases of prostate cancer, and the like, into tissue such as liver. In this case, the target tissue is the abnormal tissue, and tissue specificity reflects the restriction of vector replication to the abnormal tissue interspersed in the normal tissue. It is also to be understood that tissue specificity, in the context of treatment, is particularly relevant in vivo. However, as described herein, ex vivo treatment and tissue replacement also falls within the concept of tissue specificity according to the present invention.

An "E3 region" (used interchangeably with "E3") is a term well understood in the art and means the region of the adenoviral genome that encodes the E3 products (discussed herein). Generally, the E3 region is located between about 28583 and 30470 of the adenoviral genome. The E3 region has been described in various publications, including, for example, Wold et al. (1995) Curr. Topics Microbiol Immunol. 199:237-274.

A "portion" of the E3 region means less than the entire E3 region, and as such includes polynucleotide deletions as well as polynucleotides encoding one or more polypeptide products of the E3 region. As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; and uptake of molecules. "Cytotoxicity" includes cell death and/or cytolysis. Assays are known in the art which indicate cytotoxicity, such as dye exclusion, 3H-thymidine uptake, and plaque assays.

An "E1B 19-kDa region" (used interchangeably with "E1B 19-kDa genomic region") refers to the genomic region of the adenovirus E1B gene encoding the E1B 19-kDa product. According to wild-type Ad5, the E1B 19-kDa region is a 261 bp region located between nucleotide 1714 and nucleotide 2244. The E1B 19-kDa region has been described in, for example, Rao et al., Proc. Natl. Acad. Sci. USA, 89:7742-7746. The present invention encompasses deletion of part or all of the E1B 19-kDa region as well as embodiments wherein the E1B 19-kDa region is mutated, as long as the deletion or mutation lessens or eliminates the inhibition of apoptosis associated with E1B-19 kDa.

The term "selective cytotoxicity", as used herein, refers to the cytotoxicity conferred by an adenovirus vector of the present invention on a cell which allows or induces a target cell-specific TRE to function (a target cell) when compared to the cytotoxicity conferred by an adenoviral vector of the present invention on a cell which does not allow a target cell-specific TRE to function (a non-target cell). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector.

In the context of adenovirus, a "heterologous" promoter or enhancer is one which is not associated with or derived from an adenovirus gene.

In the context of adenovirus, an "endogenous" promoter, enhancer, or TRE is native to or derived from adenovirus. In the context of promoter, an "inactivation" means that there is a mutation of or deletion in part or all of the of the endogenous promoter, i.e., a modification or alteration of the endogenous promoter, such as, for example, a point mutation or insertion, which disables the function of the promoter.

In the context of a target cell-specific TRE, a "heterologous" promoter or enhancer is one which is derived from a gene other than the gene from which a reference target cell-specific TRE is derived.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

"Androgen receptor," or AR, as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones other than androgens. Encompassed in the term "androgen receptor" are mutant forms of an androgen receptor, such as those characterized by amino acid additions, insertions, truncations and deletions, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

A polynucleotide sequence that is "depicted in" a SEQ ID NO means that the sequence is present as an identical contiguous sequence in the SEQ ID NO. The term encompasses portions, or regions of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, rodents, primates, and pets An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

A given TRE is "derived from" a given gene if it is associated with that gene in nature.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

Adenoviral E1A Mediated Viral Replication:

Type 5 adenoviruses consist of roughly 36 kilobases encoding over 38 gene products. For convenience, the genes are categorized into early (E1-E4) and late (L1-L5) regions. The initiation of the replicative life cycle requires the E1 region, which encodes the E1A and E1B genes. E1A interacts with many proteins including the CREB binding protein (CBP), p300, pRB and related proteins p130 and p107, p400, TRAP, p60/cyclin A, p33 cdk2, BS69, CtBP, the TATA binding protein (TBP) and various other components of the TFIID complex (Virus Res 1995; 35:113-21, Biochem Cell Biol 1997; 75:95-102). These interactions account for many of the elucidated functions of E1A, including, but not limited to: chromatin remodeling, regulation of histone acetyltransferase, transcriptional activation, transcriptional repression, induction of DNA synthesis, and suppression of differentiation (Nat Rev Mol Cell Biol 2002; 3:441-52). In the appropriately susceptible host cell, E1A and E1B coordinate viral replication, with passive lysis of the cell and release of the viral progeny. Since the adenoviral DNA is maintained completely in the episomal state, infected cells either undergo apoptosis in an abortive infection, or viral replication followed by lysis.

Immediately after cellular infection, the E1 genes are transcribed and bind to a host of protein complexes. Although the order of binding is unclear, several key features are known. Firstly, E1A binds to p400 and TRAP, which have homology to the Swi/Snf family of ATP-dependent chromatin remodeling factors. These factors aid in regulating gene expression by allowing access to "euchromatin". E1A also binds to at least three protein complexes known to have significant histone acetyl transferase activity: p300, CREB binding protein (CBP) and PCAF. Active acetylation of certain histones (e.g., H3 and H4) is known to facilitate DNA unwinding and enhance gene expression by allowing easier access to transcription factors and co-activators. Hence, host transcription and replication is strongly down regulated and adenoviral transcription and replication is strongly up regulated.

E1A is known to both activate and inhibit certain transgene expression. There appear to be at least two different mechanisms by which this can occur (Nat Rev Mol Cell Biol 2002; 3:441-52; Oncogene 2001; 20:7824-35): (1) sequestration of chromatin remodeling/HAT complexes required by certain transcription factors; (2) active inhibition of certain trans-genes by direct binding of E1A with the transcription factor and the inhibitory complex C-terminal binding protein (CtBP). CBP/p300 and PCAF are not required for expression of all genes, but rather only a small subset of genes regulated by transcription factors thought to be most important in differentiation. Two-prostate specific oncolytic adenoviruses, CN706 (also known as CG7060) and CV787 (also known as CG7870) are unable to undergo androgen induction for enhanced oncolytic activity (Cancer Res 1999; 59:4200-3). This finding is surprising given that they are regulated by ARE containing promoters. In contrast, generation of an estrogen receptor dependent conditionally replication competent adenovirus, by placing a portion of the pS2 promoter upstream of the E1A gene, resulted in a viral construct whose oncolytic activity was markedly enhanced by estrogen and antagonized by anti-estrogen (Hum Gene Ther 2000; 2009-24). In that analysis, the addition of estrogen caused a marked increase in the E1A expression and this increase precisely correlated with the viral oncolytic activity in ER positive cells. Evolving data regarding E1A protein interactions suggest that E1A is able to interact directly with some members of the nuclear receptor family. E1A interaction with RAR-β augments its ability to stimulate ligand dependent activation of the RAR-β2 promoter (Mol Cell Biol 1995; 10:19-25); while in contrast, E1A interaction with RXR retinoic acid receptors obliterates retinoic acid(RA) induction of differentiation genes (Oncogene 1995; 10: 19-25). Notably, E1A directly binds to RAR-β (in the CR3 region), but does not bind RXR. Simply stated, E1A is capable of either up-regulating or down-regulating retinoic acid responsive target genes dependent on the particular target gene promoter and the nature of the retinoic acid receptor complex (RXR versus RAR). Given these findings, we hypothesized that the reason we did not see androgen induction in the early prostate specific oncolytic vectors was because E1A was specifically inhibiting AR activity, a finding we later confirmed.

Androgen Receptor Structure and Function:

The androgen receptor is a member of the nuclear receptor super-family, which is a group of ligand-inducible transcription factors. Like other steroid receptors, the structure of the androgen receptor is divided into three distinct, modular domains: the amino terminal domain, the DNA binding domain and the carboxy-terminal ligand binding domain (Vitam Horm 1994; 49:383-432). Binding of the steroid ligand results in activation of the androgen receptor and dissociation from the chaperonin complex (Hsp90, Hsp70, Hip, p60, p23, FKBP51, FKBP52 and Cyp40). Subsequently, the receptor undergoes dimerization, nuclear translocation and subsequent target gene activation (Annu Rev Med 1995; 46:443-53). Binding of androgen to the ligand-binding domain is required for activation; however, deletion of the entire ligand-binding domain can lead to a constitutively active androgen receptor. Interestingly, point mutations in the ligand-binding domain can result in altered steroid specificity. The best characterized of these is a single point mutation resulting in a threonine to alanine substitution at codon 868 identified in the LNCaP cell line (J Steroid Biochem Mol Biol 1994; 49:341-6), resulting in an AR which can be induced by progesterone as well as androgen. Conversion of codon 685 from a cysteine to a tyrosine results in an androgen receptor mutant which can be strongly activated with the nonsteroidal anti-androgen bicalutamide (Endocrine 2000; 12:69-76). Once the androgen receptor has achieved translocation into the nucleus, it must coordinate binding to a number of associated co-activators and co-repressors, which subsequently regulate gene expression. As the number of potential co-regulators clearly exceeds the capacity for direct interaction by a single receptor, the most likely scenario is that transcriptional activation by AR involves multiple factors that act in both a sequential and concomitant manner to reorganize chromatin templates, in a manner analogous to the adenoviral E1A. The precise timing and sequence of binding of these factors remains to be elucidated, however, one can generally break down the processes empirically into chromatin/nucleosomal remodeling (an energy dependent process), histone acetyltransferase activity, and subsequent recruitment of TATA binding protein associated factors (TAFs) all of which promote an increased rate of gene transcription by RNA polymerase II.

N-terminal deletions in region of codons 46-408 results in dominant negative suppression of hormone inducible transgene activation, indicating that the major co-activator functions require an interaction within that site. The major transactivating segment is referred to as the activator function-1 (AF-1), which is required for interaction with SRC-1. Maximal co-activation however, requires an interaction with the ligand binding domain LXXLL motif at the AF-2 site. The androgen receptor interacts with chromatin remodeling complexes in an ATP dependent fashion and this may be among the earliest steps in the ultimate regulation of certain target genes. Such complexes include the multisubunit human SWI-SNF complex, which has been shown to remodel mono-and polynucleosome templates. Since condensed chromatin renders genes inaccessible for transcription, the combination of a steroid receptor along with the SWI-SNF complex formation appears to be critical for appropriate nucleosomal remodeling to allow appropriate target genes to be accessible for gene regulation. Once the receptor SWI-SNF complex has successfully "opened" the structure of the chromatin to allow transcriptional regulation, the androgen receptor must interact with the HAT complexes p300/CBP and PCAF as well as a series of co-activators. Among the most important co-activators is the SRC-1, which has mild HAT activity and seems to be required for optimal stimulation of steroid dependent transcription. Additional factors include SRA (a structural RNA necessary for the coactivator complex to function optimally), and p160, which appears to be required for hormone dependent activation and appears to directly interact with the polyglutamine repeats found in the amino terminal transactivation domain. Maximal androgen receptor mediated transactivation requires an additional interaction with a large multi-protein complex referred to as TRAP (for thyroid receptor associated complex)/DRIP (for vitamin D Receptor interacting proteins)/ARC for activator-recruited cofactor complex. Though initially described for their interactions with the thyroid hormone receptor and vitamin D receptor, this complex is utilized by a variety of transcription factors, which stimulate RNA Pol II transcription, including the androgen receptor. In summary, binding of steroid ligand by the androgen receptor results in dissociation from the chaperonin complex, dimerization, post-translational modification, nuclear translocation, interactions with chromatin remodeling complexes, interactions with HAT complexes, interactions with numerous coactivator complexes, and interactions with complexes directly involved in initiation of transcription from the TFIID complex. As can be seen, there are distinct similarities between E1A interactions and the androgen receptor interactions, which led us to question whether E1A might differentially regulate AR action.

EA1/Androgen Receptor Chimeras:

The invention also provides chimeric or fusion nucleotides of the E1A and Androgen Receptor genes (or portions thereof) described herein. As used herein, a "chimeric gene" or "fusion gene" comprises genes of the invention operatively linked to heterologous genes sequences. "Heterologous gene sequences" includes a gene or polynucleotide having a sequence corresponding to a gene which is not substantially homologous to gene of the invention. Within the fusion gene, the term "operatively linked" is intended to indicate that the gene of the invention and the heterologous gene sequences are fused in-frame to each other. The heterologous gene sequences can be fused to the N-terminus or C-terminus of the corresponding peptide of the invention.

In various embodiments, the chimera is comprised of sequences of the E1A gene and fragments of the Androgen receptor gene, such as the transactivation domain and the DNA Binding Domain. In another embodiment, there is a single point mutation the full length amino acid sequence of the Androgen receptor in the E1A/AR chimeric protein. The single point mutation occurs at the codon 685 position, where cysteine is replaced by tyrosine, which results in a chimera activated by both androgens and nonsteroidal anti-androgens.

Preferably, a chimeric or fusion gene of the invention is produced by standard recombinant DNA techniques. For example, DNA fragments coding for the different peptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A peptide-encoding nucleic acid can be cloned into such an expression vector such that the fusion moiety is linked in-frame to the peptide.

Co-transfection assays of prostate cancer cell lines LNCaP and LAPC4 CMV-E1A-AR expressing plasmid or CMV-E1A expressing plasmid and luciferase reporter plasmid controlled by prostate specific promoter demonstrate that the expression of E1A completely inhibits the androgen receptor induction of the prostate specific promoter. This inhibitory effect of E1A on androgen receptor can be reversed by expression of E1A-AR. A similar effect can be observed in the assay using adenovirus infection, i.e. E1A expressing Ad5 can down-regulate the androgen receptor, and this inhibitory effect could be counteracted by E1A-AR expressing Ad5.

Other data demonstrate that either wild type E1A or its isoform 12S have the same inhibitory effect on the androgen receptor. Either full-length of androgen receptor or its truncated forms TAD-DBD (transactivation domain-DNA binding domain), or DBD (DNA binding domain) is able to counteract the inhibitory effect of E1A on androgen receptor. Each form of androgen receptor can display a unique profile of its specificity and potency in regulating the activity of the prostate specific promoter when it is in an E1A-AR fusion format. Different combinations of E1A-AR expressing adenoviral vectors could meet the need in the clinic of treatment for different types of prostate cancer (e.g. hormone-dependent cells or hormone-refractory cells). These cancer cell-tailored vectors will achieve a maximum therapeutic effect in the clinic. The nature of our vectors makes them different from and much better than the existing technologies for developing conditionally replicating adenoviruses in prostate cancer.

The adenoviral vector compositions and methods of the present invention and described herein are generally replication-competent, prostate-cell specific adenoviral vector comprising a chimera of an adenovirus gene essential for replication and the Androgen Receptor (and portions thereof) under transcriptional control of a TRE, embodiments of which are described infra. In one embodiment, the gene essential for replication in the adenoviral vector is an early gene, specifically E1A. In another embodiment E1A/AR chimera genes are under transcriptional control of non-identical (or heterologous) TREs. In some embodiments, the adenovirus vector E3 region is deleted.

The choice of adenoviral vector is primarily determined by the identity of the target cells, in this case prostate cells and therefore the type of cancer to be treated. As explained below in detail, an adenoviral vector comprising a PSA-TRE, PB-TRE, or hk2-TRE would preferentially replicate in prostate cells.

For example, with respect to treatment of prostate tumors, a replication-competent adenovirus in which a gene essential for replication, preferably one or more early genes, is under transcriptional control of a prostate specific TRE.

In some embodiments of the adenovirus vector, E1A is under transcriptional control of a prostate specific TRE. An example of a suitable prostate specific replication-competent adenoviral vector is one comprising probasin (PB)-TRE controlling transcription of E1A, and PSE-TRE controlling transcription of E1B, such as CG7870.

In some embodiments, a prostate specific adenoviral vector comprising a chimera of E1A and the Androgen receptor under transcriptional control of two non-identical prostate specific TREs. In some embodiments, the prostate specific TRE controlling transcription of E1A/Androgen Receptor chimera are heterologous (i.e., of different sequence) with respect to each other. In some embodiments, the prostate specific TRE controlling transcription of the E1A/Androgen Receptor chimera is derived from probasin (PB) and prostate specific antigen (PSA).

The adenoviral vectors used in the methods described herein are replication-competent target-cell specific adenoviral vectors comprising an adenovirus gene, preferably a gene essential for replication under transcriptional control of a target cell specific TRE. The vector may or may not include an E3 region. In other embodiments, an adenovirus vector is a replication competent, target cell specific vector comprising E1B, wherein E1B may have a deletion of part or the entire 19-kDa region.

The adenovirus vectors used in this invention replicate preferentially in TRE functional cells referred to herein as prostate cells. This replication preference is indicated by comparing the level of replication (i.e., titer) in prostate cells in which the TRE is active to the level of replication in cells in which the TRE is not active (i.e., a non-target cell). The replication preference is even more significant, as the adenovirus vectors used in the invention actually replicate at a significantly lower rate in TRE non-functional cells than wild type virus. Comparison of the adenovirus titer of a target cell to the titer of a TRE inactive cell type provides a key indication that the overall replication preference is enhanced due to the replication in target cells as well as depressed replication in non-target cells. This is especially useful in the cancer context, in which targeted cell killing is desirable. The TRE's preferably control genes necessary for replication, where the gene(s) necessary for replication is an early gene(s) of the adenovirus, preferentially the E1A gene.

Runaway infection is prevented due to the cell-specific requirements for viral replication. Without wishing to be bound by any particular theory, production of adenovirus proteins can serve to activate and/or stimulate the immune system, either generally or specifically toward target cells producing adenoviral proteins which can be an important consideration in the cancer context, where individuals are often moderately to severely immunocompromised.

In particular embodiments, the adenoviral vector may be a replication-competent target-cell specific adenoviral vector where the vector comprises an adenoviral gene. In one embodiment, the adenoviral gene is essential for replication and is under transcriptional control of a target cell-specific TRE.

In certain embodiments, the adenoviral vector may be a replication-competent target-cell specific adenoviral vector wherein the gene essential for replication is an early gene. In other embodiments the gene essential for replication may be a late gene.

In some embodiments of the adenovirus vector, E1A has a mutation in or deletion of its endogenous promoter. In some embodiments, E1A has a mutation in or deletion of its endogenous enhancer.

In particular preferred embodiments, the target cell specific adenoviral vector is specific for target cells of the prostate.

In certain preferred embodiments, the adenoviral gene(s) essential for replication is under the control of a TRE(s) such as, but not limited to PB-TRE, PSA-TRE, hk2-TRE, as described herein.

Transcriptional Response Elements (TREs):

The adenovirus vectors of the invention comprise target cell specific TREs which direct preferential expression of an operatively linked gene (or genes) in a particular target cell. A TRE can be tissue-specific, tumor-specific, developmental stage-specific, cell status specific, etc., depending on the type of cell present in the prostate tumor.

Cell- and tissue-specific transcriptional regulatory elements, as well as methods for their identification, isolation, characterization, genetic manipulation and use for regulation of operatively linked coding sequences, are well known in the art. A TRE can be derived from the transcriptional regulatory sequences of a single gene, or sequences from different genes can be combined to produce a functional TRE. A cell-specific TRE is preferentially functional in a limited population (or type) of cells, e.g., prostate cells. Accordingly, in some embodiments, the TRE used is preferentially functional in any of the prostate cell types.

As is known in the art, activity of TREs can be inducible. Inducible TREs generally exhibit low activity in the absence of inducer, and are up-regulated in the presence of inducer. Inducers include, for example, nucleic acids, polypeptides, small molecules, organic compounds and/or environmental conditions such as temperature, pressure or hypoxia. Inducible TREs may be preferred when expression is desired only at certain times or at certain locations, or when it is desirable to titrate the level of expression using an inducing agent. For example, transcriptional activity from the PSA-TRE, PB-TRE and hk2-TRE is inducible by androgen, as described herein and in PCT/US98/04080. Accordingly, in one embodiment of the present invention, an adenovirus vector comprises an inducible heterologous TRE.

TRE multimers are also useful in the disclosed vectors. For example, a TRE can comprise a tandem series of at least two, at least three, at least four, or at least five promoter fragments. Alternatively, a TRE can comprise one or more promoter regions along with one or more enhancer regions. TRE multimers can also comprise promoter and/or enhancer sequences from different genes. The promoter and enhancer components of a TRE can be in any orientation with respect to each other and can be in any orientation and/or any distance from the coding sequence of interest, as long as the desired cell-specific transcriptional activity is obtained.

The disclosed vectors are designed such that replication is preferentially enhanced in target cells in which the TRE(s) is (are) functional. More than one TRE can be present in a vector, as long as the TREs are functional in the same target cell.

A TRE for use in the present vectors may or may not comprise a silencer. The presence of a silencer (i.e., a negative regulatory element known in the art) can assist in shutting off transcription (and thus replication) in non-target cells. Thus, presence of a silencer can confer enhanced cell-specific vector replication by more effectively preventing replication in non-target cells. Alternatively, lack of a silencer may stimulate replication in target cells, thus conferring enhanced target cell-specificity.

As is readily appreciated by one skilled in the art, a TRE is a polynucleotide sequence, and, as such, can exhibit function over a variety of sequence permutations. Methods of nucleotide substitution, addition, and deletion are known in the art, and readily-available functional assays (such as the CAT or luciferase reporter gene assay) allow one of ordinary skill to determine whether a sequence variant exhibits requisite cell-specific transcription regulatory function. Hence, functionally preserved variants of TREs, comprising nucleic acid substitutions, additions, and/or deletions, can be used in the vectors disclosed herein. Accordingly, variant TREs retain function in the target cell but need not exhibit maximal function. In fact, maximal transcriptional activation activity of a TRE may not always be necessary to achieve a desired result, and the level of induction afforded by a fragment of a TRE may be sufficient for certain applications. For example, if used for treatment or palliation of prostate cancer, less-than-maximal responsiveness may be sufficient if, for example, the prostate cells are at an early stage of the disease.

Certain base modifications may result in enhanced expression levels and/or cell-specificity. For example, nucleic acid sequence deletions or additions within a TRE can move transcription regulatory protein binding sites closer or farther away from each other than they exist in their normal configuration, or rotate them so they are on opposite sides of the DNA helix, thereby altering spatial relationship among TRE-bound transcription factors, resulting in a decrease or increase in transcription, as is known in the art. In one embodiment, the invention provides for certain modifications of a TRE that will result in modulated expression levels as directed by the TRE, including enhanced cell-specificity. Achievement of enhanced expression levels may be especially desirable in the case of more aggressive forms of neoplastic growth, and/or when a more rapid and/or aggressive pattern of cell killing is warranted (for example, in an immunocompromised individual).

Transcriptional activity directed by a TRE (including both inhibition and enhancement) can be measured in a number of ways known in the art (and described in more detail below), but is generally measured by detection and/or quantitation of mRNA and/or of a protein product encoded by the sequence under control of (i.e., operably linked to) a TRE.

As discussed herein, a TRE can be of varying lengths, and of varying sequence composition. The size of a heterologous TRE will be determined in part by the capacity of the viral vector, which in turn depends upon the contemplated form of the vector (see infra). Generally minimal sizes are preferred for TREs, as this provides potential room for insertion of other sequences which may be desirable.

To minimize non-specific replication, endogenous (e.g., adenovirus) TREs are preferably removed from the vector. Besides facilitating target cell-specific replication, removal of endogenous TREs also provides greater insert capacity in a vector, which may be of special concern if an adenoviral vector is to be packaged within a virus particle. Even more importantly, deletion of endogenous TREs prevents the possibility of a recombination event whereby a heterologous TRE is deleted and the endogenous TRE assumes transcriptional control of its respective adenovirus coding sequences (thus allowing non-specific replication). In one embodiment, an adenoviral vector is constructed such that the endogenous transcription control sequences of adenoviral genes are deleted and replaced by one or more heterologous TREs. However, endogenous TREs can be maintained in the adenovirus vector(s), provided that sufficient cell-specific replication preference is preserved. These embodiments are constructed by inserting heterologous TREs between an endogenous TRE and a replication gene coding segment. Requisite cell-specific replication preference is determined by conducting assays that compare replication of the adenovirus vector in a cell which allows function of the heterologous TREs with replication in a cell which does not.

Generally, a TRE will increase replication of a vector in a target cell by at least about 2-fold, preferably at least about 5-fold, preferably at least about 10-fold more preferably at least about 20-fold, more preferably at least about 50-fold, more preferably at least about 100-fold, more preferably at least about 200-fold, even more preferably at least about 400- to about 500-fold, even more preferably at least about 1000-fold, compared to basal levels of replication in the absence of a TRE. The acceptable differential can be determined empirically (by measurement of mRNA levels using, for example, RNA blot assays, RNase protection assays or other assays known in the art) and will depend upon the anticipated use of the vector and/or the desired result.

Replication-competent adenovirus vectors directed at prostate cells can be generated using TREs that are preferentially functional in a target cell. In one embodiment of the present invention, the prostate cell is a tumor cell. Non-limiting examples of tumor cell-specific heterologous TREs, and their respective target cells, include: probasin (PB), target cell prostate cancer (PCT/US98/04132). Methods for identification, isolation, characterization and utilization of additional target cell-specific TREs are readily available to those of skill in the art.

In one embodiment of the present invention, a target cell-specific, heterologous TRE is tumor cell-specific. A vector can comprise a single tumor cell-specific TRE or multiple heterologous TREs which are tumor cell-specific and functional in the same cell. In another embodiment, a vector comprises one or more heterologous TREs which are tumor cell-specific and additionally comprises one or more heterologous TREs which are tissue specific, whereby all TREs are functional in the same cell.

Prostate-Specific TREs:

In one embodiment, adenovirus vectors comprise heterologous TREs that are prostate cell specific. For example, TREs that function preferentially in prostate cells and can be used to target adenovirus replication to prostate neoplasia, include, but are not limited to, TREs derived from the prostate-specific antigen gene (PSA-TRE) (Henderson U.S. Pat. No. 5,698, 443); the glandular kallikrein-1 gene (from the human gene, hk2-TRE) (PCT US98/16312), and the probasin gene (PB-TRE) (PCT/US98/04132). All three of these genes are preferentially expressed in prostate cells and their expression is androgen-inducible. Generally, expression of genes responsive to androgen induction is mediated by an androgen receptor (AR).

Prostate-Specific Antigen (PSA)

PSA is synthesized exclusively in prostatic epithelial cells and is synthesized in these cells whether they are normal, hyperplastic, or malignant. This tissue-specific expression of PSA has made it an excellent biomarker for benign prostatic hyperplasia (BPH) and prostatic carcinoma (CaP). Normal serum levels of PSA are typically below 5 ng/ml, with elevated levels indicative of BPH or CaP. Lundwall et al. (1987) FEBS Lett. 214:317; Lundwall (1989) Biochem. Biophys. Res. Comm. 161:1151; and Riegmann et al. (1991) Molec. Endocrin. 5:1921.

The region of the PSA gene that provides androgen-dependent cell specificity, particularly in prostate cells, involves approximately 6.0 kilobases (kb). Schuur et al. (1996) J. Biol. Chem. 271:7043-7051. An enhancer region of approximately 1.5 kb in humans is located between nt, −5322 and nt −3739, relative to the transcription start site of the PSA gene. Within these enhancer sequences is an androgen response element (ARE) a sequence which binds androgen receptor. The sequence coordinates of the PSA promoter are from about nt −540 to nt +8 relative to the transcription start site. Juxtapositioning of the enhancer and promoter yields a fully functional, minimal prostate-specific TRE (PSA-TRE). Other portions of this approximately 6.0 kb region of the PSA gene can be used in the vectors described herein, as long as requisite functionality is maintained.

Human Glandular Kallikrein (hk2)

Human glandular kallikrein (hk2, located on 19q13 and encoding the KLK2 protein) is expressed exclusively in the prostate and its expression is up-regulated by androgens, primarily through transcriptional activation. Wolf et al. (1992) Molec. Endocrinol. 6:753-762; Morris (1989) Clin. Exp. Pharm. Physiol. 16:345-351; Qui et al. (1990) J. Urol. 144:1550-1556; and Young et al. (1992) Biochem. 31:818-824. The levels of hK2 found in various tumors and in the serum of patients with prostate cancer indicate that hK2 antigen may be a significant marker for prostate cancer. Charlesworth et al. (1997) Urology 49:487-493. Expression of hK2 has been detected in each of 257 radical prostatectomy specimens analyzed. Darson et al. (1997) Urology 49:857-862. The intensity and extent of hK2 expression, detected using specific antibodies, was observed to increase from benign epithelium to high-grade prostatic intraepithelial neoplasia (PIN) and adenocarcinoma.

The activity of the hk2 promoter has been described and a region up to nt −2256 relative to the transcription start site was previously disclosed. Schedlich et al. (1987) DNA 6:429-437. The hk2 promoter is androgen responsive and, in plasmid constructs wherein the promoter alone controls the expression of a reporter gene, expression of the reporter gene is increased approximately 10-fold in the presence of androgen. Murtha et al. (1993) Biochem. 32:6459-6464. hk2 enhancer activity is found within a polynucleotide sequence approximately nt −12,014 to nt −2257 relative to the start of transcription and, when this sequence is operably linked to an hk2 promoter and a reporter gene, transcription of operably-linked sequences in prostate cells increases in the presence of androgen to levels approximately 30-fold to approximately 100-fold greater than the level of transcription in the absence of androgen. This induction is generally independent of the orientation and position of the enhancer sequences. Enhancer activity has also been demonstrated in the following regions (all relative to the transcription start site): about nt −3993 to about nt −3643, about nt −4814 to about nt −3643, about nt −5155 to about nt −3387, about nt −6038 to about nt −2394.

Thus, an hk2 enhancer can be operably linked to an hk2 promoter or a heterologous promoter to form a hk2 transcriptional regulatory element (hk2-TRE). A hk2-TRE can then be operably linked to a heterologous polynucleotide to confer hk2-TRE-specific transcriptional regulation on the linked gene, thus increasing its expression.

Probasin

The rat probasin (PB) gene encodes an androgen and zinc-regulated protein first characterized in the dorsolateral prostate of the rat. Dodd et al. (1983) J. Biol. Chem. 258:10731-10737; Matusik et al. (1986) Biochem. Cell. Biol. 64:601-607; and Sweetland et al. (1988) Mol. Cell. Biochem. 84:3-15. The dorsolateral lobes of the murine prostate are considered the most homologous to the peripheral zone of the human prostate, where approximately 68% of human prostate cancers are thought to originate.

A PB-TRE has been shown to exist in an approximately 0.5 kb fragment of sequence upstream of the probasin coding sequence, from about nt −426 to about nt +28 relative to the transcription start site. This minimal promoter sequence from the PB gene appears to provide sufficient information to direct prostate-specific developmental—and hormone—regulated expression of an operably linked heterologous gene in transgenic mice. Greenberg et al. (1994) Mol. Endocrinol. 8:230-239.

Reporter Genes:

A target cell-specific TRE can be introduced into an adenovirus vector immediately upstream of and operably linked to an early gene such as E1A/AR chimera. The second gene may be a reporter gene. The reporter gene can encode a reporter protein, including, but not limited to, chloramphenicol acetyl transferase (CAT), beta-galactosidase (encoded by the lacZ gene), luciferase, alkaline phosphatase, a green fluorescent protein, and horse radish peroxidase. For detection of a putative cancer cell(s) in a biological sample, the biological sample may be treated with modified adenoviruses in which a reporter gene (e.g., luciferase) is under control of a target cell-specific TRE. The target cell-specific TRE will be transcriptionally active in cells that allow the target cell-specific TRE to function and luciferase will be produced. This production will allow detection of target cells, including cancer cells in, for example, a human host or a biological sample. Alternatively, an adenovirus can be constructed in which a gene encoding a product conditionally required for survival (e.g., an antibiotic resistance marker) is under transcriptional control of a target cell-specific TRE. When this adenovirus is introduced into a biological sample, the target cells will become antibiotic resistant. An antibiotic can then be introduced into the medium to kill the non-cancerous cells.

Preparation of the Adenovirus Vectors:

The adenovirus vectors of this invention can be prepared using recombinant techniques that are standard in the art. Generally, a target cell-specific TRE is inserted 5' to the adenoviral gene of interest, preferably an adenoviral replication gene, more preferably one or more early replication genes (although late gene(s) can be used). A target cell-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for a target cell-specific TRE. Accordingly, convenient restriction sites for annealing (i.e., inserting) a target cell-specific TRE can be engineered onto the 5' and 3' ends of a UP-TRE using standard recombinant methods, such as PCR.

Polynucleotides used for making adenoviral vectors of this invention may be obtained using standard methods in the art, such as chemical synthesis, recombinant methods and/or obtained from biological sources.

Adenoviral vectors containing all replication-essential elements, with the desired elements (e.g., E1A) under control of a target cell-specific TRE, are conveniently prepared by homologous recombination or in vitro ligation of two plasmids, one providing the left-hand portion of adenovirus and the other plasmid providing the right-hand region, one or more of which contains at least one adenovirus gene under control of a target cell-specific TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from a target cell-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) Nucleic Acid Research 11:6003-6020; Bridge et al. (1989) J. Virol. 63:631-638.

For convenience, plasmids are available that provide the necessary portions of adenovirus. Plasmid pXC.1 (McKinnon (1982) Gene 19:33-42) contains the wild-type left-hand end of Ad5. pBHG10 (Bett et al. (1994); Microbix Biosystems Inc., Toronto) provides the right-hand end of Ad5, with a deletion in E3. The deletion in E3 provides room in the virus to insert a 3 kb target cell-specific TRE without deleting the endogenous enhancer/promoter. The gene for E3 is located on the opposite strand from E4 (r-strand). PBHG11 provides an even larger E3 deletion (an additional 0.3 kb is deleted). Bett et al. (1994). Alternatively, the use of pBHGE3 (Microbix Biosystems, Inc.) provides the right hand end of Ad5, with a full-length of E3.

For manipulation of the early genes, the transcription start site of Ad5 E1A is at 498 and the ATG start site of the E1A coding segment is at 560 in the virus genome. This region can be used for insertion of a target cell-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of target cell-specific TRE at that site.

A similar strategy may also be used for insertion of a target cell-specific TRE element to regulate E1B. The E1B promoter of Ad5 consists of a single high-affinity recognition site for Sp1 and a TATA box. This region extends from Ad5 nt 1636 to 1701. By insertion of a target cell-specific TRE in this region, one can provide for cell-specific transcription of the E1B gene. By employing the left-hand region modified with the cell-specific response element regulating E1A, as the template for introducing a target cell-specific TRE to regulate E1B, the resulting adenovirus vector will be dependent upon the cell-specific transcription factors for expression of both E1A and E1B. In some embodiments, part or all of the 19-kDa region of E1B is deleted.

Adenoviral constructs containing an E3 region can be generated wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 region can be introduced into cells, for example 293 cells, along with an adenoviral construct or an adenoviral plasmid construct, where they can undergo homologous recombination to yield adenovirus containing an E3 region. In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Methods of packaging polynucleotides into adenovirus particles are known in the art and are also described in PCT PCT/US98/04080.

The following examples are offered by way of illustration and should not be considered as limiting the scope of the invention. The specific examples exemplify the adenovirus 5 serotype, however, persons skilled in the art will realize these techniques may be applied to other adenoviral serotypes Delivery of Adenoviruses:

Delivery of adenoviral vectors is discussed infra and is generally accomplished by either site-specific injection or intravenously. Direct intra-prostatic injections are preferred. Site-specific injections of either vector may include, for example, injections into the portal vein of the liver as well as intraperitoneal, intrapleural, intrathecal, intra-arterial, intra-tumor injections or topical application. These methods are easily accommodated in treatments using adenoviral vectors.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are to be transfected or transformed in vitro or in vivo). If used as a packaged adenovirus, adenovirus vectors may be administered in an appropriate physiologically acceptable carrier at a dose of about 1 to about 10. The multiplicity of infection will generally be in the range of about 0.001 to 100. If administered as a polynucleotide construct (i.e., not packaged as a virus) about 0.01 ug to about 1000 ug of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Administration of the above-described methods may also include repeat doses or courses of target-cell specific adenovirus depending, inter alia, upon the individual's response and the characteristics of the individual's disease. Repeat doses may be undertaken immediately following the first course of treatment (i.e., within one day), or after an interval of days, weeks or months to achieve and/or maintain suppression of tumor growth. A particular course of treatment according to the above-described methods, for example, adenoviral therapy, may later be followed by a course of combined or separate radiation and adenoviral therapy.

Generally, an effective amount of adenovirus vector is administered, i.e., amounts sufficient to achieve the desired result, based on general empirical knowledge of a population's response to such amounts. Some individuals are refractory to these treatments, and it is understood that the methods encompass administration to these individuals. The amount to be given depends, inter alia, on the stage of prostate cancer, the condition of the individual, the extent of disease, the route of administration, how many doses will be administered, and the desired objective.

Methods of Treating Prostate Cancer:

One aspect of the invention pertains to a method for treating prostate cancer in a subject in need of such treatment, comprising administering to the subject a adenoviral particle of the invention, and performing on the subject at least one procedure that removes or destroys prostatic tumor tissue, such as a radical prostatectomy, cryosurgery, external radiation therapy (e.g., X-ray therapy) or interstitial radiation therapy (e.g., implantation of a radioactive seed). The adenoviral particle may be administered to the subject prior to or subsequent to performing the procedure that removes or destroys pro static tumor tissue. In one such embodiment, administration of an adenoviral particle is preferably for a period sufficient to cause the prostate or prostatic tumor tissue to shrink in size prior to performing the procedure that removes or destroys prostatic tumor tissue. A suitable period for preadministration of an adenoviral particle typically is between about one day and about one year, more preferably between about three days and about six months.

In certain situations it may be desirable to use an antiandrogen, and thus in another embodiment, this treatment method can further involve administering an antiandrogen to the subject in combination with the adenoviral particle. In yet another embodiment, this treatment method can further involve administering one or more inhibitors of sex steroid biosynthesis to the subject in combination with the peptide compound (optionally in further combination with an antiandrogen) prior to or subsequent to performing the procedure that removes or destroys prostatic tumor tissue.

In another embodiment, the adenoviral particle of the present invention may be administered in conjunction with an LHRH agonist, as described in U.S. Pat. Nos. 5,843,902, 5,780,435, and 6,153,586, incorporated herein by reference, or an LH receptor antagonist.

Those of skill in the art will recognize that while it may not be necessary to combine adenoviral particle therapy with additional drugs or treatments, in certain situation it may be desirable to further combine the compound with other drugs or treatments to achieve the greatest therapeutic effect.

The methods of the present invention can be applied to the treatment of prostate cancer in male subjects at any stage of the cancer, although certain treatment methods are more preferred for particular cancer stages. For reviews on screening and diagnostic methods for prostate cancer, see e.g., Garnick, M. (1993) Annals of Internal Medicine 118:803-818; and Garnick, M. (1994) Scientific American 270:72-81. Prostate cancer is commonly evaluated according to a scale divided into four lettered stages: A, B, C and D. Tumors in stage A are microscopic; stage $A_1$ designates tumors confined to a relatively small area and composed of well-differentiated tissue, while stage $A_2$ tumors are more diffuse and less well differentiated. Stage B tumors are large enough to be felt during a rectal examination, while stage C prostate cancers have spread throughout the gland and typically have pushed past the borders of the prostate into surrounding structures. Stage D tumors have metastasized, e.g., to lymph nodes, bone, or other organs. Alternatively, tumors can be staged by the TNM staging system, in which tumors are ranked on a scale of progressively worsening disease from T1a to T4 (e.g., T1c tumors are non-palpable and non-visible that were detected by elevated blood levels of prostate specific antigen). The methods of the invention are useful in the treatment of any stage of prostate cancer. However, it will be appreciated by the skilled artisan that methods involving procedures for removal or destruction of prostatic tumor tissue preferably are employed with non-metastasized cancers. For example, radical prostatectomy preferably is used with stage A, B and some stage C tumors (i.e., where the tumor growth has not extended considerably beyond the borders of the prostate gland) as well as stage T1c tumors. Radiation therapy (e.g., external or interstitial) preferably is used with stage A, B or C tumors as well as T1c tumors.

To assess the efficacy of a treatment method of the invention, the size of the prostate can be determined by methods known in the art, for example, rectal examination, transrectal ultrasonography or magnetic resonance imaging (MRI). Moreover, the size or extent of the prostate tumor (and metastatic tumors, if any) can be assessed by known methods including a prostate-specific antigen blood test (described further below), bone scanning, X-rays, skeletal survey, intravenous pyelography, CAT-scan, MRI, physical examination, biopsy, and the like. For treatment methods that involve surgery (e.g., in neoadjuvant therapy wherein an adenoviral particle is administered prior to a radical prostatectomy), the tumor can also be staged during surgery (e.g., the prostate gland can be examined during surgery and/or a biopsy can be taken and examined). Thus, clinical staging and/or surgical staging may be used to evaluate the extent of disease. Use of an adenoviral particle in accordance with the methods of the invention is expected to result in a tumor stage, which is improved compared to methodologies that do not include use of an adenoviral particle of the invention.

A preferred method of evaluating the extent of prostate cancer is to assay the level of prostate-specific antigen (PSA) in a subject's blood. The PSA blood test is a reasonably specific, sensitive, rapid, and inexpensive tool for screening for prostate cancer. In general, a blood PSA level above 4 ng/ml is considered to be suggestive of the presence of prostate cancer, with levels above 10 ng/ml being particularly indicative of cancer. For a subject undergoing treatment with an adenoviral particle, according to the methods of the invention, a pretreatment level of PSA can be established and the efficacy of the treatment assessed by monitoring periodically the PSA level in the subject's blood, wherein decreased PSA levels are used as an indicator of the efficacy of the treatment. The PSA nadir (i.e., the point at which PSA levels do not decrease further even upon further treatment with a peptide compound) can be used as the indicator point for initiation of a second therapy, for example for performance of a procedure that removes or destroys prostatic tumor tissue (such as radical prostatectomy, cryosurgery and/or radiation therapy). It is expected that the PSA nadir will be reached sooner using an adenoviral treatment, as compared to treatments which do not include using an adenoviral treatment.

The response criteria for prostate developed by the National Prostate Cancer Project (see e.g., The Prostate, 1:375-382) can also be used to assess the efficacy of treatment. For treatment methods involving a procedure that removes or destroys tumor tissue (such as radical prostatectomy, cryosurgery, and/or radiation therapy), it is preferable to administer oncolytic adenoviral therpay until the size of the prostate or a prostate tumor has decreased and/or blood PSA levels have decreased before performing the procedure.

Cessation of Viral Replication

Conditionally replication competent adenoviruses currently do not have any active means of inhibiting the replicative cycle, other than those mechanisms utilized by the host. While the host immune system is capable of reversing such infections, some patients may have varying degrees of immunocompetence. In certain situations, it may be possible that an infection proceeds in a fashion which is detrimental to the patient. In such a circumstance, having the ability to immediately halt an active replicative cycle would be highly desirable. The androgen receptor, as described above, is regulated in part by its associations with certain chaperoning, including hsp90. Certain compounds, including the ansamycins (of which geldanamycin is prototypical), are capable of inhibiting hsp90 and result in the immediate inactivation of those proteins which are found to be complexed to that chaperonin. The androgen receptor is such a protein, as is the E1A-AR chimeras described in this invention. Addition of geldanamycin results in the immediate inactivation of the E1A-AR chimeras, and immediately halts viral replication of those constructs based on these chimeras. Since at least two ansamycins (geldanamycin and 17-AAG also known as 17-allylamino-17-demethoxygeldanamycin) are currently in clinical trials, this strategy provides a novel "off-switch" for tissue specific replication competent adenoviral therapy.

Other Potential Uses of E1A Nuclear Receptor Chimeras

Although the methods of the invention are described in particular with application to the treatment of prostate cancer, it will be appreciated by the skilled artisan that these methods also can be applied to the treatment of other disorders, including other cancers. For example, a chimeric fusion of the E1A gene with other nuclear receptors such as the estrogen receptor, progesterone receptor, thyroid hormone receptor or retinoic acid receptor, may allow differential regulation of certain promoters which would markedly enhance tissue specific replication in a ligand dependent fashion. Such an approach could prove highly efficacious for breast cancer, thyroid cancer or any other cancer which relies upon a particular nuclear receptor for part of its development or propagation. The paradigm would be similar to the one described for the androgen receptor and its relationship to prostate cancer.

This invention is further illustrated by the following examples which should not be construed as limiting. The contents of all references, patents, and published patent applications cited throughout this application, as well as the figures and the sequence listing, are incorporated herein by reference.

EXAMPLES

Materials and Methods

Unless indicated otherwise, the following materials and methods were used in the subsequent examples.

Cells and Cell Culture. LNCaP, LAPC4 and PC3, DU145 are human prostate cancer cell lines. Hela 3S is a human cervical cancer cell line. All were obtained from ATCC (Manassas, Va.). LNCaP, PC3 and DU145 were maintained in RPMI medium supplemented with 10% FBS. Hela 3S and 293 cells (Quantum Biotech) were maintained in Dulbecco's MEM with 10% FBS. LAPC4 was maintained in ISCOVE's medium with 10% FBS and 1 nM R1881. All cells were maintained at 37° C. in an atmosphere containing 5% $CO_2$.

Plasmid Construction. E1A fragment was synthesized (approximately 1 kb) from the wild type adenovirus type 5 by PCR using the primer pair of 5'-TCACTCGGATACCAC-CGGGACTGAAAATGAGACATAT (SID NO: 14) and 5'-TACATCACTC GCGGCCGCTGGCCTGGGGCGTT-TACAGCTGA(SID NO: 15). This E1A product was cloned into the vector pCR2.1.-TOPO (Invitrogen) to generate TOPO-E1A plasmid, in which the E1A sequence was verified by sequencing analysis. Full-length of androgen receptor (AR full-length), AR without ligand-binding domain (AR ORF 1-1959 bps, named AR TAD-DBD), and AR DNA-binding domain alone (AR ORF 1669-1959 bps, named AR DBD) were synthesized from the AR cDNA by PCR using the primer pairs of 5' TACATCACTCGCGGCCGCAGAAGT-GACACGTTAGGGCTGGGAA (SID NO: 16) and 5'-TCAC TCCTCGAGTC ACTGGGTGTGGAAATAGATGGGC TT (SID NO: 17) for AR full-length (approx. 2.7 kb), 5'-TACAT-CACTCGCGGCCGCAGAAGTGCAGTTAGGGCTGGG AA(SID NO: 18) and 5'-TCACTCCTC GAGTCACT-CAGTGGGGCT GGTGGT GCTGGA (SID NO: 19) for AR-TAD-DBD (approx. 2 kb), 5'-TACATCACTCGCGGC-CGCAAAGACCTGCCTGATCTGTGGAGAT (SID NO: 20) and 5'-TCACTCCTC GAGTCACTCAGTGGGGCT GGTGGT GCTGGA (SID NO: 19) for AR-DBD (approx. 320 bps). These three different lengths of AR PCR products were cloned into the vector pCR2.1-TOPO to generate the plasmids of TOPO-AR full-length, TOPO-AR TAD-DBD, TOPO-AR 080, in which the sequence of these AR inserts were verified by sequencing analysis. The AR fragments were cleaved from TOPO-AR by Not I and Xho I restriction enzyme digestion and inserted at the downstream of the TOPO-E1A to create TOPO-E1A-AR. The E1A-AR fragments were cleaved from TOPO-E1A-AR plasmids by BamH I and Xho I and cloned into pBK-CMV to create the pBK-GMV/E1A-AR constructs. The E1A fragment was cloned into pBK-CMV to create the pBK-CMV/E1A construct. For cloning of E1A reporter plasmid pE1B-luc, E1B promoter with Hind III and BamHI ends was synthesized from Ad5 wild type virus by PCR amplification using primer pair 5'-CCCAAGCTTTCCTTCTAACACACCTCCTG (SID NO: 21) and 5'-GGGGATCCGA GGTCAGATGTAAC-cAAGA (SID NO: 22). The Luciferase gene was cleaved from the plasmid pBK-PSE-PBN-Luc with BamHI and Xmal. The PCR product of E1B promoter and The Gel purified luciferase were cloned into the pUC 19 vector with ends of Hind III and Xma I, generating the E1A reporter plasmid pE1Bluc. The plasmid pcDNA3-hAR was a kindly gift from Dr. William Isasca. To construct the plasmids that the E1A-AR gene expressions are under the control by the prostate specific enhancer (PSE) and rat probasin promoter (PBN), the prostate specific reporter piasmid PBK-PSE-PBN-luc was digested with BamHI and Xhol to remove the luciferase gene. The large fragments containing pBK-PSE-PBN were gel-purified and ligated with the BglII-Xhol fragments of E1A-AR inserts cleaved from pBK-CMV/E1A-AR, generating the plasmids PBK-PSE-PBN-E1A-AR. The E1A-AR chimera in the pBK-PSE-PBN-E1A-AR plasmids includes wild type AR (E1A-AR), transactivation domain of AR (E1A-TAD), and a full-length AR with a point mutation C685Y in the ligand binding domain (E1A-AR.sup.C685Y). The plasmid pBK-PSE-PBN-E1A was constructed by replacing the luciferase gene in the plasmid pBK-PSE-PBN-luc with E1A fragment. All PCR-derived fragments and site-directed mutagenesis were sequenced to confirm their predicted composition.

Construction of shuttle vectors for homologous recombination in bacteria. To generate our recombinant constructs, the original pShuttle vector from AdEasy System was modified as following: an internal BamH I site was ablated and re-introduced into multiple cloning sites (MCS) for insertion of our favorite genes when combined with other restriction enzymes. Our recombinant adenoviruses were designed to have an intact E1B, however, the adenoviral backbone vectors pAdEasy-1 does not contain Ad5 sequences encompassing the E1 genes (nucleotides 1-3,533) and the original pShuttle has impaired E1B. We re-introduced an intact E1B by double digestion of the adenoviral plasmid pFG173 (purchased from Microbix Biosystems) with Hpa I and Bstl107I, this 4193 nucleotide fragment corresponding to the right hand portion of the adenovirus from the E1A polyadenylation signal through into E1 replaced the 2362 nucleotide fragment in the original pShuttle vector, the subsequent plasmid named RpS-TOAD-shuttle (refer to Tissue specific Oncolytic Ad Shuttle vector). To generate shuttle plasmids RpS-PSE-PBN-E1A-AR (AR wt named RP103, AR TAD named RP104, AR$^{C685Y}$ named RP105), the PSE-PBN-E1A-AR fragments were cleaved from plasmid pBK-PSE-PBN-E1A-AR at Bgl II and Xho I sites and then ligated with the shuttle vector RpS-TOAD that was linearized with BamH I and Xho I. The positive control shuttle plasmid RpS-PSE-PBN-E1A (RP101) was generated by insertion of PSE-PBN-E1A fragment into the RpS-TOAD at BamH I and Not I sites. The shuttle plasmid RpS-PSE-PBN-luc (RP106) was generated by insertion of PSE-PBN-luc fragment into the RpS-TOAD at BamH I and NotI sites. The negative control shuttle plasmid RpS-PSE-PBN-null (RP102) was generated by insertion of PSE-PBN-null fragment into the RpS-TOAD at BamH I and Sal I sites.

Generation of Recombinant Adenoviruses. The AdEasier-1 cells were used for transformation of all shuttle plasmids. AdEasier-1 cells are high-recombinant *E. coli*. strain BJ5183 derivatives that have stable transfection of adenoviral backbone AdEasy-1 genome (E1 and E3 region were deleted) to allow for rapid homologous recombination with single step transformation and selection. The shuttle plasmids were linearized with PmeI and then transformed into the AdEasier-1 cells. The clones that had inserts were further characterized with extensive restriction digestion. The digestion patterns were compared with the pAdEasy-1 stock DNA made in a non-recombinant strain. The right clones after screening were transformed into non-recombinant strain DH10B cells for large-scale amplification. These recombinant plasmids were linearized with PacI and transfected into adenovirus packaging cell line 293 cells to generate our recombinant adenoviruses.

Transfection and Luciferase Assay. Cells were plated at $1\times10^4$ per well (triplicates) in 96-well plate at 1 day prior to the transfection in antibiotic-free medium with 10% FBS. 100 ng of the reporter plasmid pBK-PSE-PBN-luc (firefly luciferase gene under control of the prostate specific enhancer and promoter) and 1 ng of the reporter plasmid pRL-luc (Renilla luciferase gene under control of the CMV promoter) were co-transfected with 100 ng of the other interest plasmids using Lipofectamine Plus® Reagent (Gibco). Cells were added OPTI-MEM® medium (Gibco) with dextran-charcoal-stripped serum (10% final concentration) in the presence or absence of synthetic androgen R1881 (Methyltrienolone, Sigma) (final concentration 5 nM) at 3 hours post-transfection. The Luciferase assays (Dual-Glo Luciferase Assay System, Promega) were performed at 24-48 hours post-transfection. All of the transfection assays were triplicates and normalized to the reporter plasmid pRL-luc.

Example 1

E1A Inhibits AR Activation of a Reporter Gene

Figure 1B:
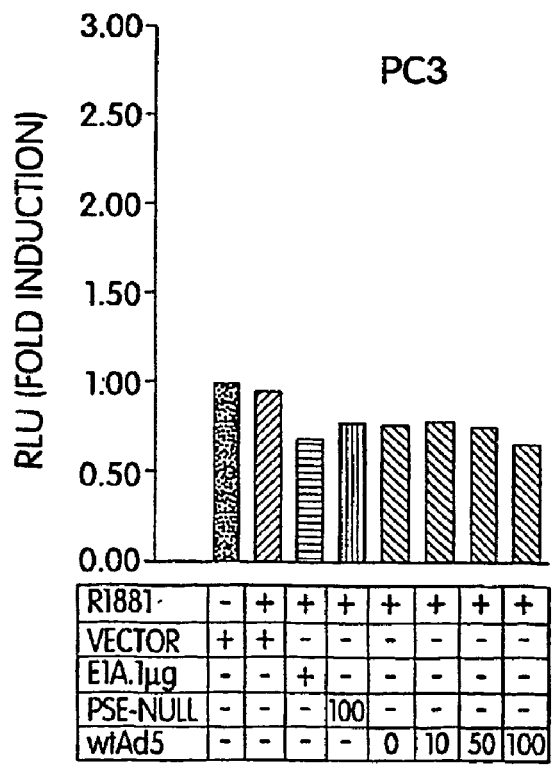
Figure 2A:
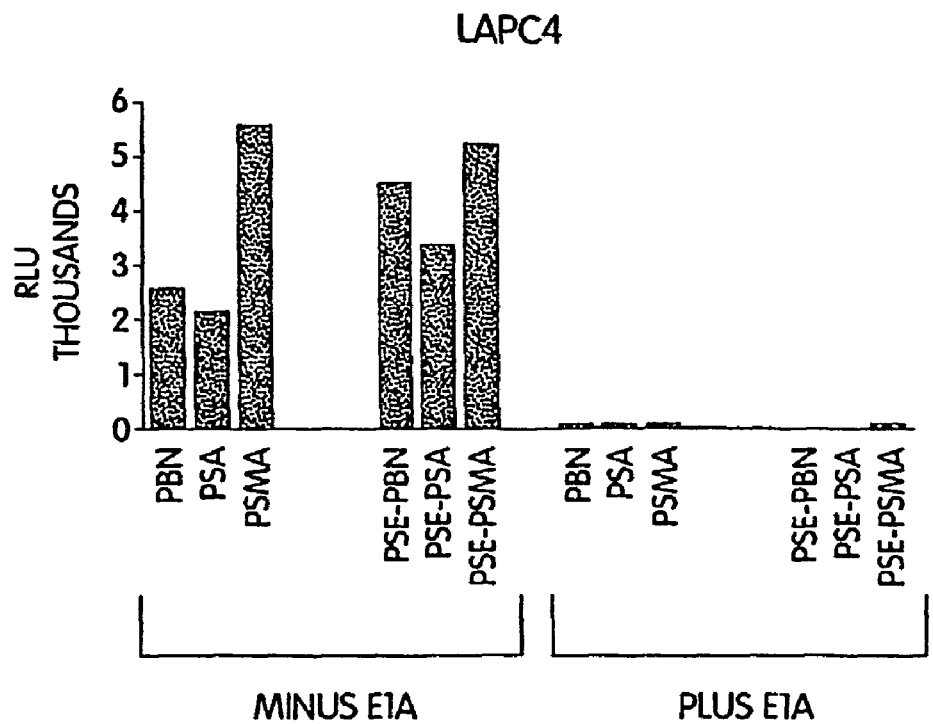
FIG. 2 is bar graph representations illustrating E1A Mediated Inhibition of Various Prostate Specific Promoters; three basic prostate specific promoters (rat Probasin, human PSA, and human PSMA) were used in this analysis, as well as chimeric constructs containing the enhancer element from the PSA gene (−5322 to −3738) fused to the different promoters; these promoter constructs were placed upstream of the luciferase reporter gene; all values reported are normalized using a co-transfected Renilla luciferase reporter; all values reported were performed in the presence of 10 nM R1881; in the appropriately marked lanes, an expression plasmid encoding viral genomic E1A under the control of the CMV promoter was co-transfected at a high level compared to previous experiments (0.5 mcg/well); in A, LNCaP (AR positive) cells demonstrated that the addition of AREs (via the PSE) resulted in augmentation of the PSA promoter and the probasin promoter, but not the PSMA promoter; overexpression of E1A resulted in marked inhibition of expression of the reporters; in B, PC3 (AR minus) demonstrated less total promoter activity, as expected; the addition of AREs (via the PSE) did not result in significant augmentation of transcriptional activity, as there is no AR; overexpression of E1A, however, did demonstrate a decrease in total promoter activity; these results indicate that high levels of E1A can suppress transcription from a variety of prostate specific promoters, even without involving the androgen receptor; RLU are expressed as % Renilla control co-transfection expression (i.e., dual luciferase).
Figure 2B:
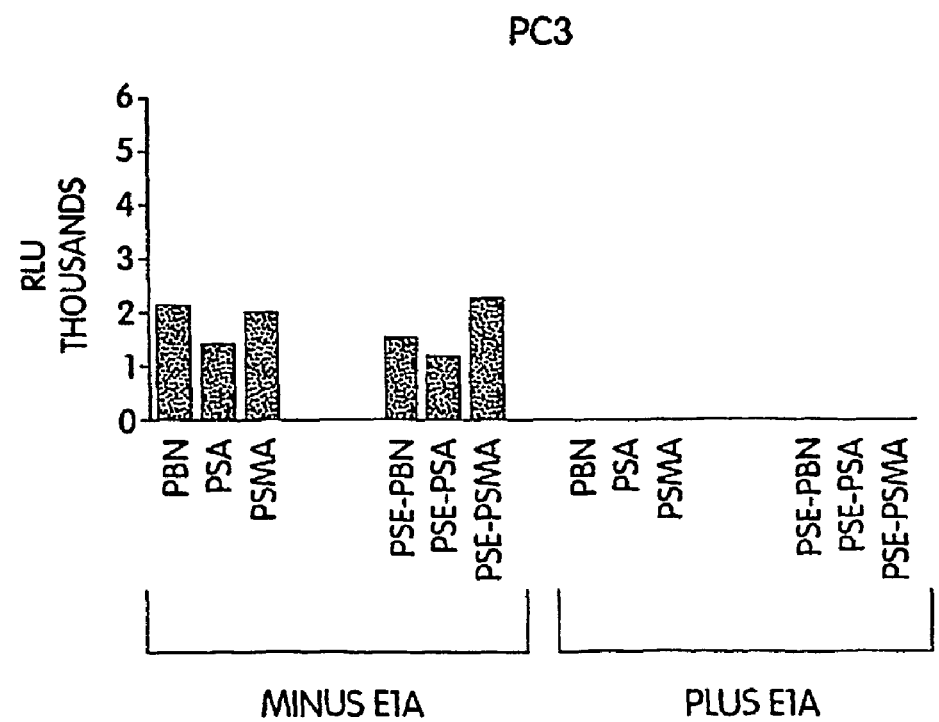

Since the androgen receptor and E1A share many common interactions with mediators of target gene expression, we hypothesized that E1A expression may adversely affect AR activity. In order to test this hypothesis, we cloned the E1A gene from the adenovirus wildtype genome (including both introns 1 & 2) into an expression plasmid (PBK-CMV from Stratagene), under the constitutive control of the CMV promoter. We then performed co-transfection experiments with an androgen inducible promoter (pBK-PSE-PBN-LUC), described above. We chose to use LAPC4 as the AR positive cell line for our analysis, since this cell line expresses wildtype AR, while the more commonly used LNCaP expresses a mutant AR; however, to date we have consistently found similar results with both cell lines when performing androgen induction. PC3 was used as the prototypical AR negative prostate cancer cell line. FIG. 1, Panel A demonstrates the results of co-transfection of the E1A construct and the androgen inducible promoter PSE-PBN-LUC in LAPC4. In the first lane the reporter (pBK-PSE-PBN-LUC) was co-transfected with vector only (pBK-CMV, no insert) in the absence of hormone (R1881). In the next lane, the same conditions were used, but in the presence of 10 nM R1881 (a synthetic androgen). This demonstrated the expected induction of the target reporter gene by the androgen receptor. Incubation with plasmid encoding the E1A gene, however, reversed the hormone induction of the target gene expression. These results were performed over a wide range of plasmid concentrations (0.1 µg to 1 µg) and demonstrated a clear dose-response relationship between E1A expression and inhibition of AR target gene induction, though at concentrations of the E1A plasmid>0.5 µg inhibition of basal expression (i.e., not AR dependent) could also be achieved. The next issue was whether or not the amount of E1A expression required for this inhibition was relevant compared to the amount expressed in typical viral infections. Thus we also performed the same transfection experiment in LAPC4, followed however by infection with either a control virus (PSE-NULL, which is replication deficient and has no E1A trans-gene insert) or an E3 deleted wildtype replicating virus (CN702). Because these viruses can cause replication in: LAPC4, we assayed the effect on target gene expression at 24 hours post-infection to minimize any bias-effect from the lytic cycle on our target gene expression. These data show that while the control virus PSE-Null has roughly the same induction of target gene expression, as the target plasmid alone in the presence of R1881, the wt-E3 deleted CN702 clearly demonstrated a dose response inhibition of AR activity, consistent with our transfection data. By contrast, repeating the exact same experiments in a non-AR expressing prostate cancer cell line (FIG. 1, Panel B, PC3) demonstrated no appreciable induction of target gene expression with androgen. Moreover, in PC3, E1A expression by plasmid or by virus showed only a nominal decrease in the target gene expression—a result also seen with our replication deficient PSE-Null virus, indicating that this is a nonspecific finding. We conclude from these studies that E1A causes direct inhibition of AR function. Similar experiments in LNCaP reveal that the same inhibition occurs (data not shown). In fact, high levels of E1A are capable of suppressing many tissue specific promoters, even in the absence of AREs or AR. An example of this is shown in FIG. 2. In this experiment the probasin promoter, the PSA promoter and the PSMA promoter were all tested, with and without AREs (supplied by fusion of the promoter with the PSA enhancer, aka "PSE") in both LAPC4 and PC3 cells again. Unlike before, here we over-expressed E1A by increasing the pBK-CMV-E1A expression plasmid by 5 fold. All the promoters shown were tested in the presence of 10 nM R1881. The addition of PSEs to the basal promoters did result in an enhancement of androgen dependent transactivation of the reporter genes in LAPC4, but not PC3, as expected. However, over-expression of E1A results in inhibition of transgene expression even in the AR negative PC3 cell line. These data indicate that E1A has a tendency to inactivate prostate specific genes in general and thus enhancement of prostate specific oncolytic gene therapy will require methods that overcome this inhibition.

As outlined above, there are at least two possible mechanisms by which E1A could result in inhibition of AR function: (1) sequestration of common transcriptional regulatory complexes (2) direct interaction with CtBP in an inhibitory complex. In order to help us resolve these two possibilities, we attempted co-immunoprecipitation experiments with antibodies directed against E1A and AR. Despite multiple attempts, we were never able to demonstrate direct interactions between the two proteins (data not shown). Therefore, we conclude that the most probable mechanism was sequestration of the shared transcriptional regulatory factors between E1A and AR. If such a mechanism is correct, we predicted that fusion of the androgen receptor with the E1A gene would convert E1A from a repressor of AR function to a potent co-activator. Thus, we generated several E1A-AR fusion constructs. The major constructs included E1A-AR, E1A-AR-C685Y, E1A-TAD, and E1A-DBD. The AR corresponds to the 2.7 Kb full-length cDNA, fused in frame with E1A by PCR cloning. TAD stands for transactivation domain (amino terminus including AF-1, DNA binding domain and the hinge region). DBD corresponds to the DNA binding domain (both zinc fingers and hinge region). E1A-AR-C685Y corresponds to a fusion containing the full length AR cDNA with a single mutation at codon 685 converting cysteine to tyrosine. This point mutation results in an androgen receptor which is fully activated with nonsteroidal androgen receptor antagonists, such as flutamide and bicalutamide Example 2

AR-E1A Fusion Chimera Markedly Enhances AR Dependent Trans-Gene Activation

Figure 3:
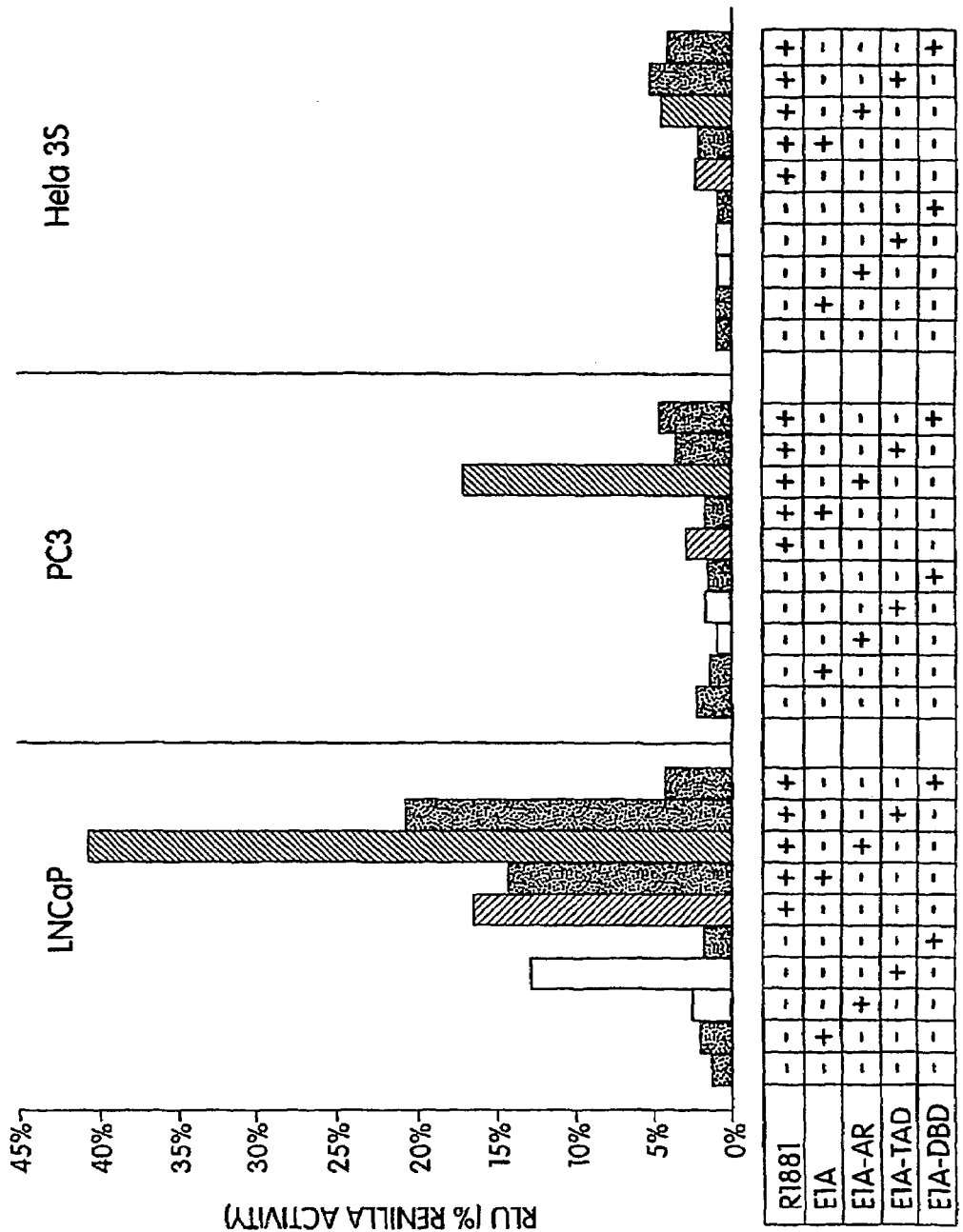
FIG. 3 is bar graph representations illustrating E1A fusions with androgen receptor domains; the various different fusions were tested in 3 different cell lines, in the absence and presence of 10 nM R1881; in A, LNCaP B. PC-3. C. HeLa as can be seen, the LNCap showed remarkable induction of an AR dependent promoter (pBK-PSE-PBN-Luc) with the E1A-AR fusion; a similar effect was seen with PC-3, but to a slightly lessor degree as there is no endogenous AR to complex with the fusion; importantly non-prostate cancer cells (HeLa) are not capable of co-activating this reporter construct with the chimeric fusions.
Figure 4:
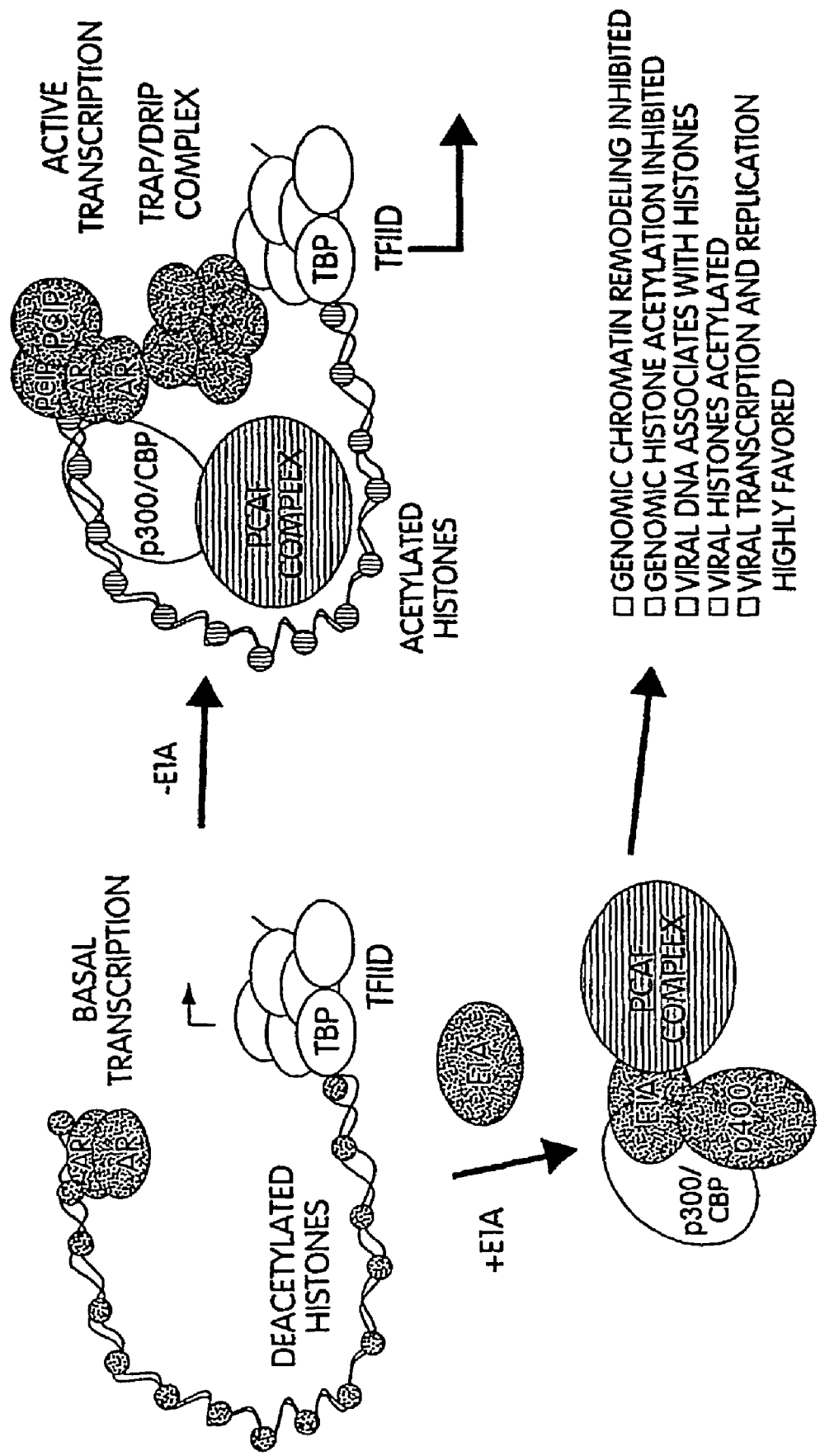
FIG. 4 is a schematic representation of the mechanism of EA1 inhibition.
Figure 5:
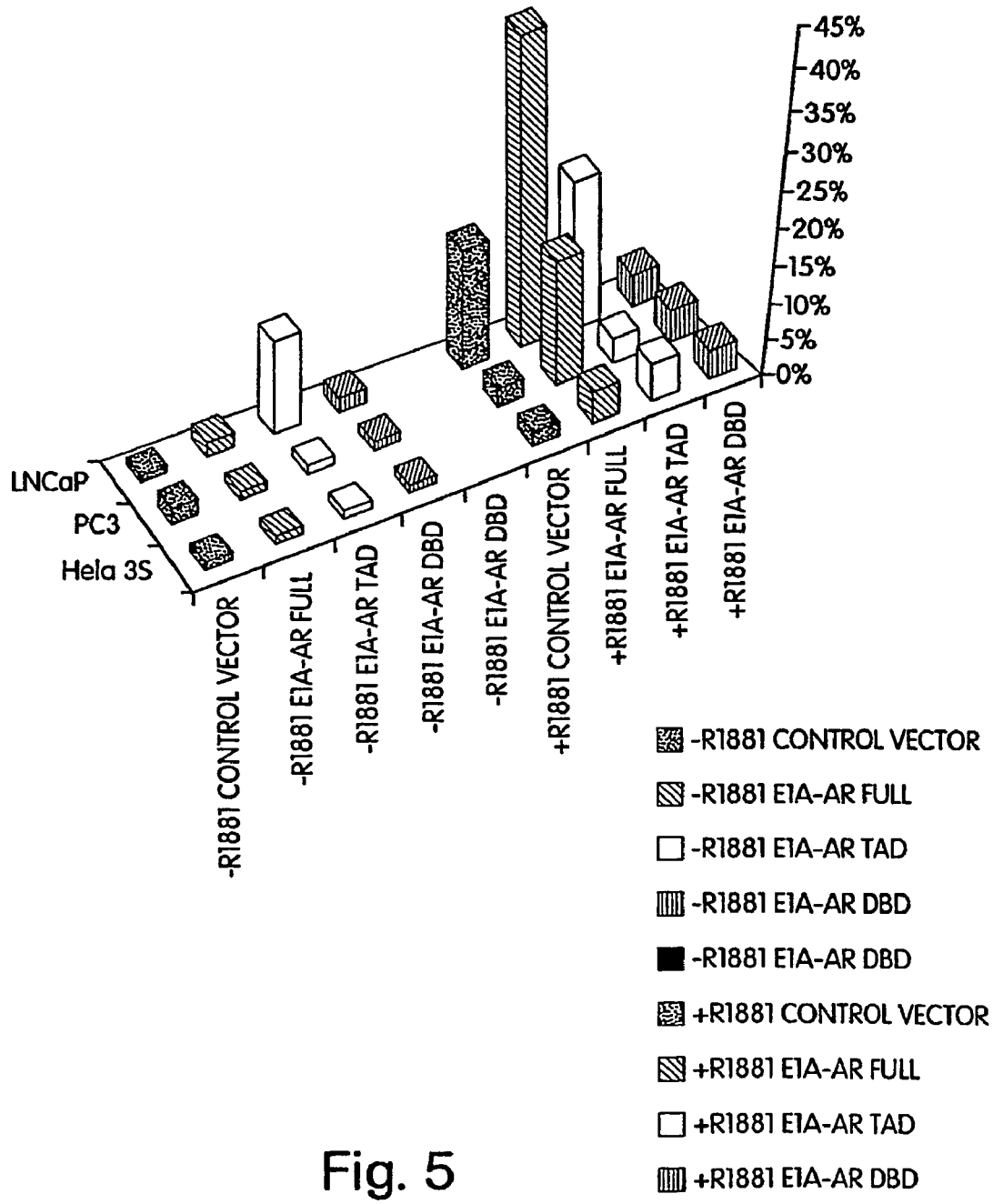
FIG. 5 is a bar graph representation of the regulatory effect of EA1/AR Chimera protein on Prostate Specific Promoter.
Figure 15:
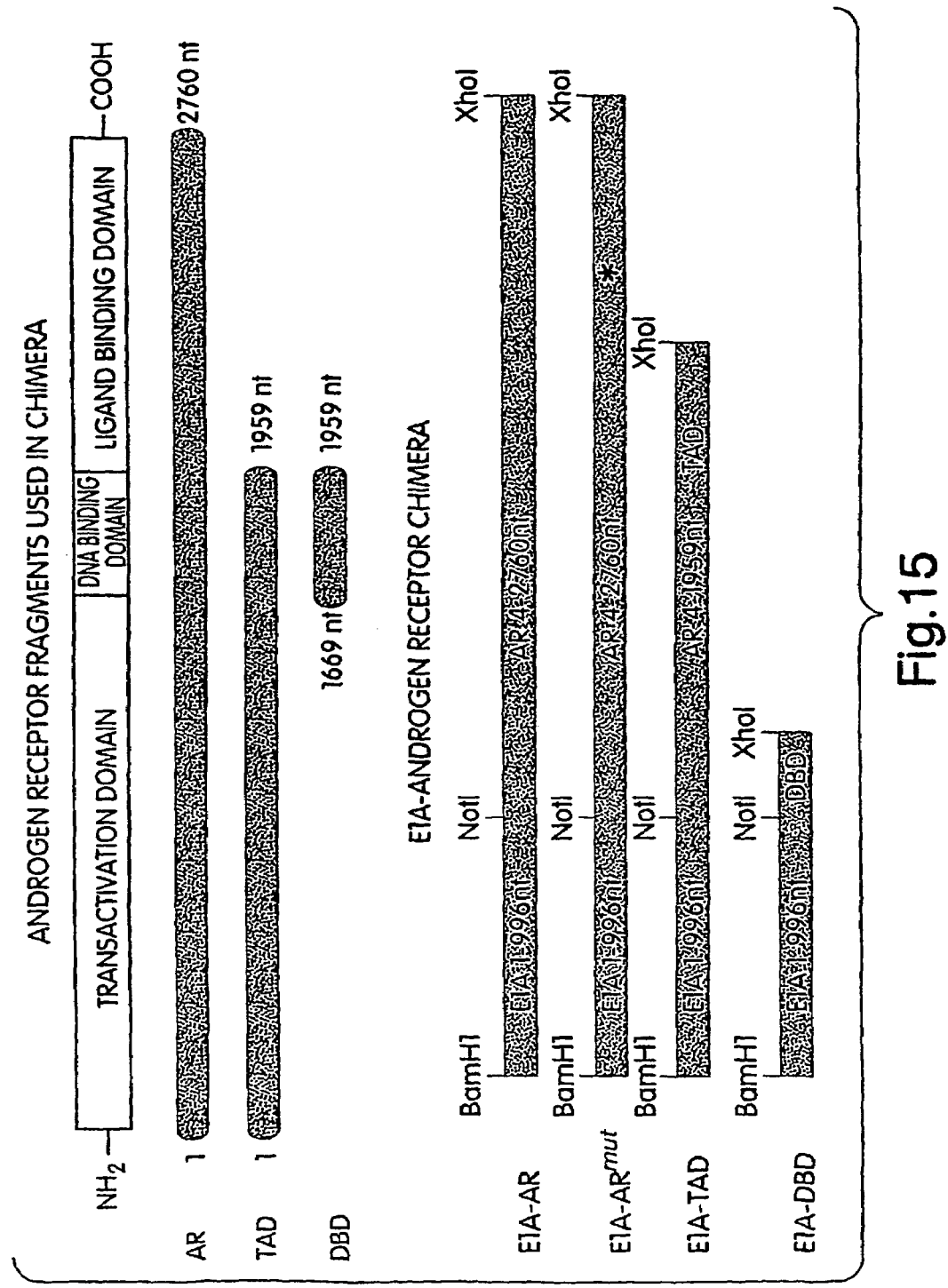
FIG. 15 is a schematic representation of some EA1/AR full length or fragment chimeras of the invention.

We tested our hypothesis that a fusion of E1A and AR domains would convert E1A into a potent co-activator by performing co-transfection of our fusion constructs with an AR dependent reporter construct pBK-PSE-PBN-LUC (FIG. 3). Each well of a 96 well plate was co-transfected with 0.1 µg of an E1A fusion construct, and a fixed amount of pBK-PSE-PBN-LUC (0.1 µg) in the presence or absence of androgen (R1881) in three different cell lines. The first two cell lines were prostate cancer; the last was non-prostate (HeLa). The AR positive line LNCaP demonstrated induction of the reporter with androgen (control), inhibition of induction with E1A, and constitutive expression with E1A-TAD. The full-length AR fusion (E1A-AR) demonstrated an excellent activation with hormone (super-induction), both in the AR positive cell line LNCaP and the AR negative cell line PC3. The E1A-DBD raised basal expression of the reporter slightly in all cell lines in a non-specific and hormone independent fashion. Importantly, the HeLa line failed to demonstrate much activity of any of the constructs with or without androgen. Subsequent experiments confirm the same pattern in LAPC4 as LNCaP and lack of activity in the colon cancer cell line DLD. Thus, the fusion of the E1A-AR is able to convert the AR negative cell line PC3 into an active inducer of prostate specific promoter activity, while maintaining specificity of action. This finding has tremendous implications as it suggests that an oncolytic virus based on such a construct could be useful in patients who have a subpopulation of prostate cancer cells which have lost expression of the androgen receptor. Moreover, it recently occurred to us that a simple point mutation in the AR ligand-binding domain (C685Y) could convert the process from an androgen dependent activation, to an anti-androgen dependent activation. Therefore we recently generated the E1A-AR-C685Y construct by site directed mutagenesis. Our preliminary experiments reveal potent stimulation by bicalutamide to stimulate expression of the AR dependent reporter gene pBK-PSE-PBN-LUC and significant activation by R1881, as expected.

Example 3

Figure 20:
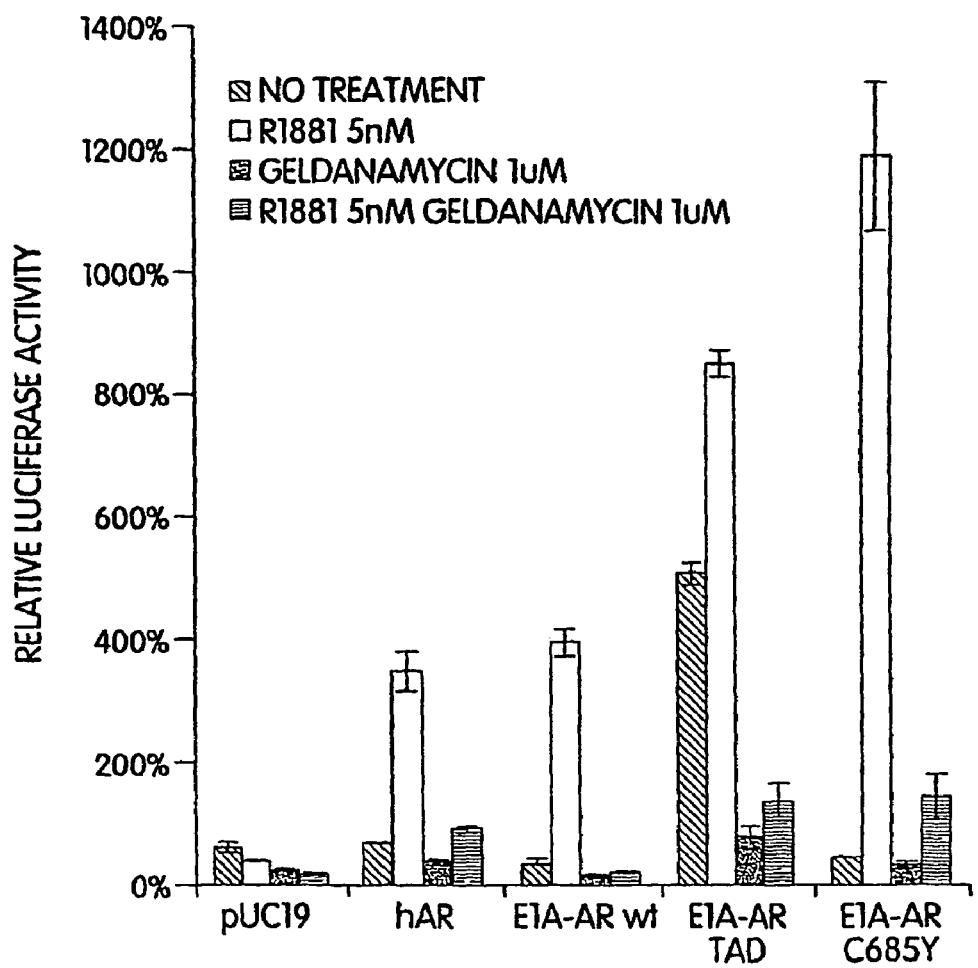
FIG. 20 is bar graph representation of the effect of Geldanamycin on Androgen Receptor function in EA1/Ar chimera transfected COS-1 cells.
Figure 21:
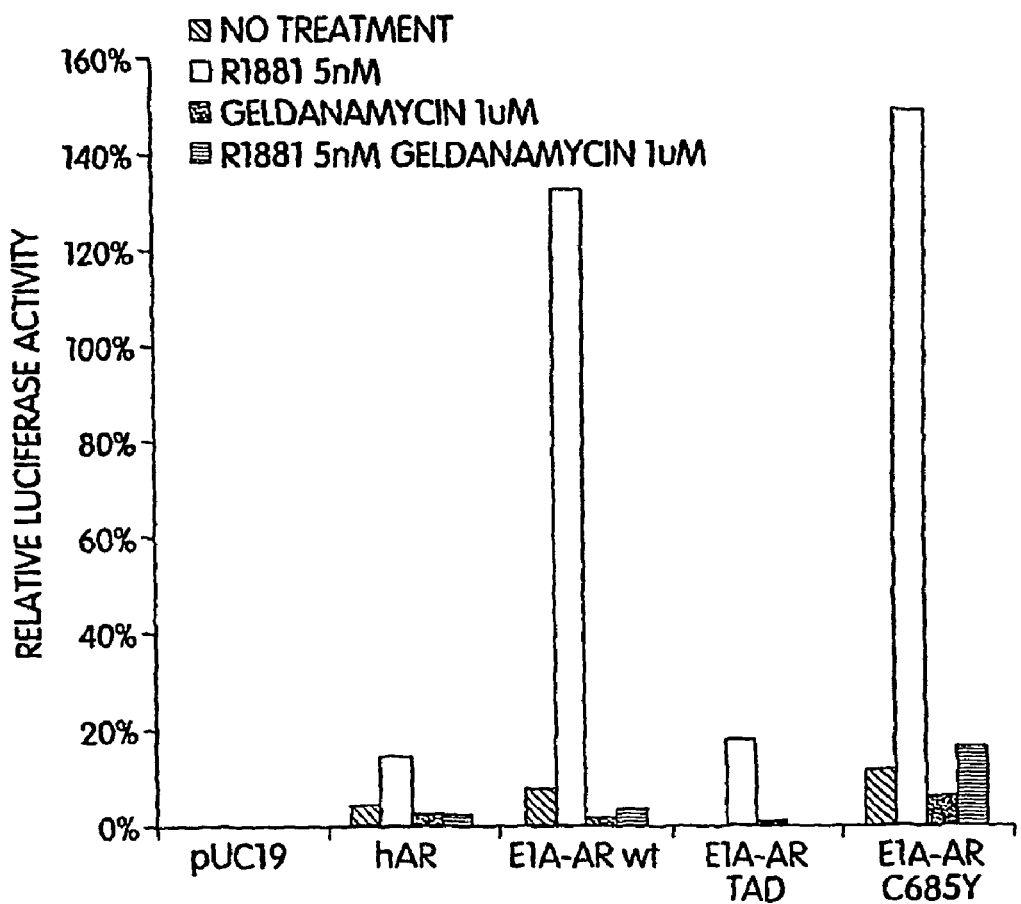
FIG. 21 is bar graph representation of the effect of Geldanamycin on Androgen Receptor function in EA1/Ar chimera transfected PC-3 cells.
Figure 22:
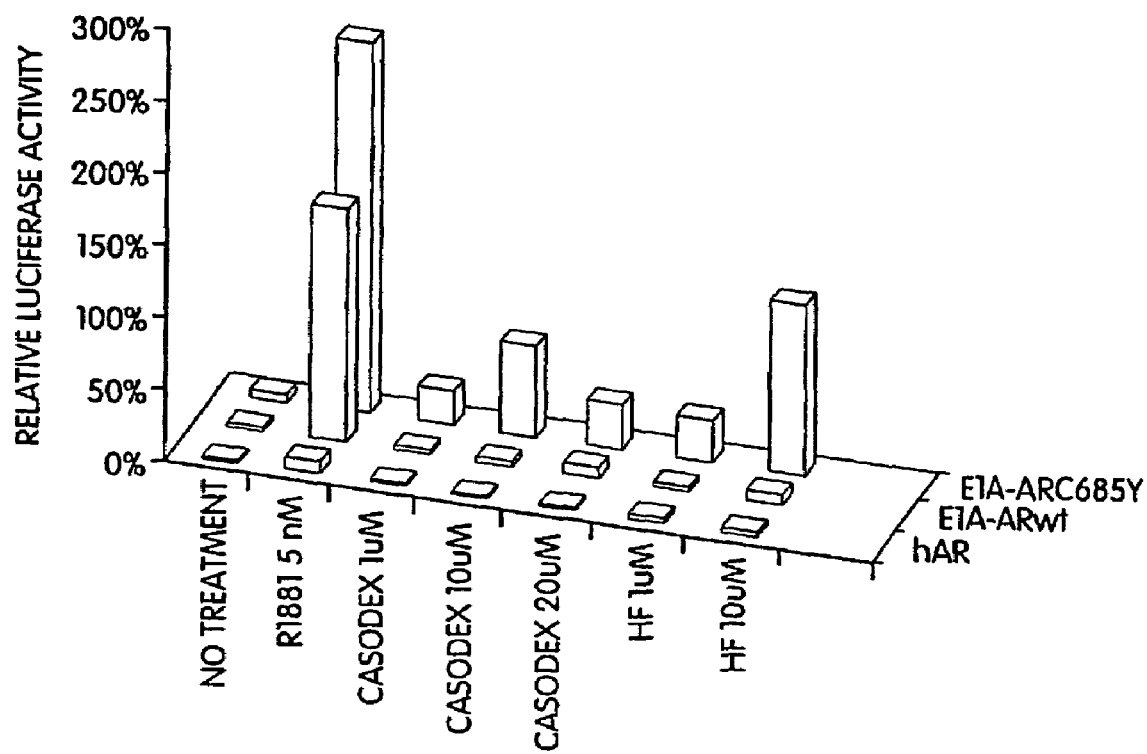
FIG. 22 is a bar graph representation of the effect of androgen agonists and antagonists on the induction of EA1/AR and EA1 (C685Y) in PC3 cells.

The Effect of Geldenamycin on Androgen Receptor Function in EA1/Ar Chimera Transfected PC-3 Cells and COS-1 Cells As illustrated in FIGS. 20 and 21, different chimeras were tested in two different cell lines (PC3 and COS-1 cells) in the presence of hormone (R1881) with and without. Geldenamycin. The results indicate that Geldenamycin can inactivate the effect on expression by the three chimeras, E1A/AR (full length), E1A/TAD and E1A/C685Y. RLU are expressed as % Renilla control co-transfection expression (i.e., dual luciferase).

Equivalents

Those skilled in the art will recognize, or be able to ascertain using no more than routine experimentation, many equivalents to the specific embodiments of the invention described herein. Such equivalents are intended to be encompassed by the following claims.

The present invention relates to compositions and methods for enhancing the oncolytic activity of replication-competent, target cell-specific adenovirus vectors by modification of the E1A gene product. The target cell-specific replication-competent adenovirus vectors comprise a chimera of an adenovirus gene essential for replication, preferably an early gene, and the Androgen receptor (or a portion thereof) under the transcriptional control of a cell type-specific transcriptional regulatory element (TRE). By providing for cell type-specific transcription through the use of one or more cell type-specific TREs, the adenovirus vectors effect prostate-specific cytotoxicity due to selective replication.

We claim:

1. A tissue-specific replication conditional adenovirus vector comprising a heterologous prostate-specific transcriptional regulatory element operably linked to a nucleotide sequence encoding an E1A/Androgen Receptor (AR) chimeric protein.

2. The vector of claim 1, wherein the transcriptional regulatory element is selected from the group consisting of promoters and enhancers and combinations thereof which contain at least one androgen response element.

3. The vector of claim 2, wherein the promoter is selected from the group consisting of prostate-specific promoters with functional androgen response elements including but not limited to the Prostate Specific Antigen (PSA), probasin (PB) and glandular kallikrein-1 gene (hk2).

4. The vector of claim 1, wherein the adenovirus is serotype 5 (Ad5).

5. The vector of claim 1, wherein the E1A/AR chimeric protein is an E1A full length chimeric protein, encoded by SEQ ID NO. 1.

6. The vector of claim 1, wherein the E1A/AR chimeric protein is an E1A/TAD chimeric protein, encoded by SEQ ID NO. 2.

7. The vector of claim 1, wherein the E1A/AR chimeric protein is an E1A/DBD chimeric protein, encoded by SEQ ID NO. 3.

8. The vector of claim 1, wherein the E1A/AR chimeric protein is an 12S/AR full length chimeric protein, encoded by SEQ ID NO. 3 and SEQ ID NO. 7.

9. The vector of claim 1, wherein the E1A/AR chimeric protein is an 12S/TAD chimeric protein, encoded by SEQ ID NO. 5 and SEQ ID NO. 8.

10. The vector of claim 1, wherein the E1A/AR chimeric protein is an 12S/DBD chimeric protein, encoded by SEQ ID NO. 6 and SEQ ID NO. 9.

11. The vector of claim 1, wherein the E1A/AR chimeric protein is an E1A/AR C685Y chimeric protein, encoded by SEQ ID NO. 13.

12. An adenoviral vector particle comprising the viral vector of claim 1.

13. A method of producing a tissue-specific replication conditional adenovirus particle, said particle comprising a heterologous prostate-specific transcriptional regulatory element operably linked to a nucleotide sequence encoding an E1A/Androgen Receptor (AR) chimeric protein.

14. A pharmaceutical composition comprising an adenoviral vector particle of claim 12 and a pharmaceutically acceptable carrier.

15. A method of selectively lysing a neoplastic prostate cell, comprising contacting the cell with an effective amount of the adenoviral vector of claim 12, and wherein the adenoviral vector is delivered by intratumoral injection.

16. A method of treating a host organism having prostate cancer comprising administering a therapeutically effective amount of the composition of claim 14 to one or more neoplastic prostate cells, and wherein the composition is delivered by intratumoral injection.

17. The method of treatment of claim 16, wherein the host organism is a human patient.

* * * * *